(12) United States Patent
Simpson et al.

(10) Patent No.: US 7,336,359 B1
(45) Date of Patent: Feb. 26, 2008

(54) SYSTEM AND METHOD FOR NONLINEAR OPTICAL NULL ELLIPSOMETRY

(75) Inventors: Garth J. Simpson, West Lafayette, IN (US); Ryan M. Plocinik, Lafayette, IN (US); Mark Polizzi, Chapel Hill, NC (US)

(73) Assignee: Purdue Research Foundation, West Lafayette, IN (US)

( * ) Notice: Subject to any disclaimer, the term of this patent is extended or adjusted under 35 U.S.C. 154(b) by 219 days.

(21) Appl. No.: 11/120,350

(22) Filed: May 3, 2005

Related U.S. Application Data

(60) Provisional application No. 60/592,333, filed on Jul. 29, 2004, provisional application No. 60/567,712, filed on May 3, 2004.

(51) Int. Cl.
*G01J 4/00* (2006.01)
(52) U.S. Cl. ............... 356/364; 356/369; 435/288.7
(58) Field of Classification Search ........ 356/364–369, 356/346; 422/50–82.5; 435/288.7; 436/164–172
See application file for complete search history.

(56) References Cited

U.S. PATENT DOCUMENTS

| | | | |
|---|---|---|---|
| 3,741,661 A * | 6/1973 | Yamamoto et al. ......... 356/368 |
| 4,105,338 A | 8/1978 | Kuroha | |
| 4,647,207 A | 3/1987 | Bjork et al. | |
| 4,655,595 A | 4/1987 | Bjork et al. | |
| 4,957,368 A | 9/1990 | Smith | |
| 5,018,863 A | 5/1991 | Vareille et al. | |
| 5,042,951 A * | 8/1991 | Gold et al. ................. 356/369 |
| 5,229,833 A * | 7/1993 | Stewart ...................... 356/364 |
| 5,311,825 A | 5/1994 | Bonham | |
| 5,581,350 A | 12/1996 | Chen et al. | |
| 5,596,411 A | 1/1997 | Fanton et al. | |
| 5,608,526 A | 3/1997 | Piwonka-Corle et al. | |
| 5,657,126 A | 8/1997 | Ducharme et al. | |
| 5,666,200 A | 9/1997 | Drevillon et al. | |
| 5,822,035 A | 10/1998 | Bille | |
| 5,963,326 A | 10/1999 | Masao | |
| 6,052,188 A | 4/2000 | Fluckiger et al. | |
| 6,453,263 B1 | 9/2002 | Sirtori et al. | |
| 6,753,961 B1 | 6/2004 | Norton et al. | |
| 6,804,003 B1 | 10/2004 | Wang et al. | |
| 2004/0051871 A1* | 3/2004 | Kempen ..................... 356/364 |

\* cited by examiner

*Primary Examiner*—Akm Ullah
*Assistant Examiner*—Tara S. Pajoohi
(74) *Attorney, Agent, or Firm*—Woodard, Emhardt, Moriarty, McNett & Henry LLP

(57) ABSTRACT

Nonlinear optical null ellipsometry is disclosed as a method to evaluate second-order nonlinearities on and off resonance in thin surface films and bulk materials.

35 Claims, 15 Drawing Sheets
(2 of 15 Drawing Sheet(s) Filed in Color)

SYSTEM AND METHOD FOR NONLINEAR OPTICAL NULL ELLIPSOMETRY

CROSS REFERENCE TO PRIOR APPLICATIONS

This application claims the benefit of U.S. Provisional Application No. 60/592,333 filed Jul. 29, 2004 and U.S. Provisional Application No. 60/567,712 filed May 3, 2004, which applications are incorporated herein in their entirety.

STATEMENT REGARDING FEDERALLY SPONSORED RESEARCH OR DEVELOPMENT

The U.S. Government has certain rights in the present application as provided by the terms of contract no. 031677, which was funded by the National Science Foundation.

TECHNICAL FIELD OF THE INVENTION

The present invention generally relates to ellipsometry and, more particularly, to a system and method for nonlinear optical null ellipsometry.

BACKGROUND OF THE INVENTION

Ellipsometry is a technique of non-destructive measurement allowing optical characterisation of a sample having a specular or quasi-specular surface. The term ellipsometry is used as a collective term for denoting various methods for studying the physical properties of test samples by means of measuring the amount by which they change the polarization of a polarized light beam. In principle, a beam with a known state of polarization is reflected from or transmitted through the test sample. After reflection at the test sample or after the light has passed through the test sample, the physical properties of the test sample can be ascertained from the change in polarization, using optical calculations.

Ellipsometry is based on the fact that a monochromatic electromagnetic wave changes its intensity and state of polarization if it non-perpendicularly strikes the interface between two dielectric media (for example, a substrate coated with a film). The ellipsometer linearly polarizes the light beam before it strikes the sample surface; linear (or circular) polarization indicates that the light gets only two perpendicular components having the same amplitude. The beam, after going through the interface between the surface film and substrate, is reflected and changes its polarization, i.e. both the ratio amplitude of the two components ($\Psi$) and their phase ($\Delta$) are modified. The two components of the reflected light are no longer mutually perpendicular and have a different amplitude; hence the polarization becomes elliptical and the technique is called ellipsometry. The ellipsometer measures the experimental values of the two components of the reflected light, giving the values $\Psi$ and $\Delta$. The value $\Psi$ is calculated by multiplying the ratio of amplitudes of the incident beam by the amplitudes of the reflected beam; the value $\Delta$ comes from the difference of their phases.

Ellipsometry can be implemented in situ and therefore is well suited to the study of the mechanisms of thin layer growth, the formation of interfaces and the control of the processes used to form these layers and interfaces. For example, during semiconductor fabrication, thin films are deposited on a wafer. The thickness of the films is critical and may be readily determined from ellipsometric measurements. There are numerous other manufacturing processes that also require accurate deposition of thin films. Ellipsometers are routinely used to measure the quality of these processes by analyzing the film properties.

The ellipsometric measurements can be made at one fixed wavelength or at several wavelengths (i.e. spectroscopic ellipsometry). According to the wavelength region of the source (near ultra violet, visible, near infra red, infra red, etc.) it is possible to analyze different properties of layers or of bulk materials. In the ultra violet and visible regions, the depth of penetration of the radiation is often slight. These wavelengths are often used for the study of surfaces and interfaces. Generally this does not allow access to layer volumetric properties of materials which can, however, be obtained through measurements in the infra red region. Infra red is also well suited to measurements of vibrational absorption (chemical bonds).

In reflection ellipsometry, the test sample has a reflective surface on which the light beam impinges with an oblique angle of incidence. The ellipsometric data obtained can be used for ascertaining the refractive index and the extinction coefficient of the surface material of the test sample. If the test sample is covered with a dielectric film, it is possible to determine the thickness and the refractive index of the film. Reflection ellipsometry is the most sensitive and most accurate method for measuring such films or layers. Instead of using a reflected beam, it is also possible to analyze the light beam which is transmitted through the test sample. This method is referred to as transmission ellipsometry. The same procedure which is used for measuring the change in polarization in transmission ellipsometry can also be employed for studying bulk properties of transparent materials, for example the birefrigence of crystals or optical rotation of a sugar solution. The latter is conventionally referred to as polarimetry, but it falls within the general term of ellipsometry. For the sake of simplicity hereinafter, reference will primary be made to reflection ellipsometry but it should be appreciated that, unless stated otherwise, the information and procedures set forth herein also apply to transmission ellipsometry and polarimetry as referred to above.

In ellipsometry, the physical parameters of the test sample, which are the aspects of interest, simultaneously affect the relative intensity and the phase delay of the two polarization components of the light beam. As external influences affect the two polarization components to the same degree, ellipsometry is very insensitive with respect to such external influences. That also explains the extremely high degree of accuracy of ellipsometric measuring methods in conventional laboratory equipment.

An ellipsometer essentially comprises a light source for emitting polarized light, a test sample and an analyser which analyses polarization of the light after it has been reflected at the test sample or after it has been transmitted through the test sample. More particularly, an ellipsometer typically comprises a light source and a detector together with two polarizers, one of which is disposed near the light source and is conventionally referred to as the polarizer, while the other is disposed in the vicinity of the analyzing means and is generally referred to as the analyzer. The test sample is disposed between the polarizer and the analyzer, and the assembly may include one or two devices for altering or modifying the polarization of the light, referred to as polarization modifying devices or polarization modulating devices. The polarization modulating devices may be polarizers which produce a partial polarization effect, birefrigent devices (which are referred to as compensators), or optical rotators and/or geometrical rotators. If, for example, the polarizer is rotated relative to the test sample, that is a geometrical rotation. The differences between the individual kinds of ellipsometers arise out of the choice of the device used for modifying the state of polarization. By virtue of the particular design construction selected, ellipsometers have different properties, for example in regard to accuracy, high measuring speed and suitability for operation with multiple wavelengths.

Because of the non-directional nature of optical laws, the sequence in which the optical components are disposed may be interchanged between the two polarizers. The mode of operation of the overall assembly then remains the same.

In order to carry out ellipsometric measurements, the surface of a sample is illuminated by a light beam and the state of polarization of an incident beam i is compared with that of the reflected beam r or the transmitted beam. A polarization electric field vector E is generally represented by its projections $E_S$ and $E_P$, respectively perpendicular and parallel to the plane of incidence. The projections $E_S$ and $E_P$ are complex amplitudes.

In the domain of linear ellipsometry, the polarization reflectance ratio is traditionally defined to be the ratio of the reflection coefficients p- to s-polarized light $$\rho = R_P/R_S = (E_P/E_S)_r/(E_P/E_S)_i \quad (1)$$

and is indicative of the modifications to the state of polarization produced by the surface being studied. $\rho$ is a complex number, therefore two ellipsometric parameters must be obtained in order to determine $\rho$, which is generally represented in the form:

$$\rho = \tan \Psi \cdot e^{i\Delta} = (E_P/E_S)_r/(E_P/E_S)_i \quad (2)$$

The two parameters $\Psi$ and $\Delta$ describing the change in polarization are thus combined in the complex quantity $\rho$. The parameter $\Psi$ is a measure of the relative intensities (the amplitude ratio) of the p-to-s polarization states of the probe light beam, and the parameter $\Delta$ is a measure of the relative phase shift between the p and s polarization states. The parameters $\Psi$ and $\Delta$, and hence the number $\rho$, depend, at the same time, on the surface properties of the sample, the angle of incidence of a beam and the measurement wavelength. The expression of $\Psi$ and $\Delta$, or of $\rho$, as a function of these parameters, is given by the equations of Fresnel, as is well known in the art.

As a conventional method of obtaining these ellipsometric parameters $\Psi$ and $\Delta$, the null ellipsometry method is known. In null ellipsometry, the change in the state of polarization which is caused by the test sample is compensated by suitable adjustment of the polarization modulating device so that the light beam is extinguished by the analyser. Adjustment to a minimum level of received intensity may be effected either manually or automatically. The measurement result is then the position of the polarization modulating device upon extinction of the light beam. In this method, a polarized beam is radiated from a light source onto a measurement target at a predetermined angle with respect to the target, and a beam reflected by the target, which is elliptically polarized, is transmitted through a $\lambda/4$ (quarter wave) plate and an analyzer to be guided to a light-receiving unit. While optical intensity signals obtained by the light-receiving unit are observed through, e.g., a measuring unit, the $\lambda/4$ plate and the analyzer are rotated to obtain a rotational angle at which the minimum optical intensity is observed. The above-mentioned ellipsometric parameters are calculated on the basis of this rotational angle, as is known in the art.

Second harmonic generation (SHG) and sum-frequency generation (SFG), which are the respective frequency doubling and frequency mixing of light, have emerged as powerful ellipsometric probes for characterizing oriented surface systems. By nature of the unique symmetry of SHG and SFG measurements, the detected signals are often dominated by the oriented chromophores at interfaces and are largely insensitive to greater numbers of randomly oriented species in the bulk. This symmetry condition has been exploited with great success in surface-specific spectroscopic measurements by SHG and SFG at solid/liquid, liquid/liquid, liquid/air, solid/air, semi-conductor, polymer and biological interfaces.

The intensity of the second order nonlinear beam generated from an oriented uniaxial organic film between two isotropic media is dependent on the nonlinear optical susceptibility (described by the rank three $x^{(2)}$ tensor), the incident intensity or intensities, the polarization states of the incident and exigent light, and the linear optical properties of the interfacial system. A routine approach for isolating relative values of the $x^{(2)}$ tensor elements is to compare the intensities of the s- or p-polarized nonlinear beams measured as functions of the polarization state(s) of the incident beam(s). For example, the expressions in Eqs. 3 and 4 below (or variations thereof) are commonly used in reflection SHG measurements of achiral uniaxial interfacial films performed using linearly polarized incident light with the plane of polarization rotated away from purely p-polarized by the angle $\gamma$.

$$I_s^{2\omega} = C \cdot \frac{1}{4} \sin^2(2\gamma) |s_1 x_{XXZ}|^2 (I^\omega)^2 \quad (3)$$

$$I_p^{2\omega} = C \cdot |s_5 x_{ZXX} + \cos^2\gamma(-s_3 x_{XXZ} + s_5 x_{ZXX} - s_5 x_{ZXX} + s_7 x_{ZZZ})|^2 (I^\omega)^2 \quad (4)$$

In standard reflection and transmission measurements of achiral films far from resonance, relative values of the tensor elements are easily obtained from the ratios of the second harmonic intensities measured under different polarization conditions or from nonlinear curve-fitting.

As new samples, unique substrates and diverse interfacial systems are increasingly investigated by SHG and SFG, many of the simplifying assumptions routinely used to treat polarization measurements may not hold. For example, the Fresnel factors that describe the electric fields at an interface will be complex-valued in studies conducted in total internal reflection or in studies of multilayer films. The Fresnel factors will also generally be complex in systems in which the nonlinear film, the substrate, or the ambient medium absorbs either the incident or exigent light (e.g., in spectroscopic studies). Finally, if the nonlinear surface layer absorbs one or more of the incident or exigent optical frequencies, the $x^{(2)}$ tensor elements themselves will also be complex-valued. In any or all of these instances, even the simple expressions in Eqs. 3 and 4 (or variations thereof) describing SHG can become complicated. Expansion of the expressions in Eqs. 3 and 4 in the most general case of SHG measurements with complex fitting coefficients and complex tensor elements yields the expressions in Eqs. 5 and 6.

$$I_s = C \frac{1}{4} \sin^2(2\gamma) \begin{bmatrix} \text{Re}(s_1)^2 \text{Re}(\chi_{XXZ})^2 + \text{Im}(s_1)^2 \text{Im}(\chi_{XXZ})^2 + \\ \text{Re}(s_1)^2 \text{Im}(\chi_{XXZ})^2 + \text{Im}(s_1)^2 \text{Re}(\chi_{XXZ})^2 \end{bmatrix} \quad (5)$$

$$I_p = C \left\{ \begin{aligned} &\text{Re}(s_6)\text{Re}(\chi_{ZXX}) - \text{Im}(s_6)\text{Im}(\chi_{ZXX}) + \\ &\cos^2\gamma \begin{bmatrix} -\text{Re}(s_3)\text{Re}(\chi_{XXZ}) + \text{Re}(s_5)\text{Re}(\chi_{ZXX}) - \text{Re}(s_6)\text{Re}(\chi_{ZXX}) + \text{Re}(s_7)\text{Re}(\chi_{ZZZ}) \\ +\text{Im}(s_3)\text{Im}(\chi_{XXZ}) - \text{Im}(s_5)\text{Im}(\chi_{ZXX}) + \text{Im}(s_6)\text{Im}(s_7)\text{Im}(\chi_{ZZZ}) \end{bmatrix} \end{aligned} \right\}^2 \quad (6)$$

$$+ C \left\{ \begin{aligned} &\text{Re}(s_6)\text{Im}(\chi_{ZXX}) + \text{Im}(s_6)\text{Re}(\chi_{ZXX}) + \\ &\cos^2\gamma \begin{bmatrix} -\text{Re}(s_3)\text{Im}(\chi_{XXZ}) + \text{Re}(s_5)\text{Im}(\chi_{ZXX}) - \text{Re}(s_6)\text{Im}(\chi_{ZXX}) + \text{Re}(s_7)\text{Im}(\chi_{ZZZ}) \\ -\text{Im}(s_3)\text{Re}(\chi_{XXZ}) + \text{Im}(s_5)\text{Re}(\chi_{ZXX}) - \text{Im}(s_6)\text{Re}(\chi_{ZXX}) + \text{Im}(s_7)\text{Re}(\chi_{ZZZ}) \end{bmatrix} \end{aligned} \right\}^2$$

It is immediately apparent that extracting the real and imaginary components of the three independent tensor elements present in SHG from the second harmonic intensity measured as a function of $\gamma$ is nontrivial. Even assuming the $x^{(2)}$ tensor elements are purely real, Eqs. 5 and 6 yield a minimum of two possible solutions for the relative tensor elements (for $x_{ZXX}$ and $x_{XXZ}$ of like and opposite sign).

An alternative detection approach was pioneered during the emergence of nonlinear optical surface measurements of uniaxial films in which a rotating polarizer is placed between the sample and the detector. As described hereinabove, rather than compare normalized intensity ratios, the rotation angle of the polarizer that resulted in extinction of the nonlinear beam was used to determine relative values of the tensor elements and subsequently molecular orientation. Using this type of approach, the ambiguity regarding the relative sign between $x_{ZXX}$ and $x_{XXZ}$ in principle can be removed. However, this rotating polarizer approach will only produce a true null provided the nonlinear beam is linearly polarized, which generally limits its reliable application to standard reflection and transmission measurements of vanishingly thin transparent films far from resonance (in which case both the $x^{(2)}$ tensor elements and the Fresnel factors are purely real).

SUMMARY OF THE INVENTION

Nonlinear optical null ellipsometry is disclosed as a method to evaluate second-order nonlinearities on and off resonance in thin surface films and bulk materials.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 10b contains an expanded view of the region corresponding to the minimum in FIG. 10a.

DETAILED DESCRIPTION OF THE PREFERRED EMBODIMENTS

Figure 1:
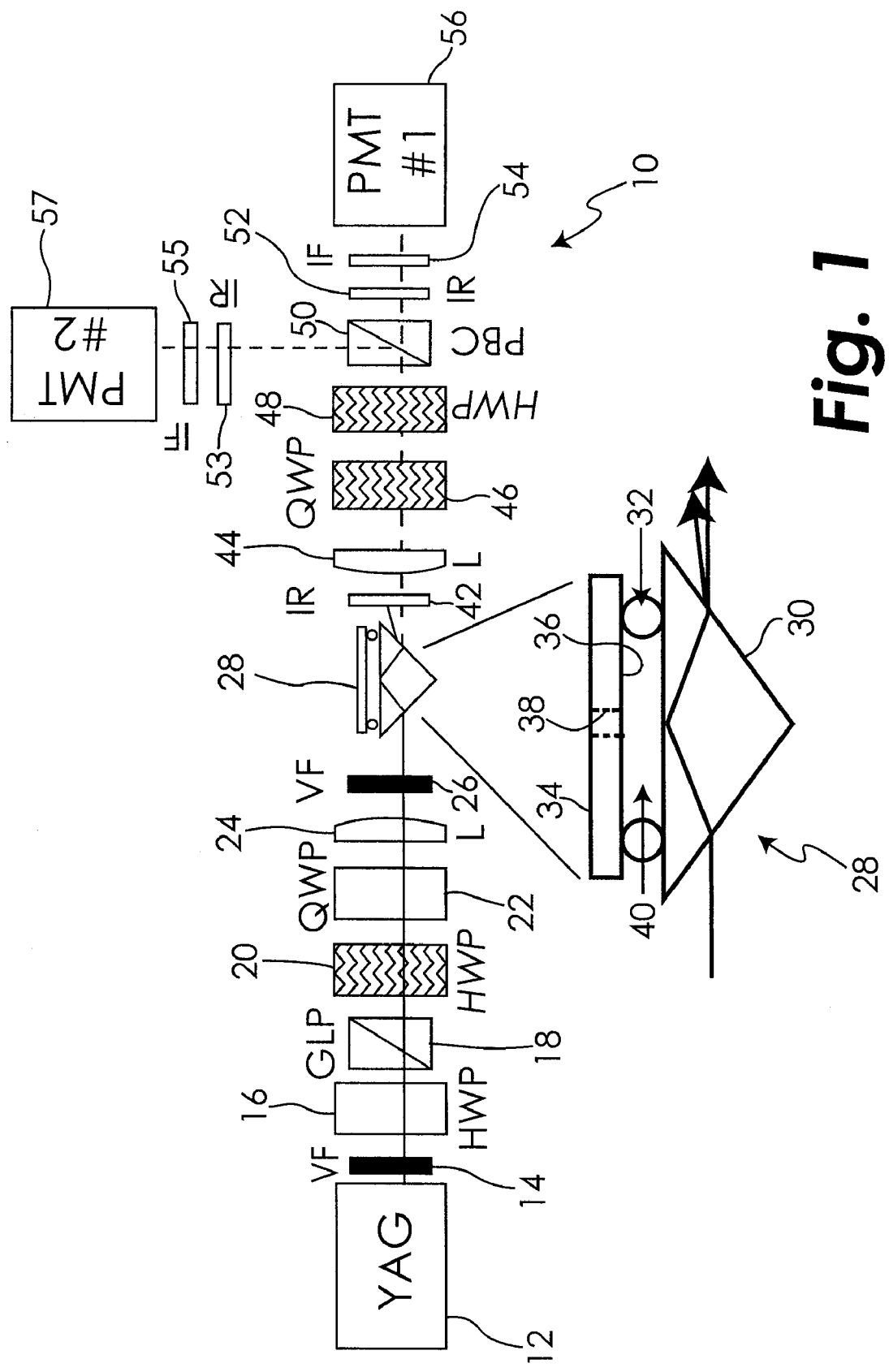
FIG. 1 schematically illustrates the optical path for a first embodiment instrument used for nonlinear optical null ellipsometry.

For the purpose of promotion an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principle of the invention as illustrated therein being contemplated as would normally occur to one skilled in the art to which the invention relates.

Given the sensitive dependence of SHG and SFG on thin film optical properties and the long tradition of ellipsometry as a successful tool for interpreting surface optics, the present inventors have developed a new approach for acquiring and interpreting nonlinear optical surface measurements combining these linear and nonlinear techniques. As described hereinabove, in a typical ellipsometry measurement, an incident beam of known polarization is directed at the sample. The polarization state of the reflected light can be related back to the ellipsometric angles ψ and Δ, from which the optical properties of the surface can be determined. In linear ellipsometry, ρ is traditionally defined to be the ratio of the p- to s-polarized reflection coefficients and is related to ψ and Δ through the following relation.

$$\rho \equiv \frac{R_p}{R_s} = \tan\psi \times e^{i\Delta} \tag{7}$$

Inherent characteristics of nonlinear optics prevent simple definition of the nonlinear signal in terms of ellipsometric reflection or transmission coefficients. A more general notation will be adopted herein, in which the nonlinear parameter $\rho^{2\omega}$ is defined as the complex ratio of the p- to s-polarized second harmonic electric field amplitudes.

$$\rho^{2w} \equiv \frac{E_p^{2w}}{E_s^{2w}} \tag{8}$$

As described hereinbelow, nonlinear optical null ellipsometry (NONE) is developed theoretically and demonstrated experimentally as a novel method to directly determine the full complex-valued $\chi^{(2)}$ tensor element ratios from nonlinear polarization measurements. For simplicity, the discussion hereinbelow is presented in terms of SHG, although the approach is general enough to also be applicable in SFG investigations.

1. TENSOR ELEMENTS FROM INTENSITY MEASUREMENTS

Provided that the electric-dipole allowed $\chi^{(2)}$ tensor elements for surface second harmonic generation are purely real (or more generally of identical phase), their relative values can be interrogated from polarization-dependent intensity (PDI) measurements acquired under a minimum of three different polarization conditions, such as those described in Eqs. 9, 10, and 11.

$$I_{pp}^{2\omega} = C|-s_3\chi_{XXZ}+s_5\chi_{ZXX}+s_7\chi_{ZZZ}|^2 \tag{9}$$

$$I_{ps}^{2\omega} = C|s_6\chi_{ZXX}|^2 \tag{10}$$

$$I_{s45}^{2\omega} = \frac{1}{4}C|s_1\chi_{XXZ}|^2 \tag{11}$$

The first subscript on $I^{2\omega}$ in Eqs. 9–11 indicates the polarization component of the second harmonic beam and the second subscript the polarization of a linearly polarized incident beam. For example, $I_{s45}^{2\omega}$ refers to the s-polarized intensity recorded for an incident beam linearly polarized with the plane of polarization rotated 45° with respect to the p and s coordinates. In all cases, it is assumed the second harmonic intensities are normalized by the square of the fundamental intensity. The relative values of $\chi_{ZXX}$ and $\chi_{XXZ}$ are simple to determine.

$$\frac{\chi_{ZXX}}{\chi_{XXZ}} = \pm 2\frac{|s_1|}{|s_6|}\sqrt{\frac{I_{ps}^{2\omega}}{I_{s45}^{2\omega}}} \tag{12}$$

Since the relative sign of $\chi_{ZXX}$ and $\chi_{XXZ}$ cannot be determined from the intensity alone, two solutions result (as indicated by the ± symbol).

In contrast to $x_{ZXX}/x_{XXZ}$, evaluation of $x_{ZZZ}/x_{XXZ}$ from $I_{pp}^{2\omega}$ is complicated by possible complex contributions in the fitting coefficients. Expansion of Eq. 9 yields the expression in Eq. 13.

$$I_{pp}^{2\omega} = C \begin{Bmatrix} \chi_{XXZ}^2|s_3|^2 + \chi_{ZXX}^2|s_5|^2 + \chi_{ZZZ}^2|s_7|^2 \\ -2\chi_{XXZ}\chi_{ZXX}[\text{Re}(s_3)\text{Re}(s_5) + \text{Im}(s_3)\text{Im}(s_5)] \\ -2\chi_{XXZ}\chi_{ZXX}[\text{Re}(s_3)\text{Re}(s_7) + \text{Im}(s_3)\text{Im}(s_7)] \\ -2\chi_{ZXX}\chi_{ZZZ}[\text{Re}(s_5)\text{Re}(s_7) + \text{Im}(s_5)\text{Im}(s_7)] \end{Bmatrix} \quad (13)$$

Combination and rearrangement of Eqs. 11 and 13 yields the following relationship between the ratio of $I_{pp}^{2\omega}/I_{s45}^{2\omega}$ and $x_{ZZZ}$ assuming purely real tensor elements.

$$0 = ax_{ZZZ}^2 + bx_{ZZZ} + c \quad (14a)$$

$$a = |s_7|^2 \quad (14b)$$

$$b = x_{ZXX}[|s_5 + s_7|^2 - |s_5|^2 - |s_7|^2] - x_{XXZ}[|s_3 + s_7|^2 - |s_3|^2 - |s_7|^2] \quad (14c)$$

$$c = [-s_3 x_{XXZ} + s_5 x_{ZXX}]^2 - \tfrac{1}{4}|s_1|^2(I_{pp}^{2\omega}/I_{s45}^{2\omega}) \quad (14d)$$

The quadratic formula can be used to determine two solutions for $x_{ZZZ}/x_{XXZ}$ for each solution in Eq. 12, for a total of four possible sets of relative tensor elements that are consistent with a given set of intensity measurements.

If the tensor elements themselves are also allowed to be complex (as would be expected in resonance-enhanced or spectroscopic investigations), determining the many unique solutions for the real and imaginary components of the tensor elements from intensity measurements alone is significantly more complicated.

2. GENERALIZED NULL ELLIPSOMETRIC DETECTION

FIG. 1 schematically illustrates the optical path for a first embodiment instrument used for nonlinear optical null ellipsometry as described herein, the optical path being indicated generally at 10. A light source 12 is provided as an incident light source. The light source may supply light of substantially a single wavelength (e.g. from a laser) or it may supply multiple wavelength radiation (e.g. from several lasers or other broadband light sources. The light beam from laser 12 passes through a first visible absorbing filter (VF) 14, a first half-wave plate (HWP) 16, a Glan laser polarizer (GLP) 18, a second half-wave plate (HWP) 20, a first quarter-wave plate (QWP) 22, a first plano-convex lens (L) 24, and a second visible absorbing filter (VF) 26 before being applied to a total internal reflection cell 28 containing the test sample.

Total internal reflection cell 28 is designed to contain a liquid test sample to be subjected to the incident beam of the ellipsometric tests described herein. Cell 28 comprises a prism 30 having an o-ring 32 positioned thereon. A plate 34 (for example, an aluminum plate) rests upon the o-ring 32, thereby forming a sample chamber 36 bounded by the aluminum plate 34, the o-ring 32 and the prism 30. An aperture 38 is preferably provided in the aluminum plate 34 to facilitate introduction of a liquid sample 40 (for example, a dye solution) into the sample chamber 36.

The exigent beam leaving the total internal reflection cell 28 passes through a first infrared absorbing filter (IR) 42, a second plano-convex lens (L) 44, a second quarter-wave plate (QWP) 46, a third half-wave plate (HWP) 48, a polarizing beam splitting cube (PBC) 50, a second infrared absorbing filter (IR) 52, and a first 532 mm interference filter (IF) 54 before being applied to a first photomultiplier tube (PMT) 56 detector.

The instrument 10 includes an optional second detection path output from the PBC 50, comprising a third infrared absorbing filter (IR) 53, a second 532 mm interference filter (IF) 55, and a second photomultiplier tube (PMT) 57 detector.

The present inventors believe that the nonlinear nature of second harmonic generation lends itself to the use of a generalized ellipsometric approach. Using the instrumental configuration shown in FIG. 1, a null at the detector must satisfy the expression in Eq. 15, written using Jones matrix notation.

$$\begin{bmatrix} 0 \\ 0 \end{bmatrix} = [M_P^{2\omega}(\tfrac{\pi}{2})][M_H^{2\omega}(\alpha_H^{2\omega})][M_Q^{2\omega}(\alpha_Q^{2\omega})]e^{2\omega} \quad (15)$$

In Eq. 15, $e^{2\omega}$ describes the far-field complex second harmonic electric-field polarization emanating from the interface, and the superscripts of $2\omega$ indicate angles and matrices for the second harmonic beam. The capital M's indicate the Jones matrices for the rotated optical elements, with $M_P^{2\omega}$ representing the polarizing beam-splitting cube, $M_H^{2\omega}$ the half-wave plate, and $M_Q^{2\omega}$ the quarter-wave plate. The Jones matrices for the rotated elements are determined from combinations of the Jones matrix evaluated with the fast axis of the optical element parallel with the p-polarized component of the field (i.e., M(0)) and rotation matrices describing the change in reference frame as the optical element is rotated. Mathematically, $M(\alpha) = R(-\alpha)M(0)R(\alpha)$, in which the R's indicate the appropriate rotation matrices for rotation of the reference frame by the angles in parentheses. In practice, the values for $\alpha_Q^{2\omega}$ and $\alpha_H^{2\omega}$ yielding a null are determined experimentally for a given incident fundamental polarization state. Evaluation and simplification of the rotated Jones matrices in Eq. 15 yields the expression in Eq. 16.

$$\begin{bmatrix} 0 \\ 0 \end{bmatrix} = \begin{bmatrix} 0 & 0 \\ 0 & 1 \end{bmatrix} \begin{bmatrix} \cos(2\alpha_H^{2\omega}) & \sin(2\alpha_H^{2\omega}) \\ \sin(2\alpha_H^{2\omega}) & -\cos(2\alpha_H^{2\omega}) \end{bmatrix} \begin{bmatrix} \cos(2\alpha_Q^{2\omega}) - i & \sin(2\alpha_Q^{2\omega}) \\ \sin(2\alpha_Q^{2\omega}) & -\cos(2\alpha_Q^{2\omega}) - i \end{bmatrix} \begin{bmatrix} e_p^{2\omega} \\ e_s^{2\omega} \end{bmatrix} \quad (16)$$

Further simplification of Eq. 16 using Euler's formula leads to the following expression for the relationship between the complex polarization of the nonlinear beam and the angles of $\alpha_H^{2\omega}$ and $\alpha_Q^{2\omega}$ that produce a null in the detected second harmonic intensity.

$$\rho^{2\omega} \equiv \frac{e_p^{2\omega}}{e_s^{2\omega}} = \frac{\cos(2\Delta^{2\omega}) + i\cos(2\alpha_H^{2\omega})}{-\sin(2\Delta^{2\omega}) + i\sin(2\alpha_H^{2\omega})}. \quad (17)$$

A generalized notation has been adopted herein in which $\rho$ is defined to be the complex ratio of the p-polarized to s-polarized electric fields, rather than the ratio of reflection (or transmission) coefficients as in linear ellipsometry.

3. JONES MATRIX DESCRIPTION OF SURFACE SECOND HARMONIC GENERATION

The polarization state of the second harmonic light generated at an interface is a function of the surface second-order nonlinear optical polarizability tensor $x^{(2)}$, the polarization state of the incident field, and the Fresnel factors relating the field amplitudes at the interface with the incident and exigent fields. For a uniaxial surface film with $C_\infty$ symmetry, only four nonzero independent tensor contributions to $x^{(2)}$ remain in SHG, $x_{ZZZ}$, $x_{ZXX}=x_{ZYY}$, $x_{XXZ}=x_{XZX}=x_{YYZ}=x_{YZY}$, and $x_{XYZ}=x_{XZY}=-x_{YXZ}=-x_{YZX}$. The last set of elements disappears for surfaces with mirror-plane $C_{\infty v}$ symmetry. The nonlinear interfacial polarization for SHG measurements of an achiral film is given in Eq. 18.

$$P^{2\omega} = \begin{bmatrix} 2\chi_{XXZ}e^\omega_{L,X}e^\omega_{L,Z} \\ 2\chi_{XXZ}e^\omega_{L,Y}e^\omega_{L,Z} \\ \chi_{ZXX}(e^\omega_{L,X})^2 + \chi_{ZXX}(e^\omega_{L,Y})^2 + \chi_{ZZZ}(e^\omega_{L,Z})^2 \end{bmatrix} \quad (18)$$

The polarization vector of the incident beam within the interfacial layer $e_L^\omega$ is given by matrix multiplication of the far-field incident polarization $e^\omega$ with a 3×2 transformation matrix $T_L$ projecting the s and p coordinate system to the surface coordinate system and a diagonal 3×3 matrix $L^\omega$ containing the appropriate Fresnel factors describing the local field components ($e_L^\omega = L^\omega T_L^\omega e^\omega$). Similar matrix algebra can be used to relate the nonlinear polarization within the interfacial film to the second harmonic intensities far from the interface ($e^{2\omega} = T_{-L}^{2\omega} L^{2\omega} e_L^{2\omega}$). Performing the appropriate matrix algebra yields the relation in Eq. 19 for SHG measurements acquired in reflection.

$$e^{2\omega} = \begin{bmatrix} -s_3\chi_{XXZ}(e^\omega_p)^2 + s_5\chi_{ZXX}(e^\omega_p)^2 + s_6\chi_{ZXX}(e^\omega_s)^2 + s_7\chi_{ZZZ}(e^\omega_p)^2 \\ s_1\chi_{XXZ}e^\omega_p e^\omega_s \end{bmatrix} \quad (19)$$

The $s_n$ fitting coefficients include all the angular terms and the appropriate Fresnel factors. As defined, these coefficients are valid both for chiral and achiral interfaces for an arbitrary polarization of the incident beam. Explicit expressions for the fitting coefficients used for these measurements may be found in G. J. Simpson, J. Chem. Phys. 117 (2002) 3398.

Evaluation of the appropriate Jones matrices for the polarizer/half-wave plate/quarter wave plate arrangement of FIG. 1 with the polarizer set to pass s-polarized light and $\alpha_Q^{2\omega} = -45°$ yields the following expression for the polarization of the incident field.

$$e^\omega \propto \begin{bmatrix} i & 1 \\ 1 & i \end{bmatrix} \begin{bmatrix} \cos(2\alpha_H^{2\omega}) & \sin(2\alpha_H^{2\omega}) \\ \sin(2\alpha_H^{2\omega}) & -\cos(2\alpha_H^{2\omega}) \end{bmatrix} \begin{bmatrix} 0 & 0 \\ 0 & 1 \end{bmatrix} \begin{bmatrix} e^\omega_p \\ e^\omega_s \end{bmatrix}_{in} \propto \begin{bmatrix} \exp(-2i\alpha_H^\omega) \\ i\exp(2i\alpha_H^\omega) \end{bmatrix} \quad (20)$$

Figure 2:
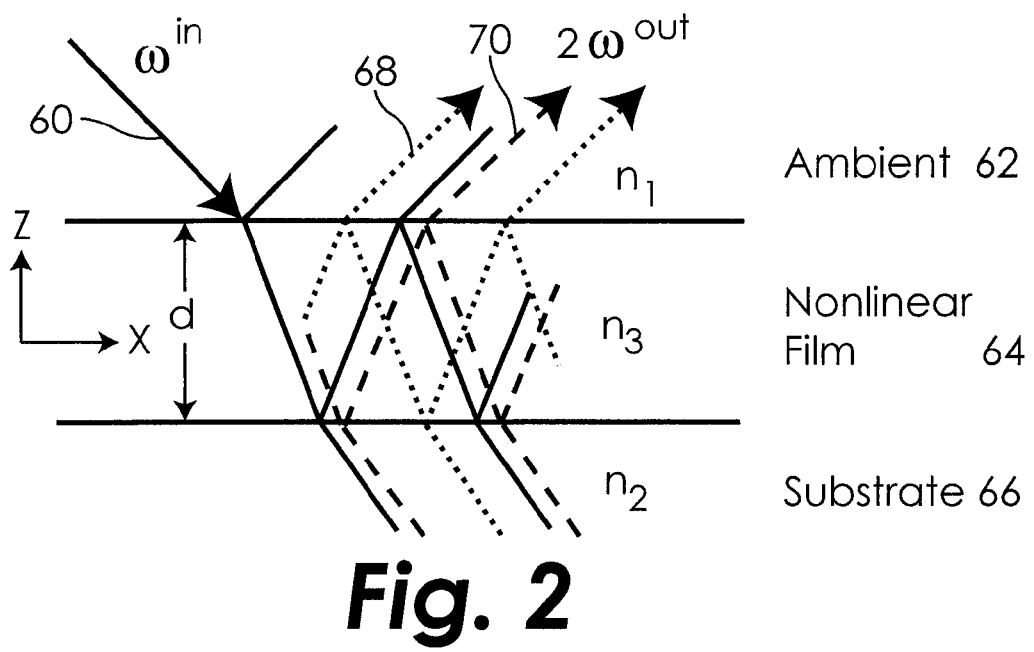
FIG. 2 is a schematic cross-sectional view of a thin film and substrate test sample illustrating second harmonic generation in an ultra-thin film.

FIG. 2 is a schematic cross-sectional view of a thin film and substrate test sample illustrating second harmonic generation in an ultra-thin film. The incident beam 60 (solid lines) transitions from the ambient atmosphere 62, through nonlinear film 64 and into the substrate 66. At each interface, the beam 60 is partially reflected and partially transmitted. The dotted lines 68 indicate the second harmonic source initially propagating upward, while the dashed lines 70 indicate the second harmonic source initially propagating downward. Substitution of $e_p^{2\omega}$ and $e_s^{2\omega}$ into Eq. 19 yields the following expression describing the second harmonic polarization generated from an achiral uniaxial system for the configuration shown in FIG. 2.

$$\rho^{2\omega}(\alpha_H^\omega) = \frac{e_p^{2\omega}}{e_s^{2\omega}} = \frac{[-s_3\chi_{XXZ} + s_5\chi_{ZXX} + s_7\chi_{ZZZ}]\exp(-4i\alpha_H^\omega) + s_6\chi_{ZXX}\exp(4i\alpha_H^\omega)}{is_1\chi_{XXZ}} \quad (21)$$

The relationship in Eq. 21 provides a link between the complex value of $\rho^{2\omega}$ measured from the null angles $\alpha_H^\omega$ and $\alpha_Q^\omega$ given in Eq. 17 and the $x^{(2)}$ nonlinear optical tensor elements. Complex ratios of the tensor elements can be determined by combining measurements of $\rho^{2\omega}$ acquired for multiple rotation angles of $\alpha_H^\omega$. Using the relations $e^0=1$, $e^{i\pi/2}=i$, and $e^{-i\pi/2}=-i$, the following equalities can be easily derived.

$$\rho^{2\omega}\left(\frac{\pi}{8}\right) + i\rho^{2\omega}(0) = -2\frac{s_6\chi_{ZXX}}{s_1\chi_{XXZ}} \quad (22)$$

$$\rho^{2\omega}\left(\frac{\pi}{8}\right) - i\rho^{2\omega}(0) = -2\left(\frac{s_5\chi_{ZXX}}{s_1\chi_{XXZ}} + \frac{s_7\chi_{ZZZ}}{s_1\chi_{XXZ}} - \frac{s_3}{s_1}\right) \quad (23)$$

The ratios of the tensor elements are straightforward to determine from the measured values of $\rho^{2\omega}$.

$$\frac{\chi_{ZXX}}{\chi_{XXZ}} = -\frac{s_1}{2s_6}\left[\rho^{2\omega}\left(\frac{\pi}{8}\right) + i\rho^{2\omega}(0)\right] \quad (24)$$

$$\frac{\chi_{ZZZ}}{\chi_{XXZ}} = \frac{s_3}{s_7} - \frac{s_5\chi_{ZXX}}{s_7\chi_{XXZ}} - \frac{s_1}{2s_7}\left[\rho^{2\omega}\left(\frac{\pi}{8}\right) - i\rho^{2\omega}(0)\right] \quad (25)$$

Since both the fitting coefficients and the $\rho^{2\omega}$ values in Eqs. 24 and 25 are allowed to be complex, the real and imaginary components of the relative tensor elements can be uniquely determined from the ellipsometric nulling angles without the need for complicated nonlinear curve-fitting algorithms and with no a priori knowledge of the surface hyperpolarizability.

4. EXAMPLE 1

The experiments of Example 1 were performed using an instrument as described in FIG. 1. A New Wave Research Polaris Neodymium:Yttrium Aluminum Garnet (Nd:YAG) laser (available from New Wave Research, Inc., 48660 Kato Road, Fremont, Calif. 94538) was used as the light source 12, and generated 5–7 ns pulses of 1064 nm light at 20 Hz. The infrared light was passed through a visible-blocking RG695 filter 14 and the beam power was attenuated through the combination of a half-wave plate 16 and Glan laser polarizer 18 set to pass s-polarized light. After attenuation, the beam passed through a half-wave plate 20 in a rotating mount, a quarter-wave plate 22 fixed at −45°, a plano-convex lens 24, and a final visible-blocking filter 26. Approximately 1 mJ per pulse of incident light was then focused onto the solid/liquid interface of a total internal reflection sample cell 28. After exiting the cell 28, 532 nm light generated at the sample 40/prism 30 interface was passed through an infrared absorbing KG3 filter 42 and recollimated with a second lens 44. The light then passed through a quarter-wave plate 46, a half-wave plate 48, a polarizing beam splitting cube 50 oriented to pass s-polarized light, a second KG3 filter 52, and a 532 nm interference filter 54 before introduction to a photomultiplier tube 56 (Burle 8850, available from Burle Industries, Inc., 1000 New Holland Avenue, Lancaster, Pa. 17601-5688). The intensity of the nonlinear response was read directly off an oscilloscope (Tektronix TDS 540, available from Tektronix, Inc., 14200 SW. Karl Braun Drive, P.O. Box 500 Beaverton, Oreg. 97077) following preamplification (EG&G Ortec 9305, available from EG&G ORTEC, 100 Midland Rd., Oak Ridge, Tenn. 37830).

In a given NONE measurement, the intensity of the nonlinear response was manually nulled by iteratively rotating the 532 nm quarter wave plate 46 and half-wave plate 48 until a minimum in the peak-to-peak potential from the PMT 56 was observed on the oscilloscope (~30 averages). Background signal from dark noise was ~10 mV, a prism 30 with no sample would generate a ~20 mV background, and a sample with a nulled signal produced ~30 mV. The signal detected under nulled conditions was typically more than two orders of magnitude smaller than the maximized signal (obtained by rotating the 532 nm half-wave plate 48 45° from the null angle).

Solutions of $1.0 \times 10^{-3}$ M rhodamine 6G (R-6G, Aldrich, ~99% pure, available from Sigma-Aldrich Chemical Co., Milwaukee, Wis.) and $5.0 \times 10^{-4}$ M disperse red 19 (DR-19, Aldrich, ~95% pure, available from Sigma-Aldrich Chemical Co., Milwaukee, Wis.) in 2-propanol (Mallinckrodt, HPLC grade, available from Mallinckrodt Baker, Inc., Red School Lane, Phillipsburg, N.J.) were introduced to the prism/solution interface of the total internal reflection cell 28. Prior to use, the prism 30 was cleaned by immersion in chromic acid (LabChem Inc., 10%, available from LabChem Inc., 200 William Pitt Way, Pittsburgh, Pa. 15238) for 15 minutes followed by a thorough rinsing with ultrapure water (>17.5 MΩcm). The prism 30 was then rinsed with 2-propanol before being placed into the sample cell 28. To contain the dye solutions; an o-ring 32 was sandwiched between the total internal reflection face of the prism 30 and a thin piece of aluminum (1" square) 34 machined with a ~⅛" hole 38 for solution introduction/extraction.

Figure 3:
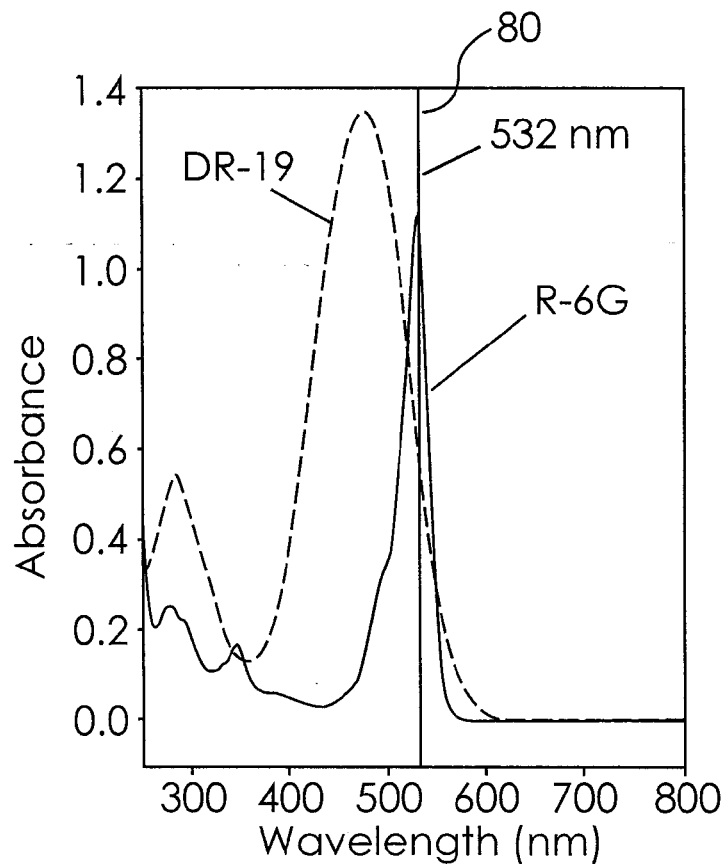
FIG. 3 is a graph of absorbance vs. wavelength showing the ultraviolet-visible spectra for two dye solutions analyzed with the instrument of FIG. 1.

Ultraviolet-visible spectra for both dye solutions are shown in FIG. 3. The vertical bar 80 in the figure indicates the second harmonic wavelength (532 nm). In the case of R-6G, the second harmonic wavelength is resonant with a strong transition within the chromophore ($\lambda_{max}$=529.5 nm). In contrast, the second harmonic for DR-19 is within the absorption envelope but not perfectly on-resonance ($\lambda_{max}$=475.2 nm).

The null rotation angles for the half-wave plate 48 and quarter wave plate 46 are compiled in Table 1.

TABLE 1

Null angles (°) detected using NONE for disperse red 19 and rhodamine 6G

|  | DR 19 | | R-6G | |
| --- | --- | --- | --- | --- |
|  | $\alpha_Q^{2\omega}$ | $\alpha_H^{2\omega}$ | $\alpha_Q^{2\omega}$ | $\alpha_H^{2\omega}$ |
| $\alpha_H^{\omega} = 0°$ | 132 (±2) | −185 (±2) | 27 (±5) | 210 (±3) |
| $\alpha_H^{\omega} = 22.5°$ | −119 (±2) | −17 (±2) | 36 (±1) | 153 (±1) |

The averages and standard deviations were determined from five replicates.

Consistent with Eqs. 22 and 23, null measurements were made for both circular and linear incident polarizations of light ($\alpha_H^{\omega}$=0° and 45°, respectively). The complex-valued $\chi^{(2)}$ tensor elements were obtained from sums and differences of $\rho^{2\omega}$ values as described in Eq. 24 and 25 (Table 2 and 3).

TABLE 2

Values of the $\chi^{(2)}$ tensor elements for R-6G in 2-propanol, normalized for $\chi_{xxz} = 1$

|  | NONE | PDI | | | |
| --- | --- | --- | --- | --- | --- |
|  |  | (+) | (−) | (+) | (−) |
| $\chi_{xxz}$ | 1 | 1 | | 1 | |
| $\chi_{zxx}$ | −0.5 (±0.2) − 0.52i (±0.09i) | 0.90 (±0.02) | | −0.90 (±0.02) | |
| $\chi_{zzz}$ | 1.7 (±0.1) + 0.7i (±0.1i) | 1.54 (±0.08) | −1.78 (±0.08) | 1.50 (±0.08) | −1.83 (±0.08) |
| $\chi_{zzz}/\chi_{zxx}$ | −2.3 (±0.3) + 1.2i (±0.4i) | 1.7 (±0.1) | −2.0 (±0.1) | −1.7 (±0.1) | 2.0 (±0.1) |

The tensor components determined from the intensity-based measurements were evaluated assuming purely real $\chi^{(2)}$ elements and yielded four possible solutions consistent with the set of experimental results.

TABLE 3

Values of the $\chi^{(2)}$ tensor elements for DR-19 in 2-propanol, normalized for $\chi_{xxz} = 1$

|  | NONE | PDI | | | |
| --- | --- | --- | --- | --- | --- |
|  |  | (+) | (−) | (+) | (−) |
| $\chi_{xxz}$ | 1 | 1 | | 1 | |
| $\chi_{zxx}$ | 0.9 (±0.1) − 0.14i (±0.09i) | 0.97 (±0.04) | | −0.97 (±0.04) | |
| $\chi_{zzz}$ | 2.5 (±0.3) + 1.0i (±0.2i) | 2.5 (±0.1) | −2.6 (±0.1) | 2.5 (±0.1) | −2.1 (±0.1) |

In contrast to the NONE measurements, the PDI approach required the assumption of purely real $x^{(2)}$ tensor elements and yielded a set of four possible solutions. In solving for the normalized value of the $x_{ZXX}$ tensor element, the square root of the intensity ratio was taken (Eq. 12) for which $x_{ZXX}$ and $x_{XYZ}$ could be either of like or opposite sign. Subsequent use of the quadratic formula to calculate the $x_{ZZZ}$ tensor element produced two solutions for each of the two sign possibilities for $x_{ZXX}$. From the intensity data, the set of four possible solutions for the three independent nonzero $x^{(2)}$ tensor elements, normalized with respect to $x_{XXZ}$, are summarized in Tables 2 and 3. The fitting coefficients used to calculate values for the relative tensor elements for both the NONE and PDI measurements can be found in G. J. Simpson, J. Chem. Phys. 117 (2002) 3398. The dielectric constant of the thin film was assumed to be the average of the corresponding prism and solution dielectric constants, such that $n_{film}^2 = (n_{prism}^2 + n_{substrate}^2)/2$. Previous investigations indicate an intermediate value for the refractive index of the nonlinear layer yields physically reasonable results in nonlinear optical polarization measurements of submonolayer films.

Since NONE measurements retain phase information in the fully complex tensor ratios while the PDI measurements do not, the NONE results should correctly predict the observed relative intensity data (although the reverse is not generally true). A comparison of the measured relative intensities and those predicted from the NONE measurements is summarized in Table 4 for both DR-19 and R-6G.

TABLE 4

Comparison of the experimental intensity ratios and those predicted from the NONE data

|  | Observed | Predicted from NONE |
|---|---|---|
| Disperse red 19 | | |
| $I_{ps}/I_{s45}$ | 0.88 (±0.08) | 0.8 (±0.2) |
| $I_{pp}/I_{s45}$ | 7.2 (±0.5) | 8 (±1) |
| Rhodamine 6G | | |
| $I_{ps}/I_{s45}$ | 0.76 (±0.03) | 0.5 (±0.2) |
| $I_{pp}/I_{s45}$ | 2.8 (±0.3) | 4.1 (±0.6) |

With DR-19, the predicted intensity ratios were within experimental error of the measured values for both $I_{ps}/I_{s45}$ and $I_{pp}/I_{s45}$. Although qualitatively similar results were observed comparing the measured intensity ratios for R-6G with those predicted from NONE, this system yielded values outside the range of experimental error for $I_{ps}/I_{s45}$ and $I_{pp}/I_{s45}$. A possible explanation for this discrepancy could be the relatively simple treatment used to model the interfacial optics.

Previous studies with disperse red dyes and R-6G suggest that DR-19 should be dominated by the $\beta_{z'z'z'}$ element and that R-6G is dominated by the $\beta_{x'x'z'}$ element at the wavelengths used in this Example. Consistent with these limits, the ratio of $x_{ZXX}/x_{XXZ}$ is expected to be 1 for DR-19 and the ratio of $x_{ZZZ}/x_{ZXX}$ should be −2 for R-6G. NONE measurements of DR-19 yielded $x_{ZXX}/x_{XXZ} = 0.9$ (±0.1)−0.14i (±0.09i), a value within error of unity and almost purely real. The most closely-matched PDI solution assuming purely real tensor elements with $x_{ZXX}$ and $x_{XXZ}$ of like sign yielded a ratio of 0.97 (±0.04), in good agreement with both expectations and the NONE measurements. In the case of R-6G, NONE yielded $x_{ZZZ}/x_{ZXX} = -2.3$ (±0.3)+1.0i (±0.2i). Of the four possible solutions from PDI measurements assuming purely real tensor elements, the tensor ratio that most closely matches the NONE results (i.e., $x_{ZXX} = -0.90 \pm 0.02$ and $x_{ZZZ} = 1.50 \pm 0.08$) yielded a ratio of $x_{ZZZ}/x_{ZXX} = -1.7$ (±0.1).

The poor correspondence between the NONE results and the PDI results presumably stems from the improper application of the PDI approach in systems on resonance, in which the assumption of purely real tensor components is no longer justified.

The fully-resonant results for R-6G summarized in Table 2 demonstrate the importance of retaining relative phase information in surface second harmonic generation investigations. The imaginary component of the $x_{ZZZ}/x_{ZXX}$ ratio is half as great as the real component in the R-6G film and is large enough to be significant. Consequently, care must be taken when interpreting $x^{(2)}$ tensor elements from intensity-based measurements in resonance-enhanced and/or spectroscopic investigations. Even near resonance as in the case of DR-19, imaginary contributions can be non-negligible (Table 3). Using simple expressions that are only strictly valid far from resonance such as those in Eqs. 12 and 14 can lead to significant errors for systems with complex-valued tensor elements on or near resonance. In contrast to PDI methods, NONE measurements can be reliably and easily employed both on and off resonance for systems with real or complex Fresnel coefficients (e.g., for dyes absorbing incident or exigent light, for multilayer films, and/or for measurements acquired in total internal reflection).

5. USE OF NONE IN BIOSENSING APPLICATIONS

The surface selectivity of second harmonic generation (SHG) coupled with the reasonably high sensitivity and simple instrumentation requirements demonstrated hereinabove promises significant potential for the use of nonlinear optical methods in biosensing applications. By providing surface-specific information in real time, nonlinear optical sensing approaches present attractive alternatives to other optical-based sensing techniques for in situ detection of unlabeled proteins (for example), including surface plasmon resonance (SPR), traditional ellipsometry, and waveguide techniques. Furthermore, the nonlinear optical approaches disclosed herein are largely insensitive to subtle changes in the bulk refractive index that often plague SPR, waveguide, and ellipsometry analyses. Most of these linear optical methods also impose specific requirements on the surfaces and/or substrates that can be used. The greater flexibility in substrate selection and inherent surface specificity of surface second harmonic generation has led many groups to pursue nonlinear optical approaches for transducing protein/interface interactions. Since methods for reliably detecting unlabeled proteins are far more attractive for a host of practical reasons, the large majority of SHG protein adsorption studies to date have relied on detecting the native nonlinear optical protein response (analogous to autofluorescence). Notable exceptions include work by Salafsky, in which protein binding kinetics were measured using "SHG-labels" (Salafsky, J. S. Chem. Phys. Lett. 2001, 342, 485), and by Salafsky and Eisenthal, in which protein binding was transduced from the concomitant reduction in the native background SHG response of the charged silica/water interface (Salafsky, J. S.; Eisenthal, K. B. J. Phys. Chem. B 2000, 104, 7752).

With the one exception of the study by Salafsky and Eisenthal, a major limitation of these previous nonlinear optical studies has been the required use either of proteins with substantial native nonlinear optical activities or of labeled proteins. Clearly, altering a protein by the attachment of a fluorescent or SHG-active label not only potentially influences its biological and surface activity, it also introduces additional sample preparation procedures. Alternatively, reliance on the native protein nonlinear optical response generally prohibits the facile detection of protein—protein interactions using surface-immobilized proteins, for which the SHG-activity of the initial protein-decorated surface is likely to compete with the analyte response. Without this flexibility for surface design, methods relying on the native protein nonlinearity generally are limited to monitoring non-specific surface-association at relatively simple interfaces. Although the method developed by Salafsky and Eisenthal circumvents the need for significant nonlinear optical activity from the native protein, the relatively weak signals obtained from the bare water/silica interface arise exclusively from changes in the surface potential, which again places significant restrictions on the surface architectures that may be employed.

As described hereinbelow, nonlinear optical null ellipsometry for signal isolation (NONE-SI) is demonstrated as a novel and general method for background-free real-time biosensing of protein/surface interactions. This method may be practiced using the instrumentation depicted in FIG. 1. As disclosed hereinabove, the exigent beam in nonlinear optical surface measurements is generally elliptically polarized (including linear and circular polarizations as specific subsets). By passing the beam through a quarter wave plate (QWP) 46 rotated at the appropriate angle, the resulting beam can be transformed from elliptically to linearly polarized. With an appropriate selection of a half wave plate (HWP) 48 rotation angle, the beam can be completely rejected at a subsequent polarizer. Irrespective of the initial polarization state, a combination of half and quarter wave plate rotation angles exists that produces zero intensity at the detector. From the wave plate rotation angles resulting in intensity minima, the complete polarization state of the nonlinear optical beam can be determined, which is the basis for the nonlinear optical null ellipsometry (NONE) disclosed herein. Following this nulling procedure, surface binding of an analyte generally induces a change in the polarization state of the nonlinear optical beam. Consequently, the initial combination of wave plate rotation angles no longer yields zero intensity, but rather results in a signal that scales quadratically with the surface concentration of adsorbate (assuming a second-order nonlinear optical process). This methodology can be used to form a biosensing instrument that is capable of accurately measuring adsorption kinetics at a film interface. For example, this novel approach was used for the real-time background-free detection of unlabeled bovine serum albumin (BSA) adsorption kinetics at the silica/aqueous solution interface, providing insights into charge reorganization during the adsorption process.

The fundamental concepts of NONE for characterizing surface nonlinearity are described hereinabove. If the nonlinear beam from the surface is passed through a quarter wave plate, a half-wave plate, and a polarizer in series as depicted in FIG. 1, the detected field is given by the following equation.

$$e^{2\omega}_{PMT\#1} = N \begin{bmatrix} 0 & 0 \\ \sin(2\Delta^{2\omega}) + i\sin(2\alpha^{2\omega}_H) & \cos(2\Delta^{2\omega}) + i\cos(2\alpha^{2\omega}_H) \end{bmatrix} \begin{bmatrix} e^{2\omega}_p \\ e^{2\omega}_s \end{bmatrix}. \quad (25)$$

In Eq. 25, $\Delta^{2\omega} = \alpha^{2\omega}_H - \alpha^{2\omega}_Q$ and N is a constant proportional to the surface number density of SHG-active chromophores (assuming identical non-interacting chromophores). For an appropriate combination of $\alpha^{2\omega}_H$ and $\alpha^{2\omega}_Q$, the detected SHG intensity from the initial background response (species A) can be suppressed at the first photomultiplier tube (PMT) 56 (and correspondingly maximized at the second PMT 57), such that $|e^{2\omega,A}_{PMT\#1}|=0$. Introduction of a new source of nonlinear polarization (species B) yields a net polarization from the interface given by the coherent linear combination of the two fields.

$$e^{2\omega}_{PMT\#1} = (N_A e^{2\omega,A}_p + N_B e^{2\omega,B}_p)[\cos(2\Delta^{2\omega}) - i\cos(2\alpha^{2\omega}_H)] + (N_A e^{2\omega,A}_s + N_B e^{2\omega,B}_s)[\sin(2\Delta^{2\omega}) - i\sin(2\alpha^{2\omega}_H)] \quad (26)$$

For a selection of $\alpha_H$ and $\alpha_Q$ producing zero intensity at PMT 56 from species A alone, the detected field simplifies to a function solely dependent on the nonlinear optical properties of species B.

$$e^{2\omega}_{PMT\#1} = N_B \begin{Bmatrix} e^{2\omega,B}_p [\cos(2\Delta^{2\omega,A}) + i\cos(2\alpha^{2\omega,A}_H)] + \\ e^{2\omega,B}_s [\sin(2\Delta^{2\omega,A}) - i\sin(2\alpha^{2\omega,A}_H)] \end{Bmatrix} \quad (27)$$

In Eq. 27, the superscripts indicate the NONE ellipsometric angles yielding null signals at PMT 56 for species A alone (or more generally, the initial background SHG response). It is important to note that a distinction is made between NONE measurements (which are measurements of the QWP and HWP rotation angles producing intensity minima) and NONE-SI measurements (which are measurements of intensity acquired after first performing a NONE minimization). Using this simple and general polarization selection approach, the detected intensity becomes independent of the number density of species A and scales quadratically with the number density of species B.

$$I^{2\omega}_{PMT\#1} \propto N_B^2 |e^{2\omega}_{PMT\#1}|^2 \quad (28)$$

6. EXAMPLE 2

The SHG measurements for Example 2 were carried out in a total internal reflection cell 28 using a fused silica right-angle prism 30 (ESCO Products, S1-UV, available from ESCO Products, 171 Oak Ridge Road, Oak Ridge, N.J. 07438). The solutions were introduced to the surface through the aperture 38. Prior to each use, the prism 30 was immersed in a bath of chromic acid for 10 minutes, rinsed with ultra pure water, and dried under a stream of nitrogen. Rhodamine 6G (R6G, Aldrich, ~95% pure, available from Sigma-Aldrich Chemical Co., Milwaukee, Wis.) was used without purification and was solvated in high purity water (resistivity of >17.5 MΩcm). In each set of kinetics measurements, two solutions were prepared, one with R6G and the other with 2bovine serum albumin (BSA, Mallinckrodt ~99.5% pure, available from Mallinckrodt Baker, Inc., Red School Lane, Phillipsburg, N.J.) and an identical concentration of R6G.

A schematic of the instrument is shown in FIG. 1 and described in detail hereinabove. In brief, radiation from an Nd:YAG laser 12 (1064 nm, 5–7 ns pulses) was focused onto the surface (~1 mJ per pulse). The incident beam was prepared in a given polarization state by an appropriate combination of half wave plate 16 and quarter wave plate 22 rotation angles, as shown in FIG. 1. After being generated at the total internal reflection interface, the second harmonic beam was passed through a second set of quarter wave plate 46 and half wave plate 48, a polarizing beam-splitting cube (PBC) 50, and appropriate spectral and spatial filters prior to detection using a photomultiplier tube 56,57.

Polarization analysis of the SHG from both the aqueous R6G/fused silica interface (R6G/silica) and the interface between fused silica and an aqueous solution containing both R6G and BSA (BSA/R6G/silica) was performed using the nonlinear optical ellipsometric approach described herein. In a given NONE polarization measurement, the SHG intensity detected at PMT 56 was minimized by iterative rotation of the QWP 46 and the HWP 48 along the exigent beam path. NONE polarization data were acquired with the QWP 22 along the incident beam path fixed at $\alpha_Q^\omega = -45°$ and for HWP 20 rotation angles of $\alpha_H^\omega = -22.5°$, 0°, 22.5°, and 45°, corresponding to linearly polarized light oriented at −45°, right circularly polarized light, linearly polarized light oriented at +45°, and left circularly polarized light, respectively. The intensity minima determined from the NONE measurements for each incident polarization state (four separate measurements for each) were used to determine the complex parameter $\rho$, equal to the ratio of $e_p^{2\omega}/e_s^{2\omega}$ using equation 17.

NONE polarization measurements were acquired for the R6G aqueous solution/fused silica interface prior to introduction of BSA and after ~1 hr of exposure of the surface to BSA. The NONE intensity minima were always at least a factor of 40 smaller than the intensity maxima (simultaneously recorded on PMT 57).

In a given kinetics experiment, a solution of 0.41 mM R6G was introduced to the surface. The second harmonic response measured by PMT 56 was subsequently minimized by iteratively rotating the QWP 46 and HWP 48 along the detection pathway. The solution containing $2 \times 10^{-5}$ M BSA (also 0.41 mM R6G) was subsequently introduced through the flow cell 28, and the second harmonic response was monitored from 5 minutes prior to injection up to 5 hours after injection. When recording the long-time kinetics (>15 min.), the laser 12 repetition rate was reduced from 20 Hz to 2 Hz. The raw data were normalized using the intensity of the SHG beam detected at PMT 57 from the R6G solution/fused silica interface as an internal reference.

NONE polarization measurements were performed to determine the complete polarization state of the nonlinear beam before and after adsorption of BSA, the results of which are summarized in Table 5.

Values in parentheses indicate one standard deviation from 4 separate measurements. The incident QWP was fixed at $\alpha_Q^\omega = -45°$ for all reported values.

The retention of phase information by null ellipsometric polarization characterization provides substantially greater information content than comparable prior art intensity-based polarization analysis approaches, particularly in resonant or near resonant measurements such as these. The experimentally acquired $\rho$ values summarized in Table 5 were combined using the procedure described hereinbelow (under x. Supporting Calculations) to yield a full suite of complex-valued effective tensor elements, describing the nonlinear optical responses of the surfaces. In turn, these effective $\chi^{(2)}$ tensor elements (compiled in Table 6) were used to predict the complete polarization state of the exigent SHG beam, including full phase information, for any arbitrary input polarization.

TABLE 6

Summary of Effective $\chi^{(2)}$ Tensor Elements Measured from the NONE Polarization Analysis.

| | $\chi_{ssp}$ | $\chi_{pss}$ | $\chi_{ppp}$ | $\chi_{spp}$* | $\chi_{psp}$* |
|---|---|---|---|---|---|
| R6G/Silica | 1 | −0.17 (±0.03) + 0.08i (±0.01i) | 0.44 (±0.03) + 0.34i (±0.01i) | −0.06 (±0.06) + 0.02i (±0.01i) | −0.01 (±0.05) − 0.02i (±0.05i) |
| BSA/R6G/Silica | 1 | −0.12 (±0.02) + 0.107i (±0.005i) | 0.40 (±0.02) + 0.37i (±0.04i) | −0.16 (±0.05) − 0.19i (±0.01i) | 0.07 (±0.03) − 0.06i (±0.03i) |

*Asterisk indicates effective tensor elements that are only expected to be nonzero in chiral films.

Figure 4:
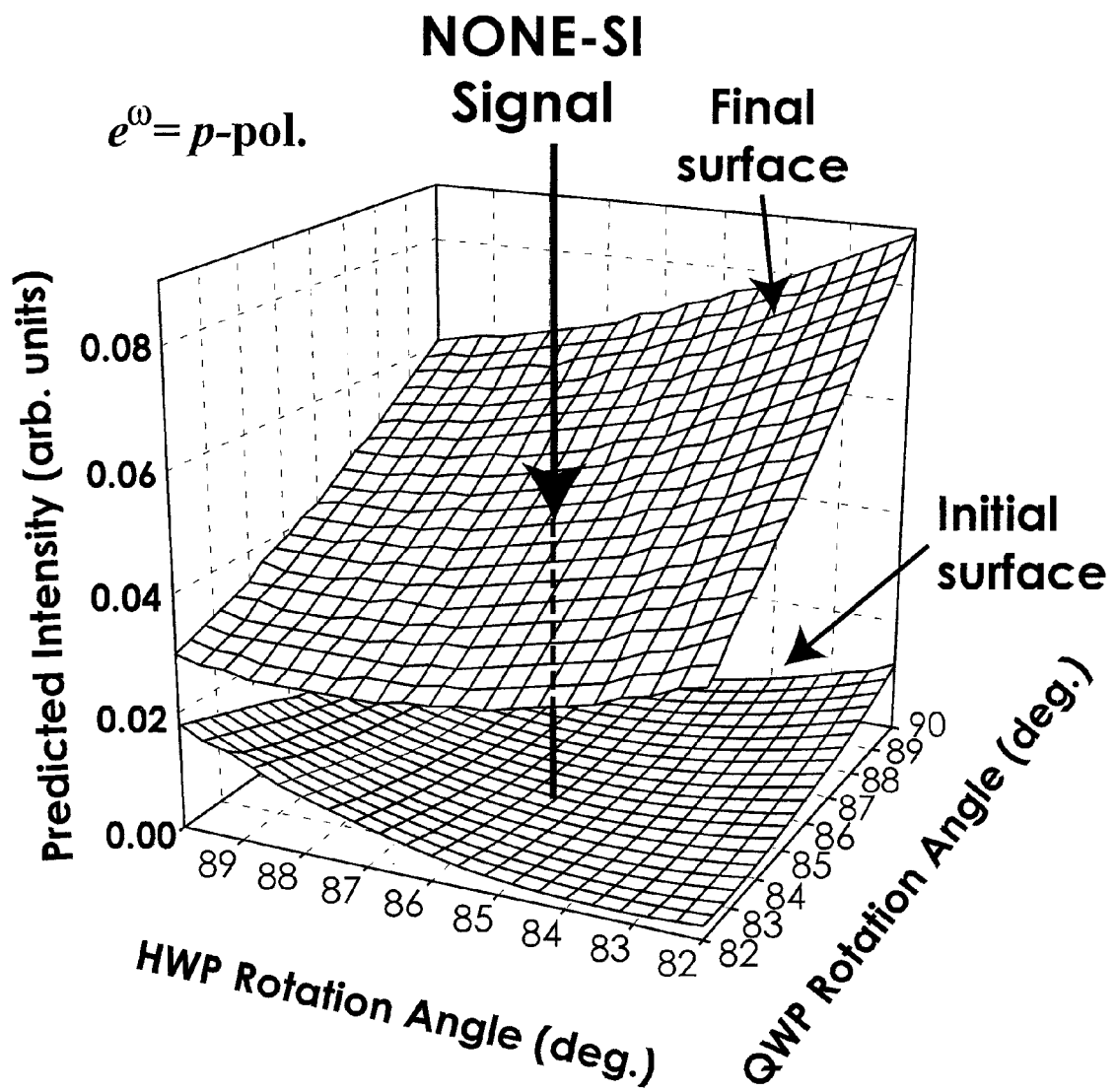
FIG. 4 illustrates calculated intensities of the detected SHG beams as functions of the exigent quarter and half wave plate rotation angles for a p-polarized incident beam using the methodology of the present invention.
Figure 5:
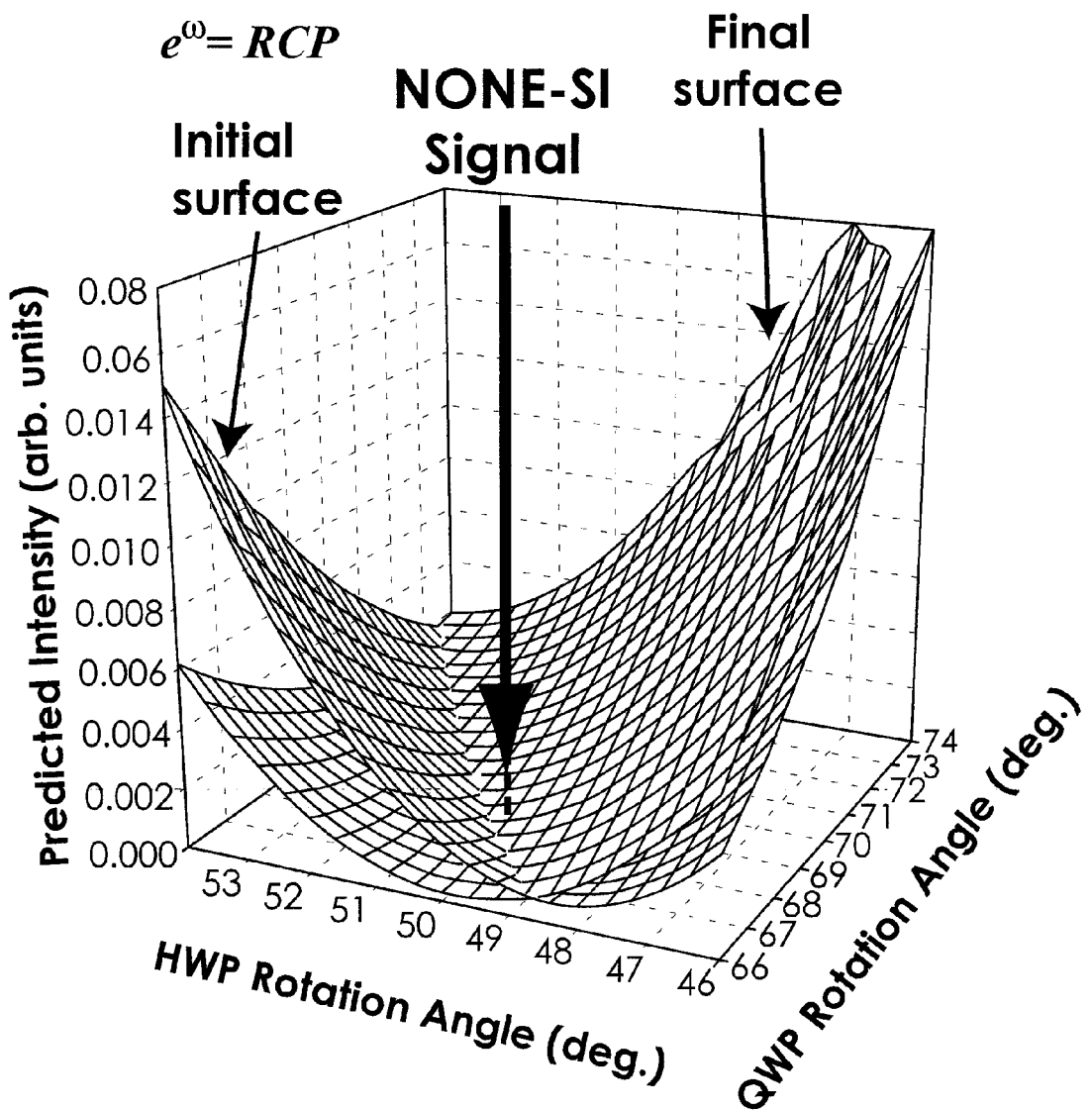
FIG. 5 illustrates calculated intensities of the detected SHG beams as functions of the exigent quarter and half wave plate rotation angles for a right circularly polarized (RCP) incident beam using the methodology of the present invention.

Using Equations 25 through 28, the predicted intensity of the detected SHG as a function of the rotation angles of the QWP 46 and HWP 48 positioned along the detection pathway were reconstructed for both p-polarized and right circularly polarized incident beams (FIGS. 4 and 5, respectively) with no adjustable parameters. FIG. 4 illustrates calculated intensities of the detected SHG beams as functions of the exigent quarter and half wave plate rotation angles for a p-polarized incident beam. FIG. 5 illustrates calculated intensities of the detected SHG beams as functions of the exigent quarter and half wave plate rotation angles for a right circularly polarized (RCP) incident beam. In FIGS. 4 and 5, the detected NONE-SI intensity corresponds to the intensity difference in between the two surfaces at the minimum of the initial surface, and "Initial" and "Final" refer to the R6G/silica and BSA/R6G/silica interfaces, respectively. The curves shown in FIGS. 4 and 5 are predicted intensity responses derived solely from the experimentally mea-

TABLE 5

Results of the Experimental NONE Polarization Analysis.

| | | $\alpha_H^\omega = -22.5°$ (−45°) | $\alpha_H^\omega = 22.5°$ (45°) | $\alpha_H^\omega = 0°$ (RCP) | $\alpha_H^\omega = 45°$ (LCP) |
|---|---|---|---|---|---|
| R6G/Silica | $\alpha_Q^{2\omega}$ | 71° (±3°) | 17° (±1°) | 71° (±2°) | 114° (±4°) |
| | $\alpha_H^{2\omega}$ | 25° (±2°) | 43° (±1°) | 51° (±2°) | 43.4° (±0.8°) |
| | $\rho$ | 0.28 (±0.09) + 0.42i (±0.07i) | −0.25 (±0.03) − 0.42i (±0.04i) | 0.21 (±0.03) − 0.63i (±0.05i) | −0.31 (±0.02) + 0.59i (±0.07i) |
| BSA/R6G/Silica | $\alpha_Q^{2\omega}$ | 62.8° (±8°) | 107° (±1°) | 61° (±1°) | 14° (±2°) |
| | $\alpha_H^{2\omega}$ | 21° (±1°) | 64° (±2°) | 47° (±2°) | 61° (±1°) |
| | $\rho$ | 0.43 (±0.03) + 0.45i (±0.02i) | −0.25 (±0.05) − 0.41i (±0.04i) | 0.29 (±0.02) − 0.74i (±0.08i) | −0.22 (±0.05) + 0.36i (±0.04i) | sured null angles summarized in Table 5. Separate intensity surfaces were generated from the NONE polarization data acquired prior to and following addition of BSA. The axes in FIGS. 4 and 5 were chosen to selectively highlight the angle window around the intensity minima for the initial R6G/silica interface (i.e., the null angles expected prior to introduction of BSA).

Inspection of the calculated intensity-dependent responses shown in FIGS. 4 and 5 provides a convenient graphical depiction of the origin of the detected NONE-SI intensity. Upon introduction of BSA, the polarization state of the nonlinear beam changes, and the QWP and HWP rotation angles yielding intensity minima correspondingly change. The detected signals in the NONE-SI experiments are predicted to scale with the difference between the polarization-dependent relative intensity obtained before and after introduction of BSA (indicated by the solid vertical lines in the figures).

Figure 6:
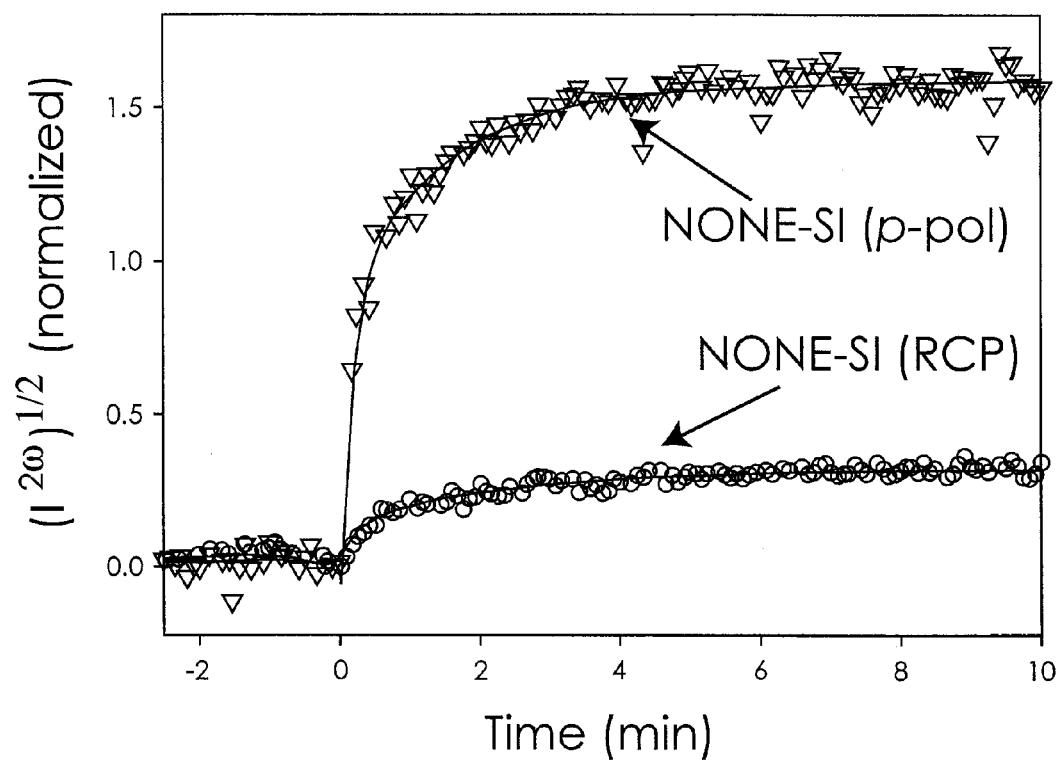
FIG. 6 is a graph illustrating the normalized second harmonic responses using the methodology of the present invention for the first 10 minutes after BSA injection from p-polarized and RCP incident light (triangles and open circles, respectively).
Figure 7:
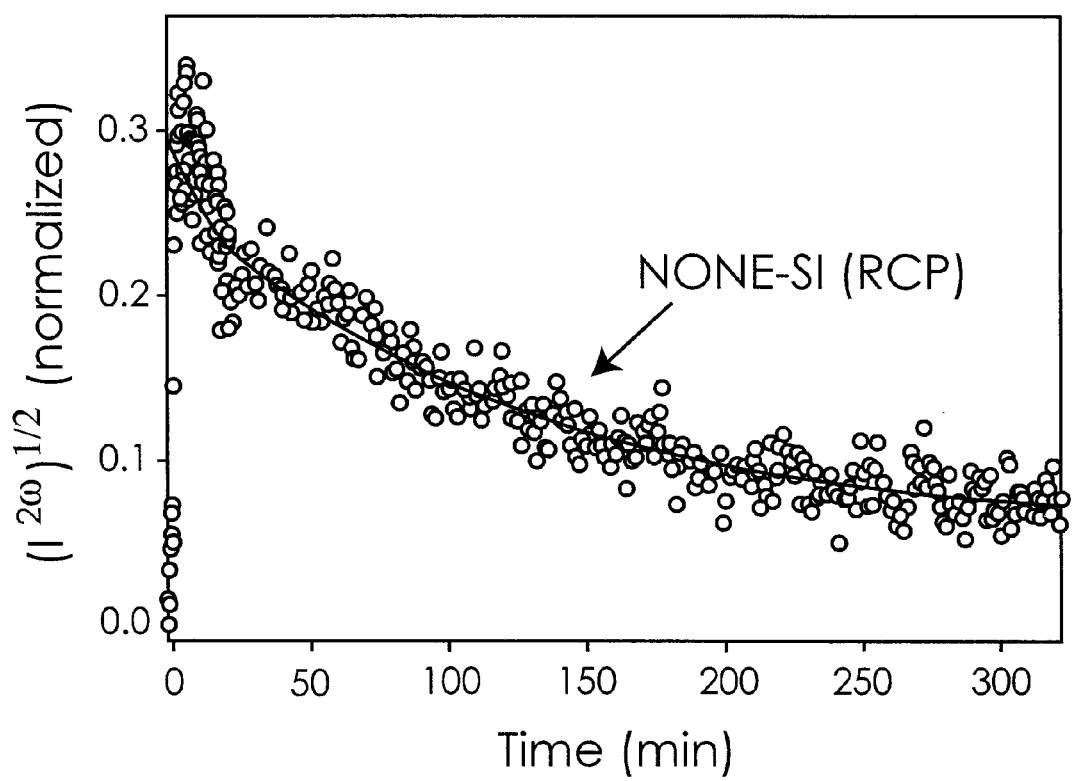
FIG. 7 is a graph illustrating the slow time kinetics of BSA binding to glass in the experiment of FIG. 6.

Time-dependent kinetics measurements acquired using the NONE-SI method are shown in FIGS. 6 and 7 upon exposure of the fused silica surface of prism 30 to an aqueous solution containing BSA. Upon introduction of the R6G-BSA solution (time zero), an increase in the measured SHG intensity along both channels was observed. This signal continued to increase rapidly for approximately 4 minutes (FIG. 6) before transitioning to a slower decay process that continued for several hours (FIG. 7). The solid lines in FIGS. 6 and 7 are fits of the data to exponential rises to maxima or exponential decays, where appropriate. The NONE-SI (RCP) fit of FIG. 6 yielded time constant of $4\pm 1$ $\min^{-1}$. The NONE-SI (p-polarized) fit of FIG. 6 yielded a time constant of $5\pm 1$ $\min^{-1}$. The fit of FIG. 7 yielded a time constant of $7.9\times 10^{-3}\pm 0.5\times 10^{-3}$ $\min^{-1}$.

These trends were reproducible for multiple trails acquired over several days. NONE-SI data were acquired for both right circularly polarized incident light and for p-polarized incident light. In the case of a p-polarized incident beam, a null was obtained for an s-polarized second harmonic beam for the aqueous R6G/glass interface, consistent with expectations for an achiral surface. In uniaxially oriented systems, this latter polarization combination (indicated by $I_{sp}$) only yields nonzero intensity if the chiral tensor element $x_{XYZ}$ is nonzero.[34-37] These chiral-specific NONE-SI kinetics measurements indicate a time-dependent increase in SHG-active surface chirality upon exposure to aqueous BSA solutions that mirrors the NONE-SI kinetics responses (also in FIG. 6) acquired with circularly polarized incident light.

In order to assist in interpreting the kinetics measurements shown in FIGS. 6 and 7, it is helpful to develop a physical model for the origin of the change in the polarization state of the SHG beam upon exposure of the surface to BSA. Several possible mechanisms may be present. For example, BSA itself may be generating SHG with unique polarization characteristics. Certainly, several groups have reported the observations of substantial native SHG from oriented protein assemblies. However, surfaces exposed to BSA alone yielded no detectable SHG under these experimental conditions. Alternatively, previous nonlinear optical studies by Salafsky and Eisenthal (cited hereinabove) have demonstrated that surface binding of protein can substantially alter the surface charge characteristics, which in turn may influence the nonlinear polarization detected using both NONE and NONE-SI. However, this mechanism alone cannot adequately explain the observed increase in the chiral-specific SHG response upon protein binding shown in FIG. 6. An alternative and much simpler explanation is that the change in nonlinear polarization arises from rhodamine closely associated with surface-bound protein. It has recently been demonstrated that BSA can act as a chiral template to generate a substantial macroscopic chiral response in SHG arising from chiral orientation of achiral chromophores. Analogous to the chirality present in a propeller comprised of chiral "blades", chirality within the chromophore is not required in order to generate significant chiroptical effects in the macromolecular surface ensemble. Quantitatively, the macroscopic chiral response from a uniaxially oriented assembly of chromophores of $C_{2v}$ symmetry (or quasi-$C_{2v}$ symmetry as in R6G) is given by the following expression.

$$x_{XYZ}=x_{XZY}=-x_{YXZ}=-x_{YZX}=\tfrac{1}{2}N_s\langle\sin^2\theta\sin\psi\cos\psi\rangle(\beta_{x'x'z'}-\beta_{z'x'x'}) \qquad (29)$$

Figures 8A, 8B, 8C:
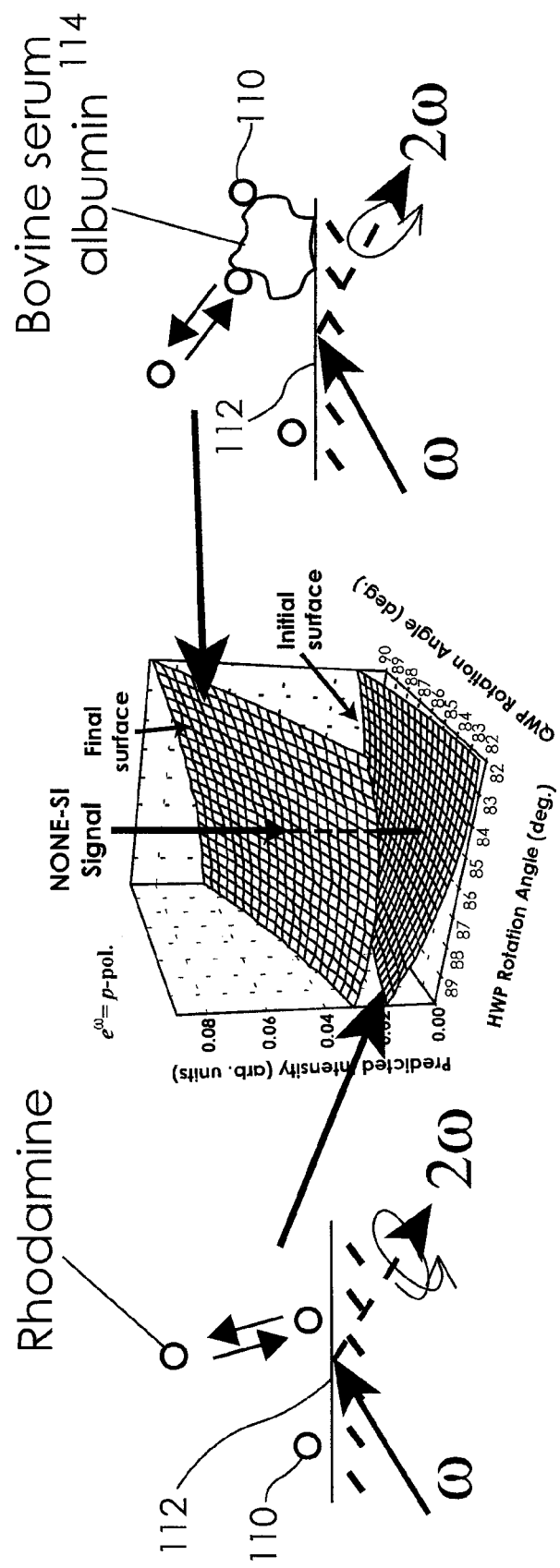
FIG. 8a is a schematic diagram of the SHG response of unbound rhodamine.
FIG. 8b is a copy of the graph of FIG. 4.
FIG. 8c is a schematic diagram of the SHG response of rhodamine closely associated with surface-bound BSA.
Figure 9A:
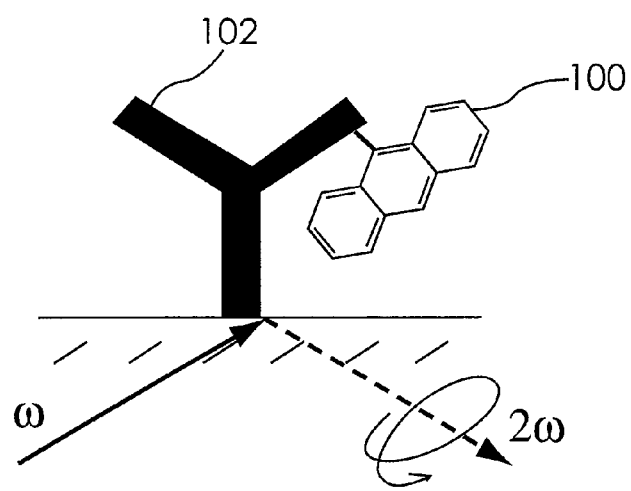
FIGS. 9a and 9b schematically illustrate that the NONE-SI methodology of the present invention can be adapted for measuring specific binding interactions of unlabeled proteins in real time from binding-induced changes in the orientation of an SHG-labeled receptor protein.
Figure 9B:
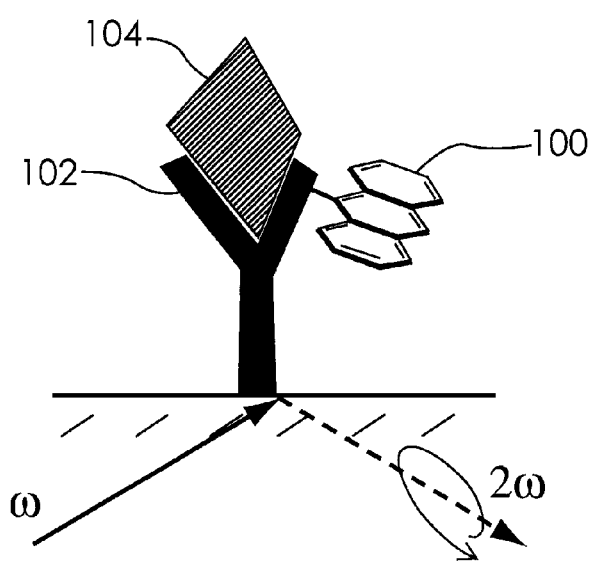

Under the resonant conditions used in these investigations, the $\beta_{x'x'z'}$ tensor element dominates the molecular hyperpolarizability. As illustrated in FIGS. 8a–c, assuming that the molecular hyperpolarizability tensor $\beta_{ijk}$ for R6G is similar when bound to the surface versus associated with BSA, the greatest difference between species A (R6G 110 at the bare glass/solution interface 112, FIG. 8a, represented by the lower (initial) surface of FIG. 8b (which is identical to FIG. 4)) and species B (R6G associated with BSA 114 at the glass/solution interface 112, FIG. 8c, represented by the upper (final) surface of FIG. 8b) is the concomitant change in orientation upon interaction with surface-bound BSA. Since the primary biological functions of BSA are the regulation of osmotic pressure and the binding and ion transport, it is reasonable to suggest the presence of weak but significant interactions between BSA and the charge sites of R6G. Different orientation distributions for the dye molecules are generally expected to produce significantly different nonlinear polarizations. This mechanism is consistent with recent molecular modeling calculations demonstrating that orientational effects such as described by Eq. 29 appear to be the dominant origin of the remarkable sensitivity of SHG to chirality in thin films and interfaces.

Inspection of both the calculated NONE-SI intensities in FIGS. 4 and 5 and the experimental kinetics measurements in FIG. 6 clearly indicate that the magnitude of the NONE-SI response can change significantly when acquired for different polarization states of the incident beam. Using just the NONE polarization measurements compiled in Table 5, the normalized NONE-SI intensities for incident beams of right circularly polarized light compared with p-polarized light are predicted to differ by a factor of 26 (corresponding to a 5.1-fold difference in amplitude). Experimentally, analysis of the data in FIG. 6 indicates that the two incident polarization states yield SHG signals that differ by a factor of $5.0\pm 0.3$ (averaged from 61 data points acquired between 5 and 10 minutes), in remarkably good agreement with the theoretical predictions based solely on the measured QWP and HWP rotation angles compiled in Table 5.

The significantly greater sensitivity observed using NONE-SI with a p-polarized incident beam is likely due to the fact that this polarization combination (i.e., s-polarized SHG for a p-polarized fundamental beam) selectively probes the chiral-specific SHG response in uniaxial systems. Upon exposure to BSA, the surface transitions from achiral to chiral. Consequently, the chiral $x^{(2)}$ tensor elements $x_{XYZ}=x_{XZY}=-x_{YXZ}=-x_{YZX}$ are zero-valued initially and nonzero after exposure to BSA. The substantial differences in SHG intensity observed using a chiral-specific polarization combination are consistent with this simple physical model.

Irrespective of the specific molecular interactions, the NONE-SI method recovers a simple quadratic scaling behavior between the detected intensity and the number of local perturbations induced by the surface adsorption of BSA. By comparison, this quadratic relationship is not generally maintained in prior art SHG measurements arising from the interference of multiple nonlinear sources. In the absence of this background suppression, the intensity can either increase or decrease with increasing analyte number density, with the scaling behavior ranging between linear and quadratic depending on the relative magnitude and phase angle φ of the signal and background. For example, the intensity detected by PMT 57 $I^{2\omega}_{PMT\#2}$ during the kinetics measurements (not shown) contains contributions from both the native surface (species A) and from R6G closely associated with surface-immobilized BSA (species B) as seen below.

$$I_{PMT\#2}^{2\omega} \propto N_A^2 |e^{2\omega,A}|^2 + N_B^2 |e^{2\omega,B}|^2 + 2N_A N_B |e^{2\omega,A}| |e^{2\omega,B}| \cos\phi \quad (30)$$

In general, the scaling behavior of the detected intensity with surface concentration cannot be unambiguously identified in the presence of a significant background response unless the relative phase angle φ is known a priori. If both nonlinear responses arise from different orientation distributions of the same chromophore (as in this Example 2), φ can be expected to be close to either 0 or π (positive or negative interference), leading to scaling that is linear with the surface concentration at low coverage (in which case the $2N_A N_B |e^{2\omega,A}| |e^{2\omega,B}| \cos\phi$ term dominates) and approaches quadratic behavior at higher surface coverages (for which $N_B^2 |e^{2\omega,B}|^2$ dominates). By removal of the background response, the intensity detected by PMT 56 using the NONE-SI method recovers a simple quadratic scaling behavior with the surface concentration of species B, irrespective of both the phase angle φ and the amplitude of the response from species A.

The kinetic data acquired by the NONE-SI method reveal some interesting trends when compared with previous measurements of BSA binding kinetics at glass/aqueous solution interfaces. Prior art publications have identified at least two distinct kinetic regimes for BSA adsorption to glass. The initial rapid adsorption occurs on the scale of seconds to minutes. Then a slower adsorption process occurs over several hours, which has been attributed in the prior art to slow reorganization to a more stable surface conformation that minimizes electrostatic repulsions. Based on these prior art studies, the amount of BSA at the surface is increasing during the long-time kinetic process shown in FIG. 7. However, the detected SHG intensity demonstrated hereinabove is decreasing, which can be attributed to changes in the availability of the charge sites able to bind R6G during the slow protein reorganization. This slow restructuring is particularly important physiologically. Serum albumins are among the most prolific proteins within the body and are among the first proteins to bind to the surfaces of medical implants. A layer of surface-bound serum albumin in its native conformational state can produce a surface with high biocompatibility. In contrast, a surface coating of denatured serum albumin can substantially change the cellular response. By nature of this bimodal behavior, the biocompatability of implanted devices depends critically on the nature of the serum albumin-surface interactions. The overall loss of SHG with time in the long-time kinetic regime shown in FIG. 7 indicates a reduction in the number and/or structural order of the cation binding sites, providing strong evidence supporting the denaturation of the protein at the interface. By comparison, prior art binding measurement techniques of unlabeled proteins such as SPR and ellipsometry only provide information on the average density of surface protein and are largely blind to protein conformation and activity.

In the present Example 2, weak interactions between the surface and a nonlinear optical probe molecule in dynamic equilibrium were used for monitoring nonspecific protein adsorption at a dielectric interface. However, the generality of NONE-SI extends well beyond selectively probing the emergence of surface chirality using the $I_{sp}$ polarization combination. All that is required for generation of a detected response in NONE-SI is a change in the surface nonlinear polarization (e.g., from changes in the orientation distribution and/or changes in the molecular hyperpolarizability), and the scope of the present invention is intended to include all such detection methodologies. As one example, a strategy for implementing NONE-SI for selective measurements of specific protein—protein binding interactions is shown schematically in FIGS. 8a and 8b. The initial surface (FIG. 8a) consists of an SHG-active probe molecule 100 bound to a surface-immobilized receptor protein 102. Irrespective of the initial nonlinear polarizability of the interface, an appropriate combination of wave plates can be found to completely suppress the SHG response detected at PMT 56. Binding of the analyte protein 104 will generally result in a change in the orientation distribution of the SHG-active label (FIG. 8b), with a corresponding change in the nonlinear polarization. This change in turn will result in incomplete rejection of the SHG by the wave plates and a detected intensity that scales quadratically with the number of binding events. Consequently, the same basic NONE-SI strategy employed in the nonspecific binding example described herein should be equally applicable in label-free real-time measurements of specific protein—protein binding interactions.

The remarkable sensitivity of the nonlinear polarization to subtle changes in surface structure and orientation suggests that NONE-SI is applicable for background suppression and signal isolation in virtually all nonlinear optical techniques, including sum-frequency generation (SFG), coherent anti-Stokes Raman (CARS) spectroscopies, and degenerate four wave mixing (D4WM).

7. NONE MODELS FOR CHIRAL FILMS

Relating the incident and exigent fields to the fields at the interface using Fresnel factors is a crucial step in developing and comparing different thin film optical models for SHG and SFG polarization measurement. The Fresnel factors derived in the present application (Model A) differ from more widely used expressions derived previously by Heinz and Shen and coworkers and by Mizrahi and Sipe (Model B), described in detail in the Supporting Calculations described hereinbelow. From inspection of FIG. 2, the expressions for the linear Fresnel factors can be written using a methodology modeled after treatments of traditional ellipsometry measurements of thin films.

$$L_{XX}^{\omega,A} = \frac{t_{p13}^{\omega}}{1 - r_{p32}^{\omega} r_{p31}^{\omega} e^{-2i\beta^{\omega}}} \left(1 - r_{p32}^{\omega} e^{-i\beta^{\omega}}\right) \quad (31a)$$

$$L_{YY}^{\omega,A} = \frac{t_{s13}^{\omega}}{1 - r_{s32}^{\omega} r_{s31}^{\omega} e^{-2i\beta^{\omega}}} \left(1 + r_{s32}^{\omega} e^{-i\beta^{\omega}}\right) \quad (31b)$$

$$L_{ZZ}^{\omega,A} = \frac{t_{p13}^{\omega}}{1 - r_{p32}^{\omega} r_{p31}^{\omega} e^{-2i\beta^{\omega}}} \left(1 + r_{p32}^{\omega} e^{-i\beta^{\omega}}\right) \quad (31c)$$

In Eq. 31, $L^{\omega,A}$ is a diagonal matrix of Fresnel factors relating the field components within the interfacial layer to the components in the incident beam, r and t are amplitude reflection and transmission coefficients, respectively, with the subscripts s and p referring to the polarization state with respect to the plane of reflectance, and $\beta^{\omega}$ is the phase thickness of the interfacial film (given explicitly in the Supporting Calculations hereinbelow). The Fresnel factors describing the frequency doubled light detected in the far-field can be derived using an analogous approach, described in detail in the Supporting Calculations hereinbelow.

$$L_{XX}^{2\omega,A} = \frac{t_{p31}^{2\omega}}{1 - r_{p31}^{2\omega} r_{p32}^{2\omega} e^{-2i\beta^{2\omega}}} \left(1 - r_{p32}^{2\omega} e^{-i\beta^{2\omega}}\right) \quad (32a)$$

$$L_{YY}^{2\omega,A} = \frac{t_{p31}^{2\omega}}{1 - r_{s31}^{2\omega} r_{s32}^{2\omega} e^{-2i\beta^{2\omega}}} \left(1 + r_{s32}^{2\omega} e^{-i\beta^{2\omega}}\right) \quad (32b)$$

$$L_{ZZ}^{2\omega,A} = \frac{t_{p31}^{2\omega}}{1 - r_{p31}^{2\omega} r_{p32}^{2\omega} e^{-2i\beta^{2\omega}}} \left(1 + r_{p32}^{2\omega} e^{-i\beta^{2\omega}}\right) \quad (32c)$$

These same equations hold for measurements acquired in total internal reflection, in which case the reflection and transmission angles and coefficients are necessarily complex valued. These expressions are valid for ultrathin films (for which $\beta^\omega \cong \beta^{2\omega} \cong 0$) as well as for films in which the thickness approaches or exceeds the wavelength of light.

The description for propagation of the nonlinear beam within the interfacial layer described in Eq. 32 is virtually identical to expressions use to treat light propagation within planar optical waveguides. If $\beta = \pi$ and if the magnitude of the interfacial refractive index is large enough for total internal reflection, the transmission coefficients become purely complex-valued (non-propagating) and the mathematical formalism in Eq. 32 reduces to that of a single-mode planar waveguide. If $\beta << \pi$ as is expected in the overwhelming majority of surface SHG and SFG experiments, the mathematics describes a lossy waveguide, resulting in short propagation distances within the interfacial layer and significant losses manifested as optical emission in both reflection and transmission.

Within a waveguide, it is well known that the propagating component of the beam traveling within the thin surface film contains refractive index contributions from both the substrate and superstrate weighted by an exponential decay (i.e., the evanescent field). In attenuated total internal reflection absorbance measurements, this evanescent contribution to the effective refractive index sampled by the beam allows measurement of the imaginary component of the refractive index within the evanescent medium as a function of wavelength (i.e., the absorbance spectrum). In SHG and SFG, a general mathematical treatment for describing the effective refractive index within the interfacial layer can be written to include contributions from the substrate and ambient medium by explicitly considering the vertical profile of the wavefunction u describing the component of the nonlinear optical light propagating within the interfacial layer. From the wavefunction u, the expectation value for the effective refractive index can be calculated directly.

$$\langle n_{3,\mathit{eff}} \rangle = \frac{\int_{-\infty}^{\infty} u^*(z) n(z) u(z) \, dz}{\int_{-\infty}^{\infty} u^*(z) u(z) \, dz} \quad (33)$$

In Eq. 33, $n_{3,\mathit{eff}}$ is a tensor describing the effective refractive index of the interfacial layer, n(z) is the spatially-varying tensor describing the refractive index across the interfacial region, and z is the vertical axis paralleling the surface normal with z=0 defined to be the center of the nonlinear optically active interfacial layer. The surface is assumed to be effectively infinite and uniform in the x and y directions within the surface plane. Using established methods for treating guided wave-optics, u(z) can be separated into the portion of the wavefunction propagating within the interfacial layer (internal) and contributions from the evanescent field (external). The evanescent field decays exponentially into the ambient medium and the substrate with extinction coefficients $\gamma_1$ and $\gamma_2$, respectively, allowing the effective refractive index tensor to be written in the following form.

$$\langle n_{3,\mathit{eff}} \rangle = \frac{\int_{-\infty}^{-d/2} n_2 e^{\gamma_2 z} dz + \int_{-d/2}^{d/2} u_{int}^*(z) u_{int}(z) n_3(z) dz + \int_{d/2}^{\infty} n_1 e^{-\gamma_1 z} dz}{\int_{-\infty}^{-d/2} e^{\gamma_2 z} dz + \int_{-d/2}^{d/2} u_{int}^*(z) u_{int}(z) dz + \int_{d/2}^{\infty} e^{-\gamma_1 z} dz} \quad (34)$$

The presence of the exponential decaying portion of the optical wavefunction into the substrate and superstrate is a natural consequence of the required continuity of the amplitude and slope of the wavefunction across the interfacial layer. For a film with a thickness d much less than the wavelength of light, the portion of the wavefunction describing the beam propagating internally within the interfacial layer $u_{int}(z)$ can be reasonably approximated as being constant across the film with an average amplitude of $u_{int}(z) \cong \frac{1}{2}(e^{-\gamma_2 d/2} + e^{-\gamma_1 d/2}) \cong 1$. Within the validity of this thin-film assumption, a relatively simple expression can be written for the effective interfacial refractive index.

$$\langle n_{3,\mathit{eff}} \rangle = \frac{n_1 e^{-\gamma_1 d/2}/\gamma_1 + n_2 e^{-\gamma_2 d/2}/\gamma_2 + d\langle n_3 \rangle}{e^{-\gamma_1 d/2}/\gamma_1 + e^{-\gamma_2 d/2}/\gamma_2 + d} \quad (35)$$

Several different models for treating the interfacial optical constants in SHG and SFG can be conveniently expressed within this one mathematical formalism by considering different limiting cases for the values of the decay lengths $1/\gamma$. Two important limiting cases will be considered explicitly; (1) for $1/\gamma << d$ (i.e., rapid decay in the wavefunction upon exiting the interfacial layer relative to the film thickness), consistent with the majority of previous theoretical models, and (2) for $1/\gamma \cong \lambda_0 >> d$ (i.e., for an exponential decay length comparable to the wavelength of light in vacuum $\lambda_0$ and a film thickness much less than the wavelength of light).

Case 1: $1/\gamma << d$

In the limiting case of $1/\gamma << d$, the effective refractive index for the interfacial layer is simply the average refractive index within the monolayer or multilayer film, recovering expressions similar to those currently used widely to interpret polarization phenomena in SHG and SFG surface measurements.

$$\langle n_{3,\mathit{eff}} \rangle \cong \langle n_3 \rangle \quad (36)$$

The tensor properties of the refractive index are implicitly retained in Eq. 36. The orientational ordering required for symmetry breaking and observation of SHG and SFG implies the presence of birefringence within the interfacial film. Therefore, within the validity of Case 1, the refractive index will generally differ for light polarized normal to the surface compared to polarizations parallel to the surface plane. In uniaxial thin films exhibiting resonance-enhancement at either an incident or exigent frequency, these elements of the refractive index tensor will also generally contain significant (and perhaps dominant) imaginary contributions, which are also expected to be sensitive functions of molecular orientation. Consequently, within the validity of Case 1, accurate determination of the $x^{(2)}$ tensor elements from macroscopic polarization measurements is nontrivial under the best circumstances and prohibitively complex under the worst due to the many nonzero and often unknown components of the tensor describing the interfacial refractive index.

Case 2: $1/\gamma \cong \lambda_0 \gg d$

In this limiting case, the collective contributions to the macroscopic polarization detected in the far field arising from emission over an nonlinear source polarization effectively extending over several hundred nanometers across the interface becomes mathematically equivalent to simply using a three-level model with the interfacial refractive index tensor given by a weighted average of the ambient, film, and substrate refractive indices. Evaluation of Eq. 34 in the limit of $1/\gamma_1$, $1/\gamma_2 \gg d$ yields the following expression.

$$\langle n_{3,\mathit{eff}} \rangle \cong \frac{n_1/\gamma_1 + n_2/\gamma_2 + d\langle n_3 \rangle}{1/\gamma_1 + 1/\gamma_2 + d} \quad (37)$$

From standard optical treatments of exponential decay lengths in total internal reflection, the two extinction coefficients $\gamma_1$ and $\gamma_2$ are related to the refractive indices inside and outside the layer according to the following relationship.

$$\gamma_j = \frac{2\pi}{\lambda_0} g_j; \; g_j \equiv \sqrt{n_3^2 \sin^2 \theta_3^{2\omega} - n_j^2} \quad (38)$$

Substitution results in a simple expression for the effective refractive index of the interfacial layer in the limit of a film thickness much less than the wavelength of light.

$$\langle n_{3,\mathit{eff}} \rangle \cong \frac{n_1/g_1 + n_2/g_2 + \langle n_3 \rangle (2\pi d/\lambda_0)}{1/g_1 + 1/g_2 + (2\pi d/\lambda_0)} \cong \frac{n_1 g_2 + n_2 g_1}{g_1 + g_2} \quad (39)$$

For a wide range of practical systems and measurement configurations, $g_1$ and $g_2$ will often be nearly equal, further reducing the expression for the effective refractive index to the simple average of the refractive indices of the two media sandwiching the interface.

$$\langle n_{3,\mathit{eff}} \rangle \cong \frac{n_1 + n_2}{2} \quad (40)$$

The proposed effective medium model described in Case 2 has several aesthetically appealing properties. Certainly, it is well established that the effective refractive index describing light propagating within an optical waveguide contains contributions from the external media out to distances on the order of the wavelength of light (i.e., the evanescent field). Indeed, this effect is essential for the success of attenuated total reflection absorption spectroscopy. There is also precedent suggesting that these bulk contributions continue to be significant even in lossy planar waveguides with a sub-wavelength thickness from the well-established success of surface plasmon resonance in local refractive index detection. In a film in which the thickness approaches or exceeds the wavelength of light, the general expressions given in Eq. 34 and Eq. 37 still apply (i.e., the thin film limit is not a necessary assumption). Furthermore, this mathematical approach is well behaved in the limit of vanishingly thin films, for which the limiting effective refractive index simply depends on the bulk optical properties of media 1 and 2. Finally, if neither the substrate nor the ambient medium exhibits birefrigence or strongly attenuates any of the incident or exigent beams, the effective interfacial refractive index will be expected to be purely real and scalar in the limit of an ultrathin film. In contrast to Case 1, the interfacial optical constants are often trivial to determine a priori within the validity of Case 2.

8. EXAMPLE 3

The SHG-active monolayer chiral film was prepared by exposing a cleaned fused silica prism to an aqueous solution of ~0.3 mg/mL fluorescein isothiocyanate bovine serum albumin (FITC-BSA, available from Sigma-Aldrich Chemical Co., Milwaukee, Wis.) prepared in ultrapure water (resistivity of >17 M$\Omega$cm). Surfaces were cleaned in a chromic acid bath followed by thorough rinsing in ultrapure water prior to use. Polarization measurements of FITC-BSA films were performed after ~8 hours of surface exposure to ensure complete BSA adsorption and reorganization prior to polarization analysis using the instrumentation of FIG. 1.

The range for the average complex refractive index of the interfacial layer in the limit of Case 1 (Eq. 36) was estimated by Kramers-Kronig transformation of the absorbance spectrum using previously measured values for the refractive index of unlabeled BSA and the surface density of protein. Specifically, the refractive index of unlabeled BSA was assumed to be between 1.36 and 1.63 and the surface excess of protein was assumed to range from 0.5 mg/m$^2$ to 2.4 mg/m$^2$ based on previously reported values. The near-resonance contributions of the fluorescein chromophores were assumed to add to the baseline non-resonant refractive index of the unlabeled protein. Using the labeling density of ~10 fluorescein chromophores per protein provided by the manufacturer together with the film thickness reported previously by ellipsometry and neutron reflection measurements and the measured absorption spectrum (not shown), the imaginary contribution to the refractive index in the visible portion of the spectrum was determined. The contributions to the real part of the refractive index from fluorescein absorption was subsequently determined using Kramers-Kronig dispersion relations, evaluated for the range of film thicknesses and protein surface coverages reported previously.

A summary of the null angles and the corresponding model-independent effective tensor elements is provided in Table 7.

TABLE 7

Measured Null Angles for FITC-BSA

| | $\alpha_{HWP}^{\omega} = -22.5°$ | $\alpha_{HWP}^{\omega} = 22.5°$ | $\alpha_{HWP}^{\omega} = 0°$ | $\alpha_{HWP}^{\omega} = 45°$ |
|---|---|---|---|---|
| $\alpha_{QWP}^{2\omega}$ | 130.6° (±0.2°) | 152.2° (±0.8°) | 90.4° (±0.2°) | 55.6° (±0.3°) |
| $\alpha_{HWP}^{2\omega}$ | 31.21° (±0.05°) | 87.3° (±0.5°) | 65.9° (±0.2°) | 84.6° (±0.3°) |

TABLE 7-continued

Measured Null Angles for FITC-BSA

| | $\alpha_{HWP}^{\omega} = -22.5°$ | $\alpha_{HWP}^{\omega} = 22.5°$ | $\alpha_{HWP}^{\omega} = 0°$ | $\alpha_{HWP}^{\omega} = 45°$ |
|---|---|---|---|---|
| ρ | 0.804 (±0.001) + 0.78i (±0.01i) | −0.97 (±0.01) − 1.17i (±0.05i) | −0.001 (±0.003) − 0.884i (±0.006i) | −0.84 (±0.03) + 0.971i (±0.001i) |

The null angles were acquired by iteratively rotating the wave plates to minimize the detected intensity at PMT 56 (yielding intensity maxima at PMT 57). The complex parameter ρ describing the complete polarization state of the frequency-doubled beam was determined from the measured null angles using Eq. 17. Chirality within the interfacial film is indicated by the observed inequalities $\rho_+ \neq -\rho_-$ and $\rho_L \neq -\rho_R$ (in the absence of chirality, $\rho_+=-\rho_-$ and $\rho_L=-\rho_R$). Values for the effective $x^{(2)}$ tensor elements were obtained directly from these measured null angles with no additional parameters.

Figure 10A:
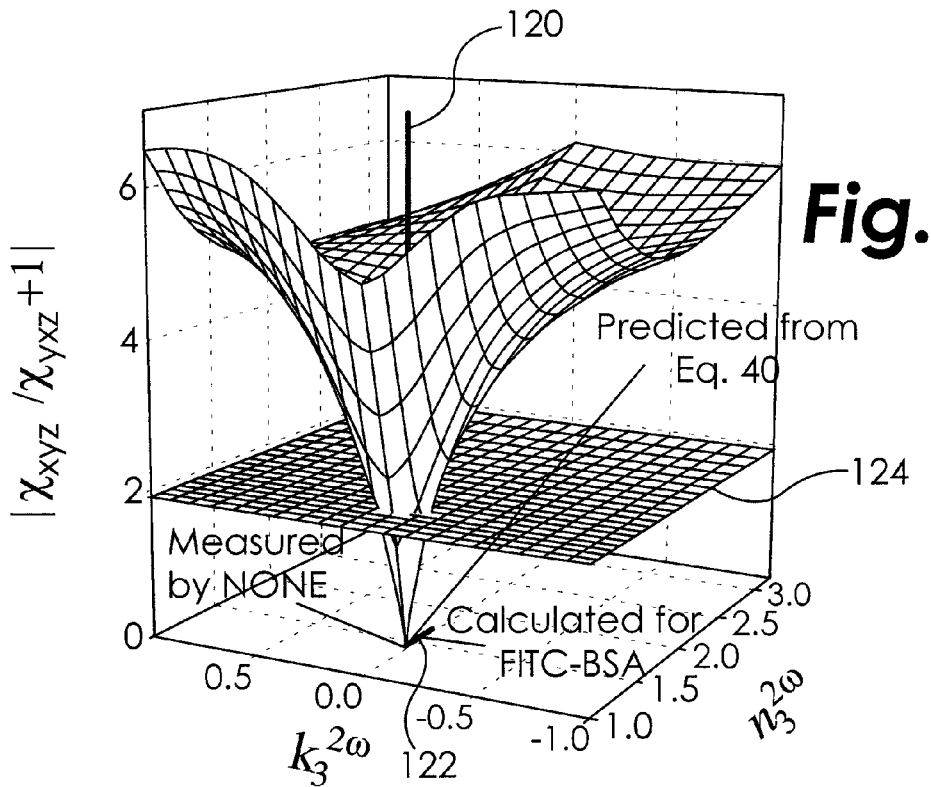
FIG. 10a is a graphical depiction of the approach used in the present invention to determine the interfacial optical constants using the effective $x^{(2)}$ tensor elements measured by NONE for a FITC-BSA film.
Figure 10B:
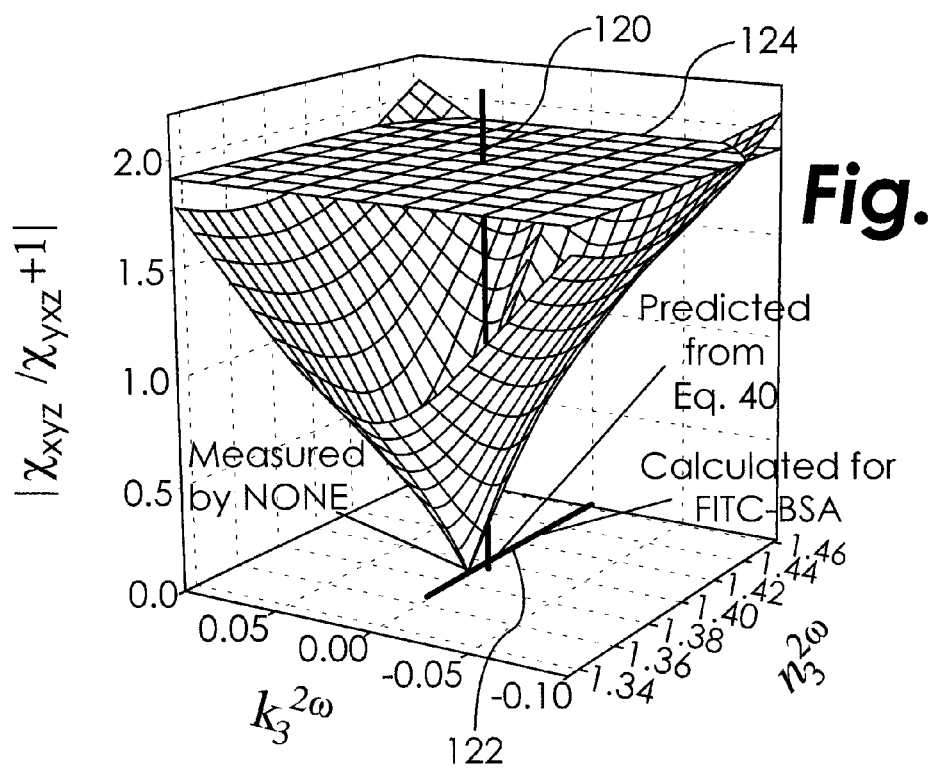

The value of $|x_{XYZ}/x_{YXZ}+1|=|s_2x_{psp}/s_4x_{spp}-1|$ calculated using the Fresnel factors for Models A (Eqs. 31 and 32) and B (described in the Supporting Calculations hereinbelow) is shown in FIG. 10 as a function of the real and imaginary component of the interfacial refractive index. FIG. 10 is a graphical depiction of the approach used to determine the interfacial optical constants using the effective $x^{(2)}$ tensor elements measured by NONE for a FITC-BSA film, shown in both FIG. 10a and FIG. 10b. FIG. 10b contains an expanded view of the region corresponding to the minimum in FIG. 10a. The complex-valued effective refractive index is given by $n_3^{2\omega}-ik_3^{2\omega}$. The optical constants that recover the required symmetry condition $x_{XYZ}=-x_{YXZ}$ correspond to the minimum of the contour plot, calculated using the Fresnel factors from Model A. The vertical line 120 indicates the values of interfacial optical constants predicted using the simple effective medium model described in Eq. 40 (Case 2), and the horizontal region 122 indicates the estimated range of optical constants for a FITC-BSA monolayer (Case 1). The horizontal plane 124 corresponding to $|x_{XYZ}/x_{YXZ}+1|=1.91$ for all values of $k_3^{2\omega}$ and $n_3^{2\omega}$ is the result obtained from the Fresnel factors calculated using Model B.

The contour plot of FIG. 10 obtained using Model A exhibits a minimum in the calculated value of $|x_{XYZ}/x_{YXZ}+1|$ for $n_3^{2\omega}=1.387\pm0.005$ and $k_3=0.0000\pm0.0009$. Implicit in these calculations is the assumption that birefringence within the effective interfacial refractive index is negligible. If Case 1 is correct and 1/γ>>d, birefringence in the effective interfacial refractive index is not expected since neither the substrate (fused silica) nor the superstrate (water) exhibits birefringence. However, the assumption of a spatially isotropic linear polarizability may not be justified if 1/γ<<d as in Case 2. The high precision in the measured values of $n_3$ and $k_3$ arises from the remarkable sensitivity of the calculated ratio on the interfacial optical constants. Small errors in the choice of the interfacial optical constants resulted in large deviations in the calculated magnitudes and phases of the $x^{(2)}$ tensor elements.

Also shown in FIG. 10 are the results of an identical calculation performed using the expressions for the Fresnel factors derived from Model B. The specific differences between the two models in the limit of an ultrathin film are detailed in the Supporting Calculations hereinbelow. In Model B, only $L_{ZZ}^{B,2\omega}$ and $L_{ZZ}^{B,\omega}$ depend on the interfacial optical constants. Since $L_{ZZ}^{B,\omega}$ appears in both the numerator and the dominator in the ratio $s_2x_{psp}/s_4x_{spp}$ and $L_{ZZ}^{B,2\omega}$ does not appear at all, Model B yields a constant value of 0.024−1.61i for the calculated ratio of $x_{XYZ}/x_{YXZ}$ (indicated by the horizontal plane 124 in FIG. 10), irrespective of the choice of optical constants for the interfacial layer. This measured ratio is clearly inconsistent with the value of −1+0i demanded by symmetry.

NONE measurements were also performed on a model achiral molecular system (DR-19) oriented at the propanol solution/silica interface. Since the refractive index of 2-propanol is different from that of water (cf. 1.3776 and 1.334, respectively), the Fresnel factors generated from total internal reflection SHG measurements performed using propanol as the solvent differ significantly from those obtained from aqueous interfaces. The results of the DR-19 measurements performed at the propanol solution/silica interface using Eq. 40 to calculate the interfacial optical constants are summarized in Tables 8 and 9.

TABLE 8

Measured Null Angles for DR-19.

| | $\alpha_{HWP}^{\omega} = 22.5°$ | $\alpha_{HWP}^{\omega} = 0°$ |
|---|---|---|
| $\alpha_{QWP}^{2\omega}$ | 153.8° (±0.5°) | 129.2° (±0.7°) |
| $\alpha_{HWP}^{2\omega}$ | 79.9° (±0.2°) | 4.6° (±0.1°) |
| ρ | −1.92 (±0.04) − 0.52i (±0.05i) | 0.55 (±0.03) − 0.963i (±0.007i) |

TABLE 9

Surface Tensor Elements Evaluated Using the Predicted Effective Interfacial Optical Constants for DR-19 (Model B, Case 2).

| $\chi_{xxz}$ | $\chi_{zxx}$ | $\chi_{zzz}$ |
|---|---|---|
| 1 | 1.00 (±0.04) −0.05i (±0.07i) | 2.74 (±0.02) −0.75i (±0.06i) |

| | Predicted[a] | Measured |
|---|---|---|
| $D = \dfrac{\chi_{zzz} - \chi_{zxx} + \chi_{xxz}}{\chi_{zzz} - \chi_{zxx} + 3\chi_{xxz}}$ | 0.6 + 0i | 0.59 (±0.02) +0.07i (±0.03i) |
| $\dfrac{\chi_{zxx} + 2\chi_{xxz}}{\chi_{zzz}}$ | 1 + 0i | 1.01 (±0.08) +0.29i (±0.06i) |

[a] Valid in the limit of weak orientational order.

Comparison of Measured Optical Constants with Predicted Results

Case 1: 1/γ<<d

In the limit of 1/γ<<d, the optical constants of the nonlinear optically active interfacial layer are given exclusively by the optical properties of the oriented molecules at the interface. This limiting behavior is consistent with the large majority of the optical models currently used to treat experimental SHG and SFG polarization measurements. Previous ellipsometry measurements suggest a reasonable value of $1.36 \leq n_3^{2\omega} \leq 1.63$ for the refractive index of an unlabeled BSA monolayer film. Additional corrections to account for the presence of the near-resonant fluorescein chromophore label were performed by Kramers-Kronig transformation of the measured absorbance spectrum of fluorescein in solution together with predicted values for the film thickness yield optical constants of $1.37 \leq n_3^{2\omega} \leq 1.66$ and $0.0004 \leq k_3^{2\omega} \leq 0.002$ for the FITC-BSA monolayer film. From inspection of the results summarized in FIG. 10, the minimum in the plot of $|x_{XYZ}/x_{YXZ}+1|$ as a function of $n_3^{2\omega}$ and $k_3^{2\omega}$ does, in fact, fall within the envelope of the optical constants calculated for FITC-BSA films. It should be emphasized that the calculated envelope of possible optical constants for a monolayer film of FITC-labeled BSA should be considered a guideline given the broad range of previously reported optical constants and film thicknesses for BSA films at aqueous interfaces.

Case 2: $1/\gamma \cong \lambda \gg d$

In the second limiting case, a decay length comparable to the wavelength of light was assumed (Eq. 38). This limiting behavior is consistent with previous treatments of light propagating within thin film optical waveguides, but differs significantly from the large majority of previous interpretations of nonlinear optical effects at surfaces. In the limit of a film thickness that is much less than the wavelength of light in Case 2, Eqs. 39 and 40 suggest that the contributions from the ambient and the substrate will dominate the effective interfacial optical constants. Within the validity of the simplified effective medium model in Eq. 40, the effective optical properties of the interfacial layer can be calculated directly from the bulk optical constants with no adjustable parameters. Since neither water nor fused silica is birefringent, the effective optical constants describing the FITC-BSA layer in Case 2 will exhibit negligible birefrigence. The interfacial optical constants measured by NONE and those calculated using Eq. 40 are compared in FIG. 10 and Table 10.

TABLE 10

Comparison of Measured and Predicted Interfacial Optical Constants for FITC-BSA.

| Optical Constants | Measured by NONE | Predicted from Model A[a.] | Predicted from Model B[b.] |
|---|---|---|---|
| $n_3^{2\omega}$ | 1.387 (±0.005) | 1.3982 | 1.365 to 1.655 |
| $k_3^{2\omega}$ | 0.0000i (±0.0009i) | 0 | 0.0004i to 0.002i |

[a.]From Eq. 40.
[b.]From prior art combined with Kramers-Kronig transformation of the visible absorbance spectrum.

The agreement between the theoretically predicted results and the experimentally measured values is quite remarkable. The two values were determined independently with no adjustable parameters and agreed within a relative error of less than 1%.

The reliability of the mathematical approach used to generate the effective interfacial optical constants summarized in Table 10 from the NONE measurements depicted in FIG. 10 can be evaluated by analysis of the corresponding achiral $x^{(2)}$ tensor elements shown in Table 11.

TABLE 11

Surface Tensor Elements Evaluated Using the Measured Effective Interfacial Optical Constants for FITC-BSA

| $\chi_{ssp}$ | $\chi_{pss}$ | $\chi_{psp}$ | $\chi_{spp}$ | $\chi_{ppp}$ |
|---|---|---|---|---|
| 1 | −0.01 (±0.02) +0.31i (±0.01i) | −0.30 (±0.01) −0.10i (±0.01i) | −0.05 (±0.01) −0.173i (±0.002i) | 0.935 (±0.009) +0.66i (±0.01i) |

TABLE 11-continued

Surface Tensor Elements Evaluated Using the Measured Effective Interfacial Optical Constants for FITC-BSA

| $\chi_{xxz}$ $\chi_{zxx}$ | $\chi_{xyz}$ | $\chi_{yxz}$ | $\chi_{zzz}$ |
|---|---|---|---|
| 1 −0.01 (±0.04) +0.66i (±0.02i) | 0.56 (±0.01) +0.12i (±0.03i) | −0.566 (±0.009) −0.12i (±0.04i) | 2.16 (±0.03) +0.73i (±0.04i) |

| | Predicted[a.] | Measured |
|---|---|---|
| $D = \dfrac{\chi_{ZZZ} + 2\chi_{ZXX} - 2\chi_{XXZ}}{\chi_{ZZZ} + 4\chi_{ZXX} - 2\chi_{XXZ}}$ | 0.6 + 0i | 0.61 (±0.05) −0.02i (±0.03i) |
| $\dfrac{\chi_{ZXX} + 2\chi_{XXZ}}{\chi_{ZZZ}}$ | 1 + 0i | 0.84 (±0.01) +0.08i (±0.06i) |

[a.]Valid in the limit of weak orientational order.

If the expressions for the Fresnel factors given in Eqs. 31 and 32 are accurate, several relationships between the measured achiral $x^{(2)}$ tensor elements are expected to emerge. Given the numerous binding locations for the fluorescein chromophore in FITC-BSA, it is reasonable to expect the overall orientation distribution of the fluorescein label to be quite broad. In this weak orientation limit, the following relationship is expected to hold in SHG and SFG measurements of uniaxial thin films, irrespective of molecular symmetry.

$$x_{ZZZ} \cong x_{XXZ} + x_{XZX} + x_{ZXX} \quad (41)$$

Additionally, if it is assumed that the dominant molecular tensor elements are $\beta_{x'x'z'}$ and $\beta_{z'z'z'}$ (consistent with a two-state chromophore exhibiting resonance-enhancement at the second harmonic frequency), the orientation parameter D is expected to be ⅗ in the limit of a broad orientation distribution (i.e., the magic angle result).

$$D \equiv \frac{\langle \cos^3\theta \rangle}{\langle \cos\theta \rangle} = \frac{\chi_{ZZZ} + 2\chi_{ZXX} - 2\chi_{XXZ}}{\chi_{ZZZ} + 4\chi_{ZXX} - 2\chi_{XXZ}} \quad (42)$$

The values of $(x_{ZXX}+2x_{XXZ})/x_{ZZZ}$ and D obtained from NONE analysis of the FITC-BSA ultrathin film are summarized in Table 11. The experimentally measured ratio of $(x_{ZXX}+2x_{XXZ})/x_{ZZZ}$ using the values of $n_3^{2\omega}$ and $k_3^{2\omega}$ obtained from FIG. 10 was 0.918+0.032i, in excellent agreement with the anticipated result of 1+0i. The value for the orientation parameter D calculated from the NONE measurements of FITC-BSA films using Eq. 42 was 0.609–0.020i, again in excellent agreement with expectations. It is worth emphasizing that the predicted relationships $(x_{ZXX}+2x_{XXZ})/x_{ZZZ} \cong 1+0i$ and $\langle\cos^3\theta\rangle/\langle\cos\theta\rangle \cong 0.6+0i$ were recovered with no adjustable parameters and using combinations of $x^{(2)}$ tensor elements containing significant imaginary contributions. The recovery of these predicted relationships provides compelling evidence supporting the validity of the NONE measurement approach for determining the $x^{(2)}$ tensor elements in chiral films and the reliability of the expressions for the Fresnel factors proposed in Eqs. 31 and 32.

Comparison of the Limiting Cases 1 and 2

The NONE measurements of FITC-BSA are nominally in agreement with the results predicted from both Cases 1 and 2, primarily because of the large uncertainty in the estimated refractive index and thickness for a FITC-BSA film. However, additional insights into the appropriate limiting condition for treating SHG and SFG measurements of ultrathin films can be gained from the results of the NONE measurements obtained for the strongly-resonant achiral system consisting of an adsorbed DR-19 layer at the silica/propanol solution interface (Tables 8 and 9). Measurements of DR-19 films are particularly useful to test the effective medium model proposed in Eq. 40, since DR-19 exhibits strong resonance-enhancement at the second harmonic wavelength. In the presence of resonance-enhancement within an ultrathin SHG-active film, the interfacial optical model described in Case 1 requires a significant (and perhaps dominant) imaginary component within the interfacial refractive index while Case 2 demands a negligible imaginary component.

The use of a purely real effective interfacial optical constant given by the average refractive index consistent with the limiting behavior described by Case 2 yielded the set of resonance-enhanced $\chi^{(2)}$ tensor elements summarized in Table 9 for DR-19 oriented at the silica/propanol solution interface. In contrast to fluorescein, molecular modeling calculations and previous experimental measurements demonstrate that the nonlinear polarizability of DR-19 at these frequencies is dominated by the single molecular tensor element $\beta_{z'z'z'}$, yielding an expected ratio of $\chi_{ZXX}/\chi_{XXZ} \cong 1+0i$. Furthermore, if DR-19 adopts a relatively broad distribution in molecular orientation (a reasonable assumption for a physisorbed dye molecule at a solid/liquid interface), the relationships $D = \langle\cos^3\theta\rangle/\langle\cos\theta\rangle \cong 0.6+0i$ and $(\chi_{ZXX}+2\chi_{XXZ})/\chi_{ZZZ} \cong 1+0i$ are again expected to arise. Use of the simple effective medium approximation in Eq. 40 (Case 2) with no adjustable parameters satisfied all three of these predictions (Table 9). Although it is nontrivial to estimate the appropriate values for the complex-valued refractive index tensor for the DR-19 monolayer film, reliable values of the $\chi^{(2)}$ tensor elements would generally not be expected using only purely real values for the interfacial optical constants under conditions of strong resonance-enhancement and/or birefringence within the validity of Case 1. The apparent success of the simple effective medium approximation in both chiral and achiral surface films shows that reliable values of the $\chi^{(2)}$ tensor elements can be obtained in films much less than the wavelength of light from knowledge of the bulk optical constants alone using the simple effective medium approximation given in Eq. 40.

As demonstrated above, NONE was used to experimentally extract relative values of all five nonzero effective $\chi^{(2)}$ tensor elements present in uniaxially oriented chiral films with full phase information. From these measurements together with the symmetry relationship $\chi_{YXZ} = -\chi_{XYZ}$, the real and imaginary components of the interfacial refractive index were uniquely obtained with no adjustable parameters and independent of both the molecular symmetry and polar orientation. A relatively simple effective medium thin film model combined with new expressions for the Fresnel factors resulted in predicted values for the effective interfacial refractive index that agreed with the experimentally observed results within a relative error of less than 1% with no adjustable parameters. Furthermore, the corresponding achiral $\chi^{(2)}$ tensor elements obtained using the measured interfacial optical constants yielded relationships in excellent agreement with expected trends for a system exhibiting weak orientational order. This same simple optical model was also demonstrated to yield reasonable results for strongly resonance-enhanced measurements of an achiral film at the propanol/fused silica interface.

The remarkable agreement between the interfacial optical constants measured experimentally by NONE with no adjustable parameters and those calculated independently using Eq. 40 allows three key conclusions to be drawn. First, nonlinear optical ellipsometry can be used to reliably determine the full set of $\chi^{(2)}$ tensor elements in uniaxially oriented chiral and achiral films with retention of phase information. Second, the Fresnel factors given in Eqs. 31 and 32 and derived in the Supporting Calculations hereinbelow accurately describe the thin film optics in the total internal reflection measurements performed in this Example, while Fresnel factors routinely used in the prior art could not be made to be consistent with the experimental results. Finally, the effective refractive index of the interfacial layer in SHG and SFG measurements of films much smaller than the wavelength of light can often be quantitatively predicted a priori from knowledge of the bulk optical constants bridging the interface. These three combined results have the potential to substantially simplify future interpretation of nonlinear optical polarization measurements in SHG and SFG surface analyses.

9. MODULAR ELLIPSOMETRIC ANALYSIS OF THE MEASUREMENT INSTRUMENT

A modular approach in the NOE instrument allows multiple experimental configurations to be understood within a single compact and intuitive mathematical framework. The three modules of the instrument consist of (1) the optics between the sample and the detector, (2) the sample configuration, and (3) the optics used to prepare the polarization state of the incident beam. The inherent flexibility of the ellipsometric analysis approach allows for a large degree of interchangeability between the optical configurations in each module. It is convenient to start with the optics following the sample.

Measuring the Complete Polarization State of the Nonlinear Optical Beam

For both SHG and SFG, the optical components used for detecting the polarization state of the nonlinear beam can be treated using a series of Jones matrices. The Jones matrix for a polarizer (pol) rotated an arbitrary angle $\gamma$ with respect to the p-coordinate is given by $R(-\alpha_{pol})M_{pol}R(\alpha_{pol})$, in which R is the rotation matrix and $M_{pol}$ is the Jones matrix of a polarizer set to pass p-polarized light.

$$M_{pol}(\alpha_{pol}) = R(-\alpha_{pol})M_{pol}R(\alpha_{pol}) = \begin{bmatrix} \cos^2\alpha_{pol} & \sin\alpha_{pol}\cos\alpha_{pol} \\ \sin\alpha_{pol}\cos\alpha_{pol} & \sin^2\alpha_{pol} \end{bmatrix} \quad (43)$$

Analogous expressions can be derived for both half and quarter wave plates rotated by the angles $\alpha_Q$ and $\alpha_H$, respectively.

$$M_Q(\alpha_Q) = R(-\alpha_Q)M_Q R(\alpha_Q) = \begin{bmatrix} \cos 2\alpha_Q - i & \sin 2\alpha_Q \\ \sin 2\alpha_Q & -\cos 2\alpha_Q - i \end{bmatrix} \quad (44)$$

$$M_H(\alpha_H) = R(-\alpha_H)M_H R(\alpha_H) = \begin{bmatrix} \cos 2\alpha_H & \sin 2\alpha_H \\ \sin 2\alpha_H & -\cos 2\alpha_H \end{bmatrix} \quad (45)$$

Three different null-ellipsometric configurations for extracting the complete polarization state are considered. In the first, the nonlinear beam generated at the interface is passed through a quarter wave plate (Q), a half wave plate (H), and a polarizer set to pass s-polarized light. The second optical pathway is identical to the first except the polarizer is set to pass p-polarized light. In the third optical pathway, a quarter wave plate and a rotating polarizer are employed.

Quarter Wave Plate/Half Wave Plate/s-Polarizer

Figure 11A:
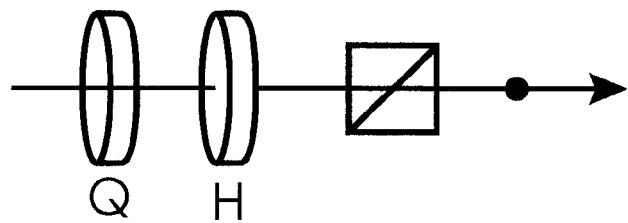
FIG. 11a is a schematic representation of a configuration for the detection optical pathway (the arrow represents the direction of the light beam) having two rotating wave plates and a polarizer set to pass s-polarized light.

Referring to FIG. 11a, the polarization state of the second harmonic light after passing the set of exigent optics can be evaluated by matrix multiplication of the frequency-doubled electric field generated at the sample.

$$e_{det}^{2\omega} = [M_{pol}^{2\omega}(\pi/2)][M_H^{2\omega}(\alpha_H^{2\omega})][M_Q^{2\omega}(\alpha_Q^{2\omega})] e_{sample}^{2\omega} \quad (46)$$

The vector $e_{sample}^{2\omega}$ describes the polarization state of the second harmonic beam with the electric field of the p-polarized light over the electric field of the s-polarized light. Substitution of the appropriate expressions for the Jones matrices for a quarter wave plate rotated an angle $\alpha_Q^{2\omega}$, a half wave plate rotated an angle $\alpha_H^{2\omega}$, and polarizer rotated 90°, followed by simplification using trigonometric identities allows Eq. 46 to be rewritten in the following form.

$$e_{det}^{2\omega} = \begin{bmatrix} e_p^{2\omega} \\ e_s^{2\omega} \end{bmatrix}_{det} = \begin{bmatrix} 0 & 0 \\ \sin(2\alpha_H^{2\omega} - 2\alpha_Q^{2\omega}) - i\cos 2\alpha_H^{2\omega} & \cos(2\alpha_H^{2\omega} - 2\alpha_Q^{2\omega}) + i\cos 2\alpha_H^{2\omega} \end{bmatrix} e_{sample}^{2\omega} \quad (47)$$

Using Eq. 47, the complete polarization state of the nonlinear beam can be obtained from the rotation angles $\alpha_Q^{2\omega}$ and $\alpha_H^{2\omega}$ that result in a minimum in the detected intensity (corresponding to the condition $|e_{det}^{2\omega}|=0$). As stated hereinabove and repeated here for convenience, by analogy with linear ellipsometry, a complex-valued parameter $\rho$ can be defined as the ratio of the p-polarized to s-polarized electric field components.

$$\rho = \frac{e_p^{2\omega}}{e_s^{2\omega}} = \frac{\cos(2\alpha_H^{2\omega} - 2\alpha_Q^{2\omega}) + i\cos(2\alpha_H^{2\omega})}{-\sin(2\alpha_H^{2\omega} - 2\alpha_Q^{2\omega}) + i\sin(2\alpha_H^{2\omega})} \quad (48)$$

The parameter $\rho$ contains both amplitude and phase information. By analogy with linear ellipsometry, ellipsometric angles $\psi$ and $\Delta$ can be defined with respect to $\rho$.

$$\tan \Psi = |\rho| \quad (49)$$

$$\Delta = \arg(\rho) \quad (50)$$

In practice, it is often more convenient to simply use the complex parameter $\rho$ in determination of the $\chi^{(2)}$ tensor elements, rather than the angles $\Delta$ and $\Psi$.

Quarter Wave Plate/Half Wave Plate/p-Polarizer

Figure 11B:
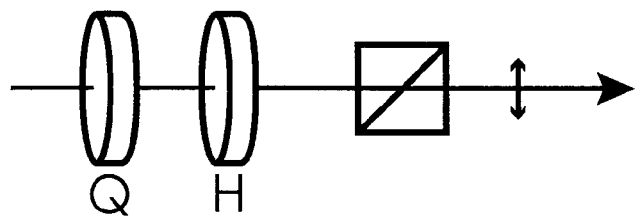
FIG. 11b is a schematic representation of a configuration for the detection optical pathway (the arrow represents the direction of the light beam) having two rotating wave plates and a polarizer set to pass p-polarizer light.

Referring to FIG. 11b, the derivation for the expression for $\rho$ in the case of p-polarized detection following a quarter wave plate/half wave plate combination is similar to that for s-polarized detection. Substitution of the appropriate Jones matrices followed by trigonometric simplification yields the following expression for the detected beam.

$$e_{det}^{2\omega} = \begin{bmatrix} \cos(2\alpha_H^{2\omega} - 2\alpha_Q^{2\omega}) - i\cos 2\alpha_H^{2\omega} & -\sin(2\alpha_H^{2\omega} - 2\alpha_Q^{2\omega}) - i\cos 2\alpha_H^{2\omega} \\ 0 & 0 \end{bmatrix} e_{sample}^{2\omega} \quad (51)$$

From the rotation angles $\alpha_Q^{2\omega}$ and $\alpha_H^{2\omega}$ that produce zero intensity at the detector, the complex parameter $\rho$ can be easily obtained.

$$\rho = \frac{e_p^{2\omega}}{e_s^{2\omega}} = \frac{\sin(2\alpha_H^{2\omega} - 2\alpha_Q^{2\omega}) + i\sin(2\alpha_H^{2\omega})}{\cos(2\alpha_H^{2\omega} - 2\alpha_Q^{2\omega}) - i\cos(2\alpha_H^{2\omega})} \quad (52)$$

Quarter Wave Plate/Rotating Polarizer

Figure 11C:
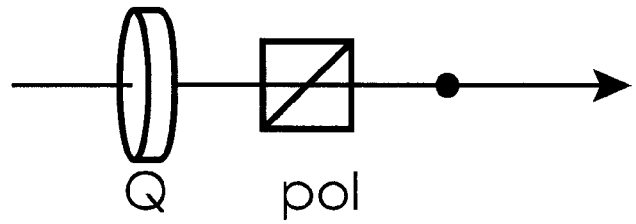
FIG. 11c is a schematic representation of a configuration for the detection optical pathway (the arrow represents the direction of the light beam) having a rotating quarter wave plate and rotating polarizer.

Referring to FIG. 11c, null ellipsometry can also be achieved using only a quarter wave plate and a polarizer. The resulting expression for $\rho$ in terms of the quarter wave plate rotation angle $\alpha_Q^{2\omega}$ and polarizer rotation angle $\alpha_{pol}^{2\omega}$ producing an intensity minimum at the detector is given by the following.

$$\rho = \frac{e_p^{2\omega}}{e_s^{2\omega}} = \frac{\sin(\alpha_{pol}^{2\omega} - 2\alpha_Q^{2\omega}) + i\sin(\alpha_{pol}^{2\omega})}{\cos(\alpha_{pol}^{2\omega} - 2\alpha_Q^{2\omega}) - i\cos(\alpha_{pol}^{2\omega})} \quad (53)$$

The rotating polarizer approach described by Eq. 53 has the advantage of requiring fewer optical components than the preceding configurations, but can potentially lead to undesirable artifacts if any subsequent optical elements exhibit polarization dependence (e.g., diffraction grating, side-on photomultiplier tubes, etc.).

SHG Rotating Analyzer Ellipsometry (SHG-RAE)

Figure 11D:
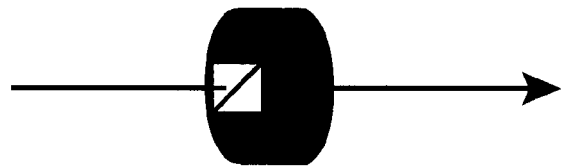
FIG. 11d is a schematic representation of a configuration for the detection optical pathway (the arrow represents the direction of the light beam) having a rotating polarizer.

Referring to FIG. 11d, determination of the complete polarization state of the nonlinear optical beam can be also determined using alternative ellipsometric methods. By analogy with approaches developed for linear ellipsometry, the polarization state can also be obtained from the detected intensity as a function of the rotation angle of polarizer (analyzer). Evaluation of the Jones matrices for a rotating analyzer configuration with the final polarizer set to pass p-polarized light follow closely the derivations presented hereinabove.

$$e_{det}^{2w}(\alpha_{pol}^{2w}) = \begin{bmatrix} 1 & 0 \\ 0 & 0 \end{bmatrix} \begin{bmatrix} \cos\alpha_{pol}^{2w} & \sin\alpha_{pol}^{2w} \\ -\sin\alpha_{pol}^{2w} & \cos\alpha_{pol}^{2w} \end{bmatrix} \begin{bmatrix} e_p^{2w} \\ e_s^{2w} \end{bmatrix} \quad (54)$$

Evaluation of Eq. 18 yields the following general expression for the detected intensity.

$$I_{det}^{2\omega} \propto |e_p^{2\omega}|^2 \cos^2(\alpha_{pol}^{2\omega}) + |e_s^{2\omega}|^2 \sin^2(\alpha_{pol}^{2\omega}) + 2[Re(e_p^{2\omega})Re(e_s^{2\omega}) + Im(e_p^{2\omega})Im(e_s^{2\omega})] \sin(\alpha_{pol}^{2\omega}) \cos(\alpha_{pol}^{2\omega}) \quad (55)$$

Trigonometric substitution allows the above expression to be rewritten in the following form.

$$I_{det}^{2\omega} \propto A \cos(2\alpha_{pol}^{2\omega}) + B \sin(2\alpha_{pol}^{2\omega}) + C \quad (56a)$$

$$A = \tfrac{1}{2}(|e_p^{2\omega}|^2 - |e_s^{2\omega}|^2) \quad (56b)$$

$$B = Re[(e_p^{2\omega})(e_s^{2\omega})^*] \quad (56c)$$

$$C = \tfrac{1}{2}(|e_p^{2\omega}|^2 + |e_s^{2\omega}|^2) \quad (56d)$$

Since the relative amplitude and phase between the p- and s-polarized fields determines the polarization state, we can always choose a reference frame such that the s-polarized field is purely real. In this reference system, the imaginary elements in B disappear. Appropriate combinations of the three constants A, B, and C, then allow determination of the exigent polarization state.

$$|\rho|^2 = \left(\frac{C+A}{C-A}\right) \quad (57a)$$

$$Re(\rho) = \frac{B}{C-A} \quad (57b)$$

$$\rho = Re(\rho) + iIm(\rho) = \frac{B \pm i\sqrt{C^2 - A^2 - B^2}}{C-A} \quad (57c)$$

The sign ambiguity in ρ arises because the sense of ellipticity (right vs. left) of the exigent beam cannot be determined a priori from simple rotating analyzer measurements. The analogous expression for a polarizer designed to pass s-polarized light in Eq. 54 can be similarly derived.

$$|\rho|^2 = \left(\frac{C-A}{C+A}\right) \quad (58a)$$

$$Re(\rho) = \frac{-B}{C+A} \quad (58b)$$

$$\rho = Re(\rho) + iIm(\rho) = \frac{B \pm i\sqrt{C^2 - A^2 - B^2}}{C+A} \quad (58c)$$

Figure 11E:
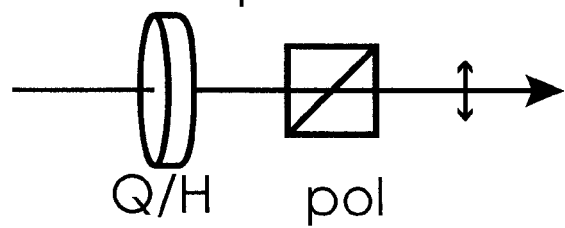
FIG. 11e is a schematic representation of a configuration for the detection optical pathway (the arrow represents the direction of the light beam) having a rotating wave plate and polarizer set to pass p-.

A closely related experimental setup to SHG-RAE is that of SHG using rotating half wave plate ellipsometry (RHE). For this method, a rotating half wave plate is placed before a fixed polarizer (FIG. 11e). The mathematical treatment of the data is virtually identical to the SHG-RAE, except $\alpha_{pol}^{2\omega}$ in Eq. 56a is replaced with $2\alpha_H^{2\omega}$.

$$I_{det}^{2\omega} \propto A \cos(4\alpha_H^{2\omega}) + B \sin(4\alpha_H^{2\omega}) + C \quad (59)$$

All subsequent treatments are identical for both SHG-RHE and SHG-RAE.

The SHG-RHE experimental configuration has some practical advantages over the SHG-RAE. Photomultiplier tubes can routinely show differences in sensitivity depending on the polarization state of the light that is being detected, potentially leading to artifacts in subsequent fits of intensity-based measurements. The use of a rotating wave plate with a fixed polarizer ensures the same polarization is striking the PMT at all times. The SHG-RHE configuration also allows for the convenient use of two PMTs allowing for two independent data sets in each experiment when using a polarizing beamsplitting cube or prism.

SHG Rotating Quarter Wave Plate Ellipsometry (SHG-RQE)

The sign ambiguity arising in rotating analyzer ellipsometry can be resolved by using a rotating quarter wave plate configuration. The Jones matrices for an optical path consisting of the sample, a rotating quarter wave plate, and a fixed polarizer set to pass p-polarized light prior to detection are given below (FIG. 11e).

$$e_{det}^{2\omega}(\alpha_Q^{2\omega}) = \begin{bmatrix} 1 & 0 \\ 0 & 0 \end{bmatrix} \begin{bmatrix} \cos(2\alpha_Q^{2\omega}) - i & \sin(2\alpha_Q^{2\omega}) \\ \sin(2\alpha_Q^{2\omega}) & -\cos(2\alpha_Q^{2\omega}) - i \end{bmatrix} \begin{bmatrix} e_p^{2\omega} \\ e_s^{2\omega} \end{bmatrix} \quad (60)$$

Explicit evaluation of the detected intensity followed by substitution of trigonometric relations allows Eq. 60 to be reduced to the following form in a manner similar to that described for rotating polarizer ellipsometry.

$$I_{det}^{2\omega} \propto K \sin(2\alpha_Q^{2\omega}) + L \sin(4\alpha_Q^{2\omega}) + M \cos(4\alpha_Q^{2\omega}) + N \quad (61a)$$

$$K = 2Im[(e_p^{2\omega})(e_s^{2\omega})^*] \quad (61b)$$

$$L = Re[(e_p^{2\omega})(e_s^{2\omega})^*] \quad (61c)$$

$$M = \tfrac{1}{2}[|e_p^{2\omega}|^2 - |e_s^{2\omega}|^2] \quad (61d)$$

$$N = \tfrac{1}{2}[3|e_p^{2\omega}|^2 + |e_s^{2\omega}|^2] \quad (61e)$$

Appropriate combinations of these relations yield the following expression for $\rho^{2\omega}$.

$$\rho = \frac{M+N}{2L-iK} \quad (62)$$

Figure 11F:
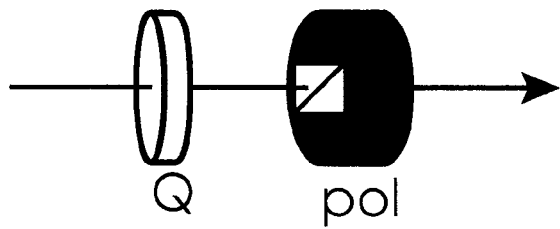
FIG. 11f is a schematic representation of a configuration for the detection optical pathway (the arrow represents the direction of the light beam) having a rotating wave plate and polarizer set to pass s-.

If the detection geometry is changed such that the final fixed polarizer passes s-polarized light rather than p-polarized light, the expression for ρ changes to the following (FIG. 11f).

$$\rho = \frac{-2L - iK}{M+N} \quad (63)$$

Figure 12:
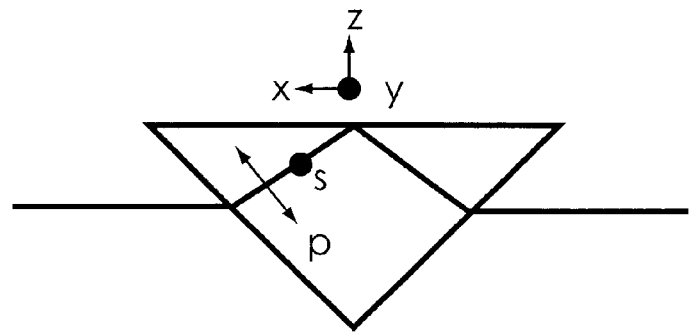
FIG. 12 is a schematic diagram showing a projection of the p- and s-polarization notation onto the Cartesian geometric system as used to describe molecular orientation at an interface.

Expressing the Nonlinear Optical Polarization in Terms of the $\chi^{(2)}$ Tensor Elements Regardless of the specific optical configuration used (e.g., NONE, SHG-RAE, or SHG-RQE), the ellipsometry measurements yield the complex parameter ρ, which in turn describes the complete polarization state of the nonlinear optical beam. As shown hereinbelow in the Supporting Calculations, projection of the incident and exigent s- and p-coordinate systems onto the surface (Cartesian) coordinate system leads to the following general expression for ρ in the case of SHG with a single incident beam (FIG. 12).

$$\rho = \frac{\chi_{ppp}(e_p^\omega)^2 + \chi_{psp}e_s^\omega e_p^\omega + \chi_{pss}(e_s^\omega)^2}{\chi_{spp}(e_p^\omega)^2 + \chi_{ssp}e_s^\omega e_p^\omega + \chi_{sss}(e_s^\omega)^2} \quad (64)$$

The effective $\chi^{(2)}$ tensor elements in Eq. 64 are model-independent parameters describing the macroscopic polarization characteristics of the sample. They are given by combinations of surface tensor elements multiplied by geometric terms and model-dependent Fresnel factors relating the incident and exigent electric fields to the fields within the ultrathin interfacial layer. In uniaxially oriented films, the effective tensor elements are given by the following expressions.

$$\chi_{ppp} = \mp s_3 \chi_{XXZ} + s_5 \chi_{ZXX} + s_7 \chi_{ZZZ} \quad (65a)$$

$$\chi_{psp} = \mp s_4 \chi_{XYZ} \quad (65b)$$

$$\chi_{pss} = s_6 \chi_{ZYY} \quad (65c)$$

$$\chi_{spp} = s_2 \chi_{YXZ} \quad (65d)$$

$$\chi_{ssp} = s_1 \chi_{YYZ} \quad (65e)$$

$$\chi_{sss} = 0 \quad (65f)$$

The ∓ symbol should be positive for transmission measurements and negative for reflection and total internal reflection measurements. Explicit expressions for the s coefficients in Eq. 65 are detailed hereinbelow in the Supporting Calculations section for measurements performed in reflection.

Experimental Determination of the $\chi^{(2)}$ Tensor Elements

The set of optics used to prepare the polarization state of the incident beam can also be treated in a modular manner. In the following discussion, it will be assumed that the optical components preceding the sample consist of a fixed polarizer (or equivalently, a polarized laser or other light source), a rotatable half wave plate, and a fixed quarter wave plate oriented at ±45°. The polarizer and the quarter wave plate may each be fixed at one of two settings (s- or p- and ±45°, respectively), providing four general cases for considering the incident optics. In general, the polarization of light that reaches the sample can be described by the expression:

$$e^\omega = M_Q M_H M_{pol} e_{in}^\omega \quad (66)$$

The four different combinations of the considered settings for the polarizer and the quarter wave plate lead to only two unique outcomes for the polarization state of the beam entering the sample as a function of the half wave plate rotation angle $\alpha_H^\omega$ and are referred to as configurations A and B.

Configuration A

Figure 13A:
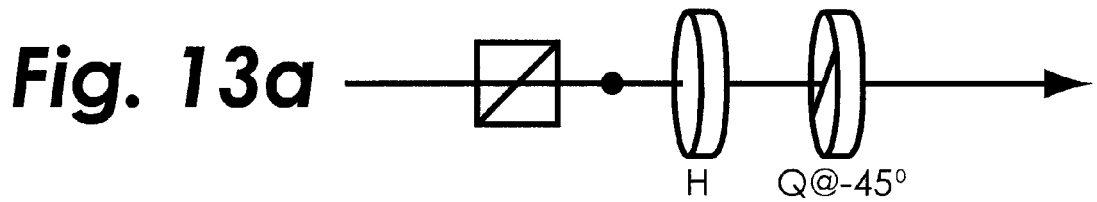
FIG. 13a is a schematic representation of a configuration for the incident optical pathway (the arrow represents the direction of the light beam) with the polarizer set to pass s-polarizer light, rotating half wave plate and quarter wave plate at −45°.
Figure 13B:
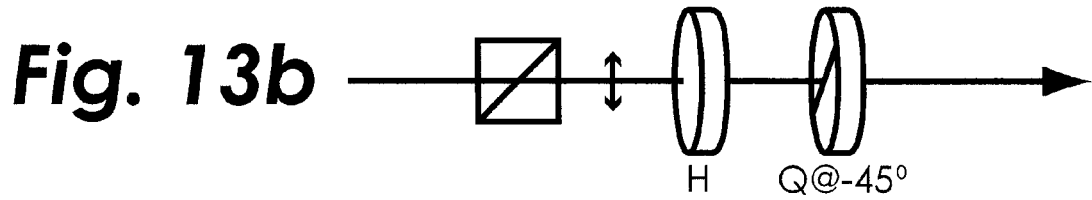
FIG. 13b is a schematic representation of a configuration for the incident optical pathway (the arrow represents the direction of the light beam) with the polarizer set to pass p-polarizer light, rotating half wave plate and quarter wave plate at +45°.

In configuration A, two different combinations (pol set to pass s-polarized with Q=−45° (FIG. 13a) and pol set to pass p-polarized with Q=45° (FIG. 13b)) yield identical incident electric fields as a function of $\alpha_H^\omega$. Substituting the appropriate Jones matrices and performing the matrix multiplication yields the following expression for the polarization of the light in terms of the rotation angle of the half wave plate.

$$e^\omega = \begin{bmatrix} \exp(-i2\alpha_H^\omega) \\ i\exp(i2\alpha_H^\omega) \end{bmatrix} \quad (67)$$

Configuration B

Figure 13C:
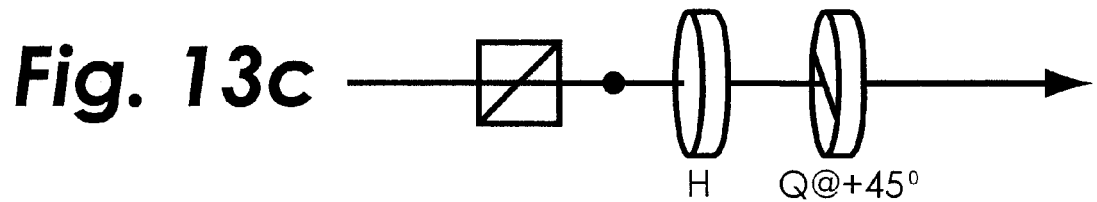
FIG. 13c is a schematic representation of a configuration for the incident optical pathway (the arrow represents the direction of the light beam) with the polarizer set to pass s-polarizer light, rotating half wave plate and quarter wave plate at +45°.
Figure 13D:
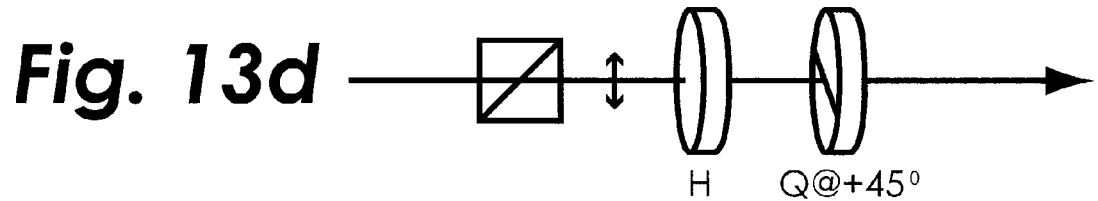
FIG. 13d is a schematic representation of a configuration for the incident optical pathway (the arrow represents the direction of the light beam) with the polarizer set to pass p-polarizer light, rotating half wave plate and quarter wave plate at −45°.

By analogy with configuration A, two different combinations (pol set to pass s-polarized with Q=45° (FIG. 13c) and pol set to pass p-polarized with Q=−45° (FIG. 13d)) yield identical incident electric fields.

$$e_{sample}^\omega = \begin{bmatrix} \exp(-i2\alpha_H^\omega) \\ -i\exp(-i2\alpha_H^\omega) \end{bmatrix} \quad (68)$$

Modular Assembly of the Complete Optical Path

The modular relations described in the previous sections can be combined for a given instrumental configuration to determine the complete suite of $\chi^{(2)}$ tensor elements present in SHG. Combining the relations in Eq. 67 or Eq. 68 with Eq. 64 provides the fully complex-valued ρ parameter in terms of the $\chi^{(2)}$ tensor elements and the rotation angle optics that define the polarization of the incident light.

Case 1—Uniaxial Chiral Films Using Configuration A

In SHG measurements of uniaxially oriented films, substitution of the Jones vector for the optical field in Eq. 64 yields the following expression for ρ as a function of $\alpha_H^\omega$.

$$\rho(\alpha_H^\omega) = \frac{\chi_{ppp}\exp(-i4\alpha_H^\omega) + i\chi_{psp} - \chi_{pss}\exp(i4\alpha_H^\omega)}{\chi_{spp}\exp(-i4\alpha_H^\omega) + i\chi_{spp}} \quad (69)$$

Evaluation of $\rho(\alpha_H^\omega)$ for Configuration A with $\alpha_H^\omega$=−22.5°, 0°, 22.5°, and 45° (corresponding to plane polarized with the polarization plane oriented +45°, right circularly polarized, plane polarized with the polarization plane oriented −45°, and left circularly polarized, respectively), results in the following set of expressions for the effective tensor elements, derived hereinbelow in the Supporting Calculations section.

$$\frac{\chi_{spp}}{\chi_{ssp}} = \frac{\Sigma_{R/L} - \Sigma_{+/-}}{i\Delta_{R/L} + \Delta_{+/-}} \quad (70a)$$

$$\frac{\chi_{psp}}{\chi_{ssp}} = \frac{1}{2}\left[\Sigma_{+/-} + \frac{\chi_{spp}}{\chi_{ssp}}\Delta_{+/-}\right] \quad (70b)$$

$$\frac{\chi_{pss}}{\chi_{ssp}} = \frac{1}{4}\left[(\Delta_{+/-} - i\Delta_{R/L}) + \frac{\chi_{spp}}{\chi_{ssp}}(\Sigma_{+/-} - \Sigma_{R/L})\right] \quad (70c)$$

$$\frac{\chi_{pss}}{\chi_{ssp}} = \frac{1}{4}\left[(\Delta_{+/-} + i\Delta_{R/L}) + \frac{\chi_{spp}}{\chi_{ssp}}(\Sigma_{+/-} + \Sigma_{R/L})\right] \quad (70d)$$

A shorthand notation has been introduced, in which $\Sigma_{+/-}=\rho(-22.5°)+\rho(22.5°)$, $\Sigma_{R/L}=\rho(0°)+\rho(45°)$, $\Delta_{+/-}=\rho(-22.5°)-\rho(22.5°)$, and $\Delta_{R/L}=\rho(0°)-\rho(45°)$. From experimental measurements of the null angles obtained for these four different incident polarization states, relative values of all five nonzero effective $x^{(2)}$ tensor elements can be uniquely obtained with full phase information.

Case 2—Uniaxial Chiral Films Using Configuration B

The expressions for the effective $x^{(2)}$ tensor elements in measurements acquired using Configuration B are exactly identical to that for Configuration A in Eq. 70 except $\rho(45°)$ now corresponds to right circularly polarized light and $\rho(0°)$ corresponds to left circularly polarized light (i.e., making the substitution $\Delta_{R/L}=\rho(45°)-\rho(0°)$ in Eq. 70).

Case 3—Uniaxial Achiral Films Using Configuration A

In SHG measurements of uniaxial achiral films, the expressions in Eq. 70 simplify considerably. In the absence of chirality, $\rho(45°)=-\rho(0°)$ and $\rho(-22.5°)=-\rho(22.5°)$. Consequently, the set of complex-valued $x^{(2)}$ tensor elements can be obtained from ellipsometry measurements performed for just two incident polarization states ($\alpha_H^\omega=0°$ and $\alpha_H^\omega=22.5°$) corresponding to right circularly polarized light and linearly polarized light oriented at $-45°$.

$$\frac{\chi_{pss}}{\chi_{ssp}} = -\frac{1}{2}[\rho(22.5°) + i\rho(0°)] = \frac{s_6 \chi_{ZXX}}{s_1 \chi_{XXZ}} \quad (71)$$

$$\frac{\chi_{ppp}}{\chi_{ssp}} = -\frac{1}{2}[\rho(22.5°) - i\rho(0°)] = \frac{+s_3}{s_1} + \frac{s_5 \chi_{ZXX}}{s_1 \chi_{XXZ}} + \frac{s_7 \chi_{ZZZ}}{s_1 \chi_{XXZ}} \quad (72)$$

Case 4—Uniaxial Achiral Films Using Configuration B

By analogy with Case 3, simplification of Eq. 70 in the absence of chirality yields the following two compact relations, differing only from the expressions for Configuration A in the sign of the $i\rho(0°)$ term.

$$\frac{\chi_{pss}}{\chi_{ssp}} = -\frac{1}{2}[\rho(22.5°) - i\rho(0°)] = \frac{s_6 \chi_{ZXX}}{s_1 \chi_{XXZ}} \quad (73)$$

$$\frac{\chi_{ppp}}{\chi_{ssp}} = -\frac{1}{2}[\rho(22.5°) + i\rho(0°)] = \frac{+s_3}{s_1} + \frac{s_5 \chi_{ZXX}}{s_1 \chi_{XXZ}} + \frac{s_7 \chi_{ZZZ}}{s_1 \chi_{XXZ}} \quad (74)$$

Relationships between SHG-ORD, SHG-CD, SHG-LD and Nonlinear Optical Ellipsometry Several experimental methods have been developed for probing the large chiral effects routinely observed in SHG and SFG measurements of thin surface layers. For example, SHG circular dichroism (SHG-CD) is a measurement of the intensity difference detected for left (L) vs. right (R) circularly polarized incident light. In related measurements, SHG linear dichroism (SHG-LD) is the difference between SHG intensities generated for plane polarized light with the axis of polarization oriented $-45°$ and $+45°$. The relationships between the measured SHG-CD and SHG-LD ratios and the surface tensor elements are summarized below.

$$R_i^{CD} = \frac{I_{i,L}^{2\omega} - I_{i,R}^{2\omega}}{\frac{1}{2}(I_{i,L}^{2\omega} + I_{i,R}^{2\omega})} = 4\frac{Im(\chi_{isp}\chi_{ipp}^*)}{|\chi_{isp}|^2 + |\chi_{ipp}|^2} \quad (75)$$

$$R_i^{LD} = \frac{I_{i,-45°}^{2\omega} - I_{i,45°}^{2\omega}}{\frac{1}{2}(I_{i,-45°}^{2\omega} + I_{i,45°}^{2\omega})} = 4\frac{Re(\chi_{isp}\chi_{ipp}^*)}{|\chi_{isp}|^2 + |\chi_{ipp}|^2} \quad (76)$$

In Eqs. 75 and 76, $I^{2\omega}$ is the detected intensity of the frequency doubled beam, with the subscripts indicating the detected polarization component i (either s or p) generated for a given incident polarization state, and effective tensor elements are used, which are linear combinations of the surface tensor elements and geometric and Fresnel factors relating the incident and exigent electric fields to the fields within the interfacial layer (explicit expressions for the effective tensor elements are given elsewhere herein). SHG optical rotary dispersion (SHG-ORD), in which chiral contributions result in rotation of the primary polarization axis of the exigent beam, is closely related to both SHG-CD and SHG-LD. In SHG-ORD measurements, a polarizer is placed between the sample and the detector and the intensity is recorded as a function of the polarizer rotation angle. Fitting the detected SHG intensity to the following expression yields the SHG-ORD rotation angle $\phi$.

$$I^{2\omega} = F + G\cos^2(\alpha_{pol} - \phi) \quad (77)$$

SHG-ORD measurements are typically performed with a p-polarized incident beam to simplify their interpretation, in which case $\phi_p$ is zero in the absence of surface chirality in uniaxially oriented films. Clearly, in SHG-CD, SHG-LD, and SHG-ORD measurements of interfacial chirality, the relative phase shifts between the effective tensor elements are critical aspects of all of the measured parameters, but this phase information is generally unavailable using most existing intensity-based polarization analysis techniques.

Given that SHG-ORD experimental measurements are actually just rotating analyzer ellipsometry measurements acquired with a p-polarized incident beam, one would expect to find simplifying relationships connecting SHG-ORD with SHG-RAE and SHG-RHE. The general expression for SHG-RAE in Eq. 56a differs from that given in Eq. 77, but the two expressions can be shown to be equivalent through the following substitutions.

$$A = \frac{1}{2}G\cos(2\phi) \quad (78a)$$

$$B = \frac{1}{2}G\sin(2\phi) \quad (78b)$$

$$C = F + \frac{1}{2}G \quad (78c)$$

Correspondingly, the rotation angle of the primary polarization axis for a p-polarized fundamental beam $\phi_p$ is related to the $x^{(2)}$ tensor elements through the following expression.

$$\tan(2\phi_p) = \frac{B}{A} = \frac{2Re(\chi_{ppp}\chi_{spp}^*)}{|\chi_{ppp}|^2 + |\chi_{spp}|^2} \quad (79)$$

From inspection of Eqs. 75, 76, and 79, it is clear that precise knowledge of the complex-valued effective tensor elements with phase information allows prediction of SHG-ORD as well as SHG-CD and SHG-LD, but the opposite is not necessarily true.

Molecular Orientation Information

In planar chromophores with pseudo-$C_{2v}$ symmetry, excited states can be either $B_1$-like, in which $\beta_{x'x'z'}$ is the only symmetry allowed element of the molecular tensor, or $A_1$-like, in which $\beta_{z'z'z'}$ and $\beta_{z'x'x'}$ dominate the molecular response. Explicit evaluation of Eq. 29 for a uniaxial surface system yields the following orientation average connecting the molecular nonlinearity to the nonlinear optical properties of the surface given by the $\chi^{(2)}$ tensor in a planar chromophore of $C_{2v}$ symmetry.

$$\chi_{ZZZ} = N_s[\langle\cos^3\theta\rangle\beta_{z'z'z'} + \langle\sin^2\theta\cos\theta\cos^2\psi\rangle(\beta_{z'x'x'} + 2\beta_{x'x'z'})] \quad (80)$$

$$\chi_{ZXX} = \tfrac{1}{2}N_s[\langle\sin^2\theta\cos\theta\rangle\beta_{z'z'z'} + \langle\cos\theta\rangle\beta_{z'x'x'} - \langle\sin^2\theta\cos\theta\cos^2\psi\rangle(\beta_{z'x'x'} + 2\beta_{x'x'z'})] \quad (81)$$

$$\chi_{XXZ} = \tfrac{1}{2}N_s[\langle\sin^2\theta\cos\theta\rangle\beta_{z'z'z'} + \langle\cos\theta\rangle\beta_{x'x'z'} - \langle\sin^2\theta\cos\theta\cos^2\psi\rangle(\beta_{z'x'x'} + 2\beta_{x'x'z'})] \quad (82)$$

$$\chi_{XYZ} = \tfrac{1}{2}N_s[\langle\sin^2\theta\sin\psi\cos\psi\rangle(\beta_{x'x'z'} - \beta_{z'x'x'})] \quad (83)$$

In Eqs. 80–83, $N_s$ is the surface number density, $\theta$ is the tilt angle of the z'-axis away from the surface normal, and $\psi$ is the twist angle of the x'-axis. In systems exhibiting a random distribution in the twist angle $\psi$, an orientation parameter D can be defined by combination of the expressions in Eq. 80–83. For transitions to states of $A_1$-like symmetry in planar chromophores, the tensor elements $\beta_{z'z'z'}$ and $\beta_{z'x'x'}$ will dominate the molecular response, leading to the following expression for the orientation parameter D.

$$D = \frac{\langle\cos^3\theta\rangle}{\langle\cos\theta\rangle} = \frac{\chi_{ZZZ} - \chi_{ZXX} + \chi_{XXZ}}{\chi_{ZZZ} - \chi_{ZXX} + 3\chi_{XXZ}} \quad (84)$$

For transitions to states of $B_1$-like symmetry, only $\beta_{x'x'z'} = \beta_{x'z'x'}$ remain, leading to the following expression for the orientation parameter D.

$$D = \frac{\langle\cos^3\theta\rangle}{\langle\cos\theta\rangle} = \frac{\chi_{ZZZ} + 2\chi_{ZXX} - 2\chi_{XXZ}}{\chi_{ZZZ} + 4\chi_{ZXX} - 2\chi_{XXZ}} \quad (85)$$

From the orientation parameter D, an apparent orientation angle ($\theta^*$) can be defined as the angle calculated if a $\delta$-function orientation distribution in $\theta$ is assumed.

$$\theta^* = \arccos|D|^{1/2} \quad (86)$$

It is worth emphasizing that the assumptions of a broad distribution in the twist angle $\psi$ and a $\delta$-function distribution in $\theta$ should be used with caution. Experimental measurements of chiral and achiral systems have demonstrated that both approximations routinely fail in oriented thin surface films.

Excited State Information

Under most experimental conditions, the molecular polarizability tensor $\beta^{(2)}$ in Eq. 29 can be expressed in terms of simple, intuitive molecular properties. In SFG and SHG measurements in which an incident frequency is resonant with a real transition within the surface chromophore, including vibrational SFG investigations, the resonant molecular nonlinear polarizability simplifies to the product of the transition moment and the anti-Stokes Raman polarizability tensor (shown in Eq. 87 for ir-vis SFG, with the underscore indicating the resonant interaction).

$$\beta_{i'j'k'}(-\omega_{sum};\omega_{vis},\underline{\omega_{ir}}) = \frac{-1}{\hbar}\sum_n \frac{(\alpha_{0n}^{i'j'})_{AR}\mu_{n0}^{k'}}{(\omega_n - \omega_{ir} - 2i\Gamma_n)} \quad (87)$$

Under conditions in which the states dominating the molecular nonlinear optical response lie near or higher in energy than the sum frequency, including most SHG measurements, the nonlinear polarizability of the chromophore simplifies to the product of the transition moment and the tensor for two-photon absorption (TPA), shown in Eq. 88.

$$\beta_{i'j'k'}(\underline{-2\omega};\omega,\omega) = \frac{-1}{2\hbar}\sum_n \frac{\mu_{n0}^{i'}(\alpha_{n0}^{j'k'})_{TPA}}{(\omega_n - 2\omega - 2i\Gamma_n)} \quad (88)$$

Using the relations in Eq. 29, 87, and 88, reliable measurements of the macroscopic nonlinear polarizability described by the $\chi^{(2)}$ tensor elements can provide rich information about both molecular orientation and the nonlinear polarizability of the chromophore.

The expression in Eq. 88 indicates that information related to the tensor for two-photon absorption (TPA) can be obtained from polarization analysis of SHG measurements. In the case of SHG resonant with $A_1$-like excited states, the depolarization ratio of the TPA tensor $R = \alpha_{x'x'}/\alpha_{z'z'}$ can be obtained directly from appropriate combinations of $\chi^{(2)}$ tensor elements given in Eqs. 80–82.

$$R = \frac{2\chi_{ZXX} - 2\chi_{XXZ}}{\chi_{ZZZ} + 2\chi_{XXZ}} = \frac{\beta_{z'x'x'}}{\beta_{z'z'z'}} = \frac{\alpha_{x'x'}}{\alpha_{z'z'}} \quad (89)$$

From Eq. 89, measurements of the ratio R yield information on the polarization characteristics of TPA that is analogous to the depolarization ratio.

10. EXAMPLE 4

All experiments in this Example 4 were performed on the instrument of FIG. 1. The optical pathway consisted of Nd:YAG laser source 12 (New Wave Research Polaris, 1064 nm, 5–7 ns pulses, 20 Hz, ~1 mJ/pulse, available from New Wave Research, Inc., 48660 Kato Road, Fremont, Calif. 94538) followed by a half wave plate 16/Glan laser prism 18 combination for attenuation of the fundamental beam. A computer-controlled rotating half wave plate 20 and fixed quarter wave plate 22 ($\alpha_Q^\omega = -45°$) controlled the incident polarization. A lens 24 and visible blocking filter 26 preceded the sample cell 28. An infrared absorbing filter 42 and a collimating lens 44 followed the sample cell 28. A polarizing beam splitting cube 50 allowed separation and detection of both the s- and p-polarized components of the beam after passage through the wave plates. An infrared filter 52,53 and a 532 nm interference filter 54,55 preceded each photomultiplier tube 56,57 (Burle 8850, available from Burle Industries, Inc., 1000 New Holland Avenue, Lancaster, Pa. 17601-5688) for the detection of the second harmonic wavelength at 532 nm. The addition of the second detector 57 allowed for the simultaneous monitoring of both polarization components separated at the polarizing beamsplitter 50.

NONE, SHG-RQE, SHG-RHE, and SHG-ORD measurements were performed for both fluorescein isothiocyanate labeled bovine serum albumin (FITC-BSA, available from Sigma-Aldrich Chemical Co., Milwaukee, Wis.) and rhodamine B labeled dextran, ~70,000 MW (RB-dex, available from Molecular Probes, Inc., 29851 Willow Creek Road, Eugene, Oreg. 97402) surface layers. FITC-BSA interfaces were prepared by exposure of a cleaned fused silica prism surface to approximately 1 mg/mL FITC-BSA in a 0.01 M phosphate buffered saline (PBS) buffer using ultrapure water (Barnstead NANOpure system, available from Barnstead International, 2555 Kerper Boulevard, Dubuque, Iowa 52001-1478). RB-dex interfaces were generated by exposure to approximately 1 mg/mL RB-dex prepared in ultrapure water. In both systems, all measurements were performed with the prism in contact with the aqueous solutions.

SHG polarization measurements of model achiral interfaces were performed using dyes with absorbance maxima corresponding to on-, near-, and off-resonance with the second harmonic of the beam. Solutions of $5.0 \times 10^{-4}$ M Rhodamine 6G (R-6G, available from Sigma-Aldrich Chemical Co., Milwaukee, Wis., ~99% pure, $\lambda_{max}$=529.5 nm, $\epsilon_m$=110,000 cm$^{-1}$M$^{-1}$) in ultrapure water, $1.0 \times 10^{-4}$ M disperse red 19 (DR-19, available from Sigma-Aldrich Chemical Co., Milwaukee, Wis., ~95% pure, $\lambda_{max}$=475.2 nm, $\epsilon_m$=27,000 cm$^{-1}$M$^{-1}$) in 2-propanol (Mallinckrodt, HPLC grade, available from Mallinckrodt Baker, Inc., Red School Lane, Phillipsburg, N.J.), and $5.0 \times 10^{-6}$ 1-docosyl-4-(4-hydroxystyryl) pyridinium bromide (DPB, available from Sigma-Aldrich Chemical Co., Milwaukee, Wis., $\lambda_{max}$=397.3 nm, $\epsilon_m$=27,000 cm$^{-1}$M$^{-1}$; $\lambda_{max}$=574.0 nm, $\epsilon_m$=5,500 cm$^{-1}$M$^{-1}$) in dichloromethane (Mallinkrodt, SpectraAR grade, available from Mallinckrodt Baker, Inc., Red School Lane, Phillipsburg, N.J.) were prepared. All measurements were performed in total internal reflection with the prism surface in direct contact with the solution. Measurements using dichloromethane were performed using a BK-7 glass prism 30 to ensure total internal reflection.

Two different sample cells 28 were used in the experiments. For the R-6G, DR-19, FITC-BSA, and RB-dex solutions, the sample cell 28 consisting fused silica prism 30, rubber o-ring 32, and ½-in square aluminum plate 34 with an ⅛-in hole 38, for sample addition/removal, held secure using mount clamps (1 in=2.54 cm). The volatility of the dichloromethane necessitated a closed sample chamber, constructed using a piece of aluminum 34 (1 in×¾-in×½-in) containing a small ample well (⅜-in diameter and ⅛-in depth) sealed to a BK-7 prism 30 surface with a Teflon® o-ring 32.

Null angles were obtained using a computer software program written in house. The quarter wave plate 46 and half wave plate 48 along the detection pathway were positioned in computer controlled mounts (Newport SR50CC, with a Newport Universal Motion Controller/Driver, available from Newport Corporation, 1791 Deere Avenue, Irvine, Calif. 92606). In a given NONE measurement, approximate values for the minimum angles were first determined by manual rotation of the wave plates as described previously. Precise null angles were subsequently obtained by first recording the SHG intensity as a function of the quarter wave plate 46 rotation angle with the half wave plate 48 fixed and fitting the resulting response to the following general equation.

$$P^{2\omega}=A \cos (4\alpha_H^{2\omega}+\delta_A)+B \cos (2\alpha_H^{2\omega}+\delta_B)+C \qquad (90)$$

The nonlinear curve fitting to Eq. 90 was used solely to identify the intensity minima. The angle providing a minimum intensity of SH light was calculated from the Fourier coefficients A and B. The quarter wave plate was then fixed at this minimum angle and the half wave plate was rotated while mapping the intensity of the signal. The resulting curve was fit to Eq. 91 (the predicted response for a half wave plate).

$$P^{2\omega}=A \cos (4\alpha_H^{2\omega}-\delta)+C \qquad (91)$$

Figure 14:
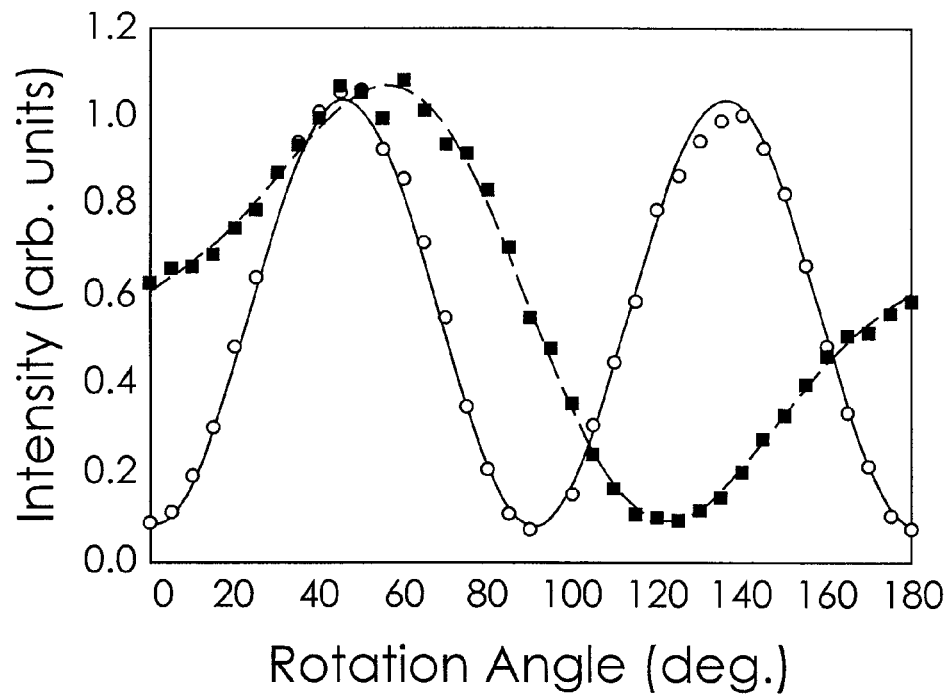
FIG. 14 is a graph of the second harmonic intensity for DR-19 measured using the methods of the present invention using various rotations of the half wave plate and the quarter wave plate of FIG. 1.
Figure 15:
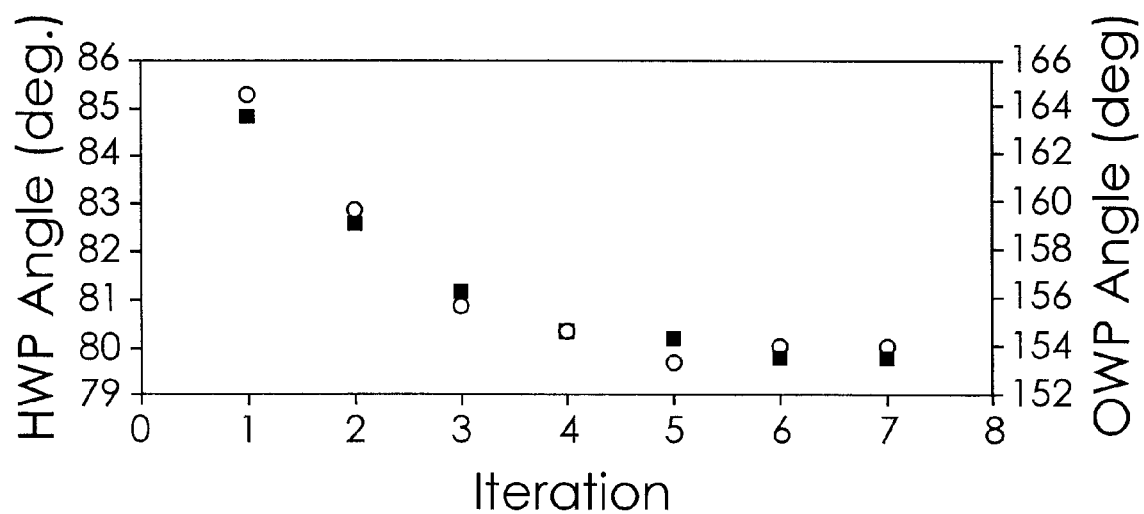
FIG. 15 is a plot of experimentally determined minimum angles for the iterative approach using automated NONE of the present invention.

FIG. 14 illustrates the second harmonic plot of DR-19 fitted to Eqs. 90–91. The open circles represent the observed intensities while rotating the half wave plate 48 with a fixed quarter wave plate 46. The solid squares represent the rotating quarter wave plate 46 with a fixed half wave plate 48. The lines represent the fitted data to the appropriate equations. The half wave plate 48 was fixed at the intensity minimum and the process was iteratively repeated until the values obtained for the null angles no longer changed significantly, a representative example of which is provided in FIG. 15. In FIG. 15, the open circles represent the half wave plate angles and the solid squares represent the quarter wave plate angles. The iterations converge to the reported null angles, which were determined to be 79.9° (±0.2°) and 153.8° (±0.5°) for the half and quarter wave plates, respectively. Reported errors are from 3–5 measurements.

SHG-RHE and SHG-RQE measurements were made using the same computer software. For the SHG-RHE experiments, the second harmonic beam passed through a rotating half wave plate 48 and then through a fixed polarizer 50. The half wave plate 48 was rotated over 360° and the intensity of both s- and p-polarizations of light after the polarizer 50 were measured using PMTs 56,57. The data acquired on the PMTs 56,57 were both fit to Eq. 59. Parameters obtained from these fits were used in to determine the respective ρ values. Errors were derived from the averages of 3–5 fits. For the SHG-RQE measurements, the second harmonic beam was passed through a rotating quarter wave plate 46 and fixed polarizer 50. Both s- and p-polarizations were measured and fit to Eq. 61a. Errors were derived from the averages of 3–5 fits.

Molecular modeling calculations of DR-19, R-6G, and DPB were performed using Gaussian 98. Geometry optimization was performed using either restricted Hartree-Fock method with a STO-3G basis set (DPB and DR-19) or with the restricted b31yp density functional theory method with the 6-31G basis set. Excited state calculations performed on the optimized structure were done with restricted ZINDO including the contributions from 100 excited states in determination of the TPA tensors. The calculations for the TPA tensors (or equivalently, the hyperpolarizability tensors) for SHG required summation of the contributions of the first ~100 excited states in order to obtain satisfactory convergence.

Values for the ellipsometric parameters ρ were obtained using several different nonlinear optical ellipsometric approaches and instrumental configurations. Table 12 contains the tabulated ρ values acquired using NONE for the resonant, near-resonant, and off-resonant achiral molecular systems, R-6G, DR-19, and DPB, respectively.

TABLE 12

Summary of null angles and determined ρ values

| | R-6G | DR-19 | DPB |
|---|---|---|---|
| $\alpha_Q^\omega = 0°$ | * | 129.2° (±0.7°) | −33.3° (±0.9°) |
| $\alpha_H^\omega = 0°$ | * | 4.6° (±0.1°) | 16.3° (±0.9°) |
| $\alpha_Q^\omega = 22.5°$ | 112.8° (±0.5°) | 153.8° (±0.5°) | 161.4.5° (±0.8°) |
| $\alpha_H^\omega = 22.5°$ | 154.7° (±0.3°) | 79.9° (±0.2°) | −2.5° (±0.3°) |
| $\rho_0$ | 0.00 (±0.03) − 0.99i (±0.03i) | 0.55 (±0.03) − 0.963i (±0.002i) | 0.48 (±0.03) − 0.59i (±0.04i) |
| $\rho_{22.5}$ | −0.38 (±0.02) + 0.345i (±0.005i) | −1.92 (±0.05) − 0.515i (±0.002i) | −1.86 (±0.07) − 1.57i (±0.09i) |

*The wave plate angles for R-6G did not converge for an incident polarization when $\alpha_H^\omega = 0°$. The production of nearly perfectly circularly polarized light yields a near infinite number of angles which produce null values.

Figure 16:
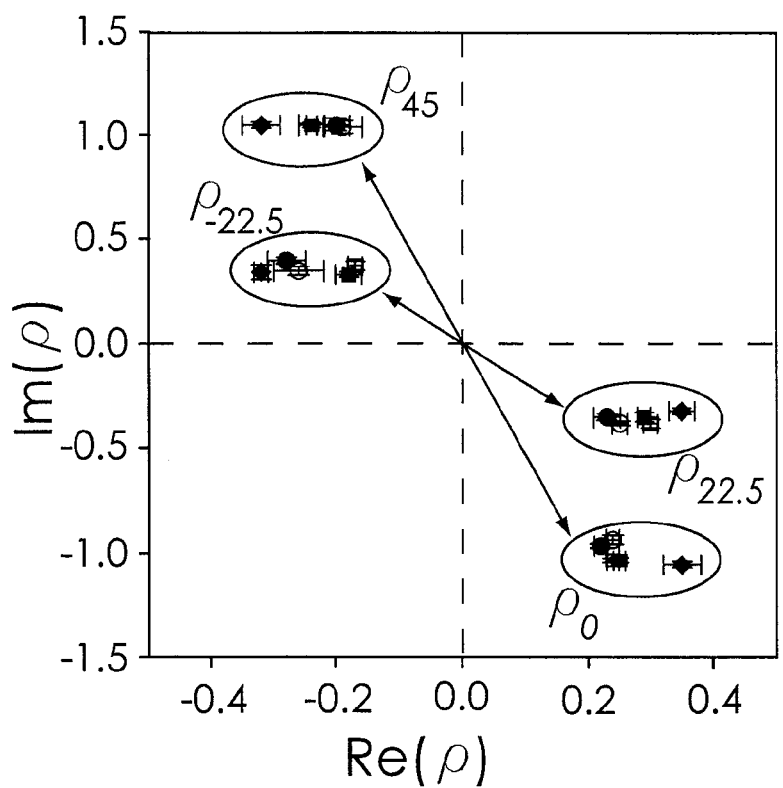
FIG. 16 is a graph of extracted ρ values for rhodamine labeled dextran used to compare different polarization detection techniques.
Figure 17:
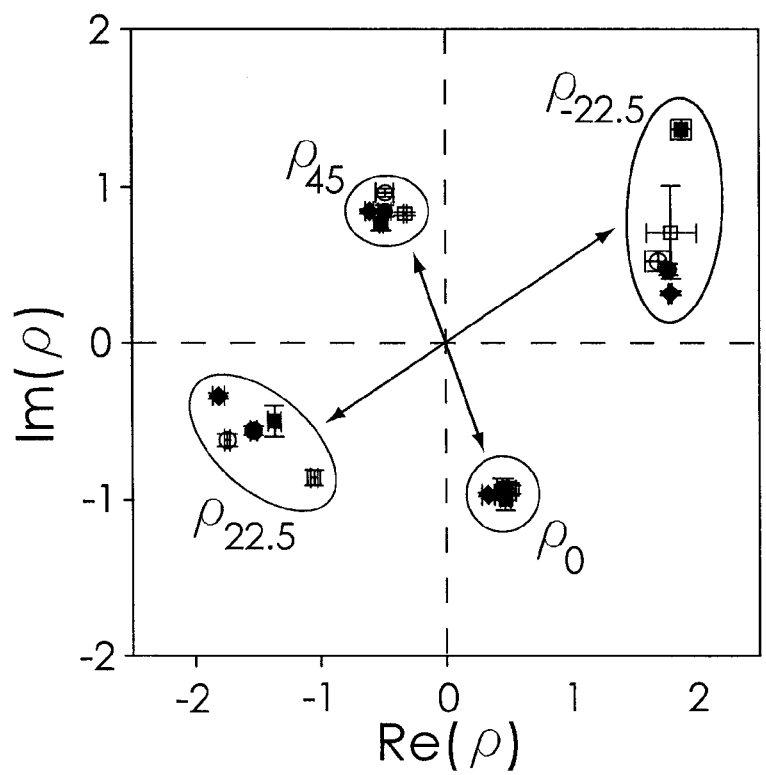
FIG. 17 is a graph of extracted ρ values for FITC-BSA used to compare different polarization detection techniques.

FIGS. 16 and 17 contain a summary of the ρ values measured from two chiral surfaces (RB-dex and FITC-BSA, respectively) using three of the ellipsometric methods described hereinabove. Tables 13 and 14 disclose these ρ values.

TABLE 13

Comparison of FITC-BSA ρ values derived from different experimental configurations.

| | $\rho_{-\pi/8}$ | $\rho_{\pi/8}$ | $\rho_0$ | $\rho_{\pi/4}$ |
|---|---|---|---|---|
| NONE | 1.80 (±.01) + 0.31i (±.01i) | −1.80 (±.05) − 0.34i (±.01i) | 0.33 (±.05) − 0.97i (±.01i) | −0.59 (±.04) + 0.84i (±.01i) |
| Rot QWP s- | 1.78 (±.02) + 0.46i (±.04i) | −1.53 (±.02) − 0.56i (±.03i) | 0.45 (±.04) − 0.93i (±.06i) | −0.47 (±.05) + 0.84i (±.04i) |
| Rot QWP p- | 1.7 (±.1) + 0.51i (±.06i) | −1.74 (±.02) − 0.62i (±.04i) | 0.48 (±.03) − 0.95i (±.06i) | −0.47 (±.07) + 0.96i (±.02i) |
| Rot HWP s- | 1.89 (±.08) ± 1.36i (±.06i) | −1.36 (±.05) ± 0.5i (±.1i) | 0.47 (±.04) ± 1.00i (±.07i) | −0.50 (±.01) ± 0.76i (±.05i) |
| Rot HWP p- | 1.8 (±.2) ± 0.7i (±.3i) | −1.05 (±.03) ± 0.86i (±.05i) | 0.52 (±.03) ± 0.94i (±.03i) | −0.32 (±.01) ± 0.82i (±.01i) |

TABLE 14

Comparison of RB-dex ρ values derived from different experimental configurations.

| | $\rho_{-\pi/8}$ | $\rho_{\pi/8}$ | $\rho_0$ | $\rho_{\pi/4}$ |
|---|---|---|---|---|
| NONE | −0.32 (±.01) + 0.35i (±.01i) | 0.35 (±.02) − 0.32i (±.01i) | 0.35 (±.03) − 1.05i (±.01i) | −0.32 (±.03) + 1.05i (±.01i) |
| Rot QWP s- | −0.28 (±.03) + 0.40i (±.01i) | 0.23 (±.02) − 0.35i (±.01i) | 0.22 (±.01) − 0.96i (±.01i) | −0.20 (±.02) + 1.05i (±.03i) |
| Rot QWP p- | −0.26 (±.04) + 0.35i (±.02i) | 0.25 (±.01) − 0.38i (±.01i) | 0.24 (±.01) − 0.93i (±.02i) | −0.19 (±.03) + 1.04i (±.03i) |
| Rot HWP s- | −0.18 (±.02) ± 0.33i (±.01i) | 0.29 (±.01) ± 0.35i (±.02i) | 0.25 (±.01) ± 1.03i (±.01i) | −0.24 (±.01) ± 1.05i (±.01i) |
| Rot HWP p- | −0.17 (±.01) ± 0.37i (±.02i) | 0.30 (±.01) ± 0.38i (±.02i) | 0.24 (±.01) ± 1.03i (±.01i) | −0.24 (±.02) ± 1.04i (±.01i) |

In FIG. 16, extracted ρ values for rhodamine labeled dextran are used to compare the polarization detection techniques where diamonds represent NONE, squares represent RHE, and circles represent RQE (for both RHE and RQE solid symbols are the values obtained from the s-detected fit and the open symbols are from the p-detected fit). Circled groups represent the ρ value obtained for the detection setups when using the same incident polarization (noted on the graph).

In FIG. 17, extracted ρ values for FITC-BSA are used to compare the polarization detection techniques where diamonds represent NONE, squares represent RHE, and circles represent RQE (for both RHE and RQE solid symbols are the values obtained from the s-detected fit and the open symbols are from the p-detected fit). Circled groups represent the ρ value obtained for the detection setups when using the same incident polarization (noted on the graph).

In both the SHG-RQE and SHG-RHE measurements, the use of the instrument depicted in FIG. 1 allowed for the simultaneous acquisition of data using both configurations.

As can be seen by inspection of Table 12 and FIGS. 16 and 17, similar values for ρ were obtained for all of the different measurement approaches.

Figure 18A:
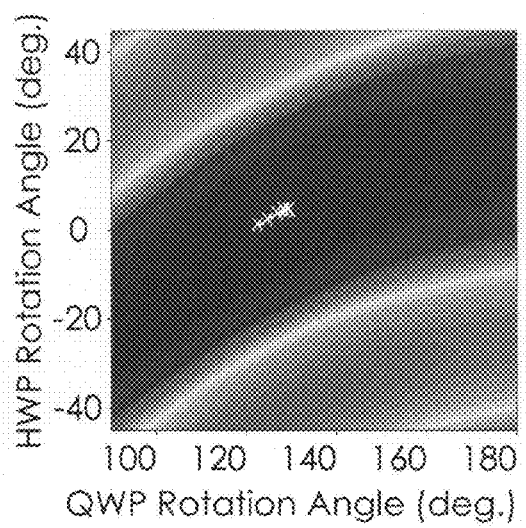
FIGS. 18a–d are plots of the predicted intensities calculated as a function of the exigent half wave plate and quarter wave plate rotation angles for a DR-19 monolayer film as measured according to the present invention.
Figure 18B:
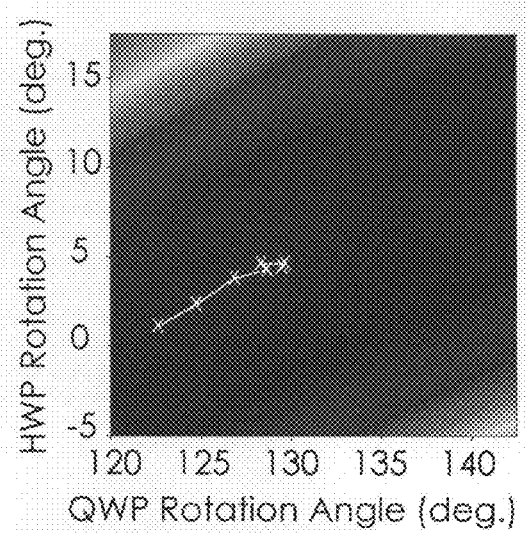
Figure 18C:
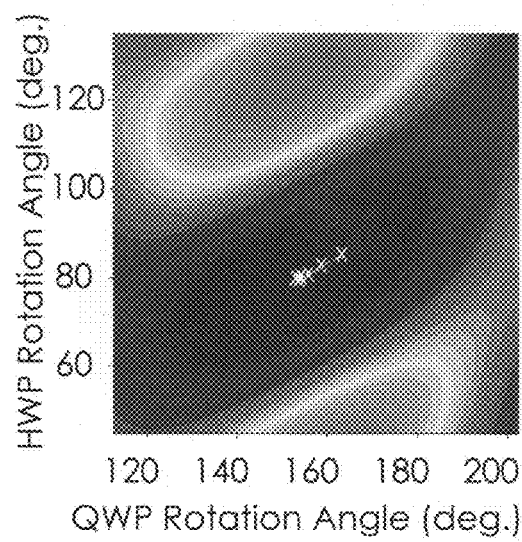
Figure 18D:
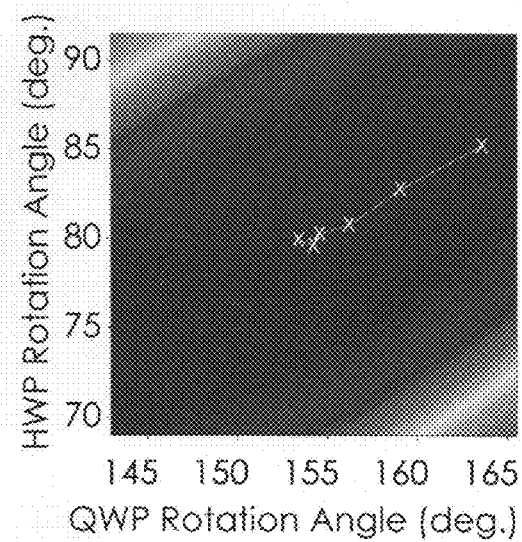

Analogous to knowledge of the wavefunctions in quantum mechanics, knowledge of the set of complex ρ values (two in SHG measurements of uniaxial achiral interfaces and four in chiral interfaces) allows for the prediction of the detected intensity expected for any combination of incident and exigent wave plates. Appropriate combinations of the ρ values yield the effective $\chi^{(2)}$ tensor elements that describe the nonlinear optical susceptibility of the interfacial layer, retaining relative phase information (e.g., in Eq. 71). The effective $\chi^{(2)}$ tensor elements are independent of the particular model used to relate the incident and exigent optical fields to the fields within the interfacial layer (i.e., the Fresnel factors). From these effective tensor elements, the predicted intensities were calculated as a function of the exigent half wave plate and quarter wave plate rotation angles for a DR-19 monolayer film, shown in FIGS. 18a and b for $\alpha_H=0°$ and in FIGS. 18c and d for $\alpha_H=22.5°$. Superimposed on the calculated intensity "surfaces" are the experimental data demonstrating the iterative convergence to the intensity null angle minima in the NONE measurements. The only information required to generate the full set of intensity surfaces shown in the figures (as well as for the construction of analogous plots for any different incident polarization state) was the locations of the two minima shown in the figure and highlighted in the expanded views. Analogous surfaces for the chiral systems can be constructed from the combined set of four $\rho$ values.

Figure 19:
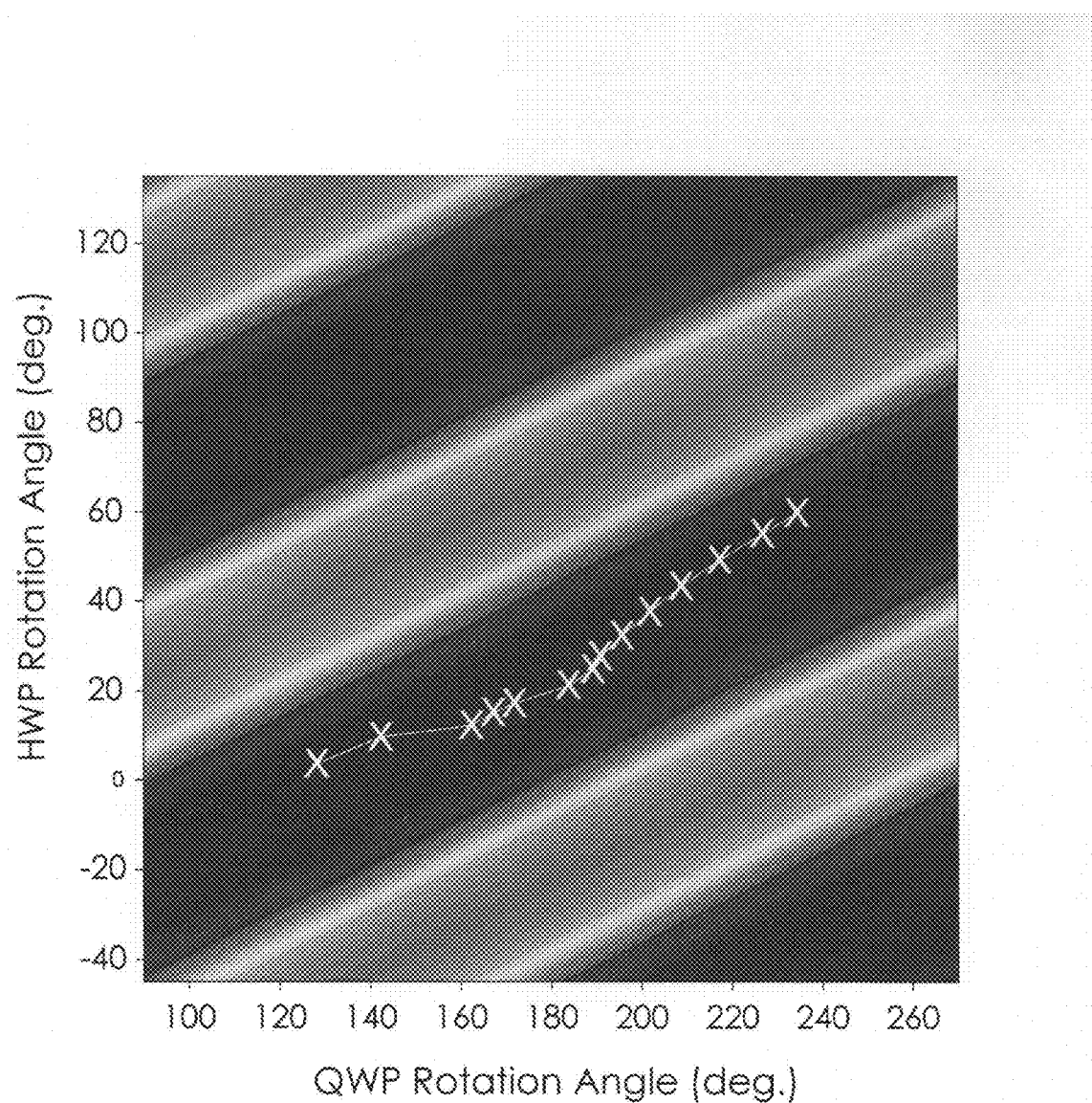
FIG. 19 is a predicted intensity map of the second harmonic signal for R-6G at an incident polarization of $\alpha_H=0°$ and $\alpha_Q=-45°$.

In one particularly interesting case, the null angles for a silica surface in contact with the R-6G solution did not converge after multiple iterations with a right circularly polarized incident beam (see FIG. 19). This poor convergence can be understood by inspection of the parameters describing the polarization state of the frequency doubled beam. Under these conditions and for this sample, $\rho \cong 0-1i$ (Table 12) indicating that the exigent light is almost perfectly circularly polarized. The predicted intensity map of the second harmonic signal for this set of incident polarization conditions shown in FIG. 19 clarifies the reasons for the poor convergence. For purely circularly polarized light, any arbitrary rotation angle of the quarter wave plate generates purely linearly polarized light. Consequently the global minimum for the intensity surface for light that is nearly circularly polarized was so shallow that it could not be unambiguously identified within experimental error.

Combinations of the $\rho$ values using Eqs. 71–72 together with the Fresnel factors evaluated using a thin film model developed previously allowed for the determination of the $\chi^{(2)}$ tensor elements describing the resonant, near-resonant, and non-resonant achiral dye films, R-6G, DR-19, and DPB, respectively, which are compiled in Table 15.

ments yielded ratios of 1.00 (±0.04)–0.04i (±0.04i) and 1.34 (±0.01)+1.1i (±0.1i) for DR-19 and DPB, respectively. The results of the measurements for DR-19 and DPB are similar to those obtained using a manually nulled instrument, although the automated system provided more precise measurements than those obtained in earlier work.

Extraction of Orientation Information

The molecular orientation parameters D calculated for DR-19 and DPB (Eq. 84) and for R-6G (Eq. 85) are summarized in Table 15. In the limit of a broad orientation distribution and for resonance-enhancement with a single, spectrally resolved transition, a value of $D \cong 0.6+0i$ is expected. All three dyes produced predominantly real orientation parameters approximately equal to 0.6. The apparent orientation angles for R-6G, DR-19, and DPB calculated from the values for D were be 38.5° (±0.7°), 39.5° (±0.9°) and 43° (±2°), respectively, which are all within two standard deviations of the magic angle result of 39.2°, expected for a broad orientation distribution. For physisorbed dye molecules assembled at solid-liquid interfaces, it is entirely reasonable to expect a broad distribution in surface orientation angles. Recovery of the magic angle result in resonant, near-resonant, and off-resonant dyes of with significantly different symmetry properties and with no adjustable parameters supports the accuracy and reliability of the experimentally measured $\chi^{(2)}$ tensor elements.

Excited State Symmetry Information

The measured $\chi^{(2)}$ elements depend on both the molecular orientation and the molecular symmetry and provides a novel means of directly measuring the "depolarization ratio" of the TPA tensor. In the case of R-6G, the depolarization is relatively straightforward to evaluate by nature of the

TABLE 15

Summary of $\chi^{(2)}$ tensor elements and derived information

|  | R-6G | DR-19 | DPB |
|---|---|---|---|
| $\chi_{xxz}$ | 1 | 1 | 1 |
| $\chi_{zxx}$ | −0.64 (±0.03) + 0.37i (±0.03i) | 1.00 (±0.04) − 0.04i (±0.04i) | 1.34 (±0.01) + 1.1i (±0.1i) |
| $\chi_{zzz}$ | 1.42 (±0.01) − 0.24i (±0.04i) | 2.74 (±0.05) + 0.75i (±0.01i) | 2.43 (±0.07) + 1.75i (±0.09i) |
| $\chi_{zzz}/\chi_{zxx}$ | −1.81 (±0.02) − 0.7i (±0.1i) | 2.72 (±0.02) + 0.9i (0.1i) | 1.7 (±0.1) − 0.12i (±0.08i) |
| D | 0.61 (±0.01) − 0.05i (±0.01i) | 0.59 (±0.01) + 0.07i (±0.01i) | 0.52 (±0.02) + 0.07i (±0.04i) |
| θ* | 38.5° (±0.7°) | 39.5° (±0.9°) | 43° (±2°) |
| $R_{exp}$ | — | 0.00 (±0.02) + 0.02i (±0.01i) | −0.29 (±.02) − 0.21i (±0.03i) |
| $R_{cal}$ | — | −0.02 | −0.02 |

*All of the $\chi^{(2)}$ tensor elements are normalized to $\chi_{xxz}$.

Overall, the measured values are in good agreement with expectations based on symmetry analysis and quantum chemical calculations. For the resonant transition to the $B_1$ state in R-6G, the transition moment is oriented along the long axis (i.e., the x'-axis) and perpendicular to the $C_2$ axis (i.e., the z'-axis), in which case the $\beta_{x'x'z'}=\beta_{x'z'x'}$ are the only symmetry-allowed elements remaining in the molecular $\beta^{(2)}$ tensor. Under these conditions, the $x_{ZZZ}/x_{ZXX}$ tensor ratio should be ~−2+0i. A value of −1.81 (±0.02)−0.7i (±0.1i) was obtained using the NONE methodology of the present invention. Quantum chemical calculations for DR-19 and DPB performed in this work both indicated that the molecular tensors are dominated by the $\beta_{z'z'z'}$ element, in which the z'-axis is the long axis of the chromophore. In this case, $x_{zxx}/x_{xxz}$ tensor ratio is expected to be ~1. NONE measurepseudo-$C_{2v}$ symmetry. Since $\beta_{x'x'z'}=\beta_{x'z'x'}$ are the only remaining symmetry-allowed elements in the $\beta^{(2)}$ tensor, $\alpha_{x'z'}$ and $\alpha_{z'x'}$ are the only nonzero elements in the TPA tensor. Diagonalizing this symmetric TPA tensor yields two equal and opposite principal elements, for which R=−1. In DR-19 and DPB, the TPA tensor contains symmetry-allowed contributions along the long axis, perpendicular to the long axis within the molecular plane, and orthogonal to the molecular plane. Quantum chemical calculations of the TPA tensors yielded R values of −0.02 for both DR-19 and DPB (with the negative sign indicating a sign change between $\alpha_{x'x'}$ and $\alpha_{z'z'}$). These values indicate strong TPA polarization along the long molecular axis (i.e., the z'-axis) in each molecule, a relatively small short-axis (i.e., x'-axis) contribution, and insignificant out-of-plane contributions. The measured depolarization ratios of the TPA tensors are consistent with these predictions of the modeling calculations, in which the R value for DR-19 was observed to be 0.00 (±0.02)+0.02i (±0.01i) and the value for DPB was observed to be −0.29 (±0.02)−0.21i (±0.03i). The value for DR-19 is within experimental error of the measured depolarization ratio, indicating that the two-photon transitions are predominantly polarized along the long z'-axis (i.e., the pseudo-$C_2$ axis). The depolarization ratio does differ for DPB, however. The presence of a nonzero value for R with a significant imaginary contribution in the case of DPB may potentially be attributed to changes in the molecular tensor from aggregation at the interface.

11. SUPPORTING CALCULATIONS

Calculation of the Predicted Intensity-Dependent Response from the NONE Polarization Measurements Irrespective of the $x^{(2)}$ nonlinear optical properties of the system of interest, the complex-valued parameter ρ can be expressed using the following general equation.

$$\rho = \frac{e_p^{2\omega}}{e_s^{2\omega}} = \frac{\chi_{ppp}(e_p^\omega)^2 + \chi_{psp}(e_s^\omega)(e_p^\omega) + \chi_{pss}(e_s^\omega)^2}{\chi_{spp}(e_p^\omega)^2 + \chi_{ssp}(e_s^\omega)(e_p^\omega) + \chi_{sss}(e_s^\omega)^2} \quad (S.1)$$

In Eq. S.1, effective $x^{(2)}$ tensor elements are used, consisting of linear combinations of the true surface $x^{(2)}$ tensor elements combined with the appropriate geometric and Fresnel factor constant multipliers. The first subscript in the $x^{(2)}$ tensor elements indicates the p- or s-polarization component generated when driven by a fundamental field with polarization components given by latter two indices. The two remaining nonzero effective tensor elements $x_{pps}$ and $x_{sps}$ have been omitted, because the degeneracy present when using a single incident fundamental beam in SHG requires that the last two indices are interchangeable, such that $x_{pps}=x_{psp}$ and $x_{sps}=x_{ssp}$. In uniaxial films, the relationships between the effective $x^{(2)}$ tensor elements and the true symmetry-allowed surface $x^{(2)}$ tensor elements are relatively simple.

$$x_{ppp} = -s_3 x_{XXZ} + s_5 x_{ZXX} + s_7 x_{ZZZ} \quad (S.2a)$$

$$x_{psp} = -s_4 x_{XYZ} \quad (S.2b)$$

$$x_{pss} = s_6 x_{ZYY} = s_6 x_{ZXX} \quad (S.2c)$$

$$x_{spp} = s_2 x_{YXZ} = -s_2 x_{XYZ} \quad (S.2d)$$

$$x_{ssp} = s_1 x_{YYZ} = s_1 x_{XXZ} \quad (S.2e)$$

$$x_{sss} = 0 \quad (S.2f)$$

In Eq. S.2 the $s_n$ coefficients consist of constants related to the experimental geometry and Fresnel factors relating the incident and exigent fields to the fields within the nonlinear film.

Consistent with the experimental configuration, an s-polarized beam passing through a half wave plate rotated an angle $\alpha_H^\omega$ and a quarter wave plate rotated an angle of $\alpha_Q^\omega = -45°$ yields the following Jones vector for the incident fundamental beam.

$$e^\omega = \begin{bmatrix} e^{-2i\alpha_H^\omega} \\ ie^{2i\alpha_H^\omega} \end{bmatrix} \quad (S.3)$$

Explicit evaluation of Eq. S.1 for different rotation angles $\alpha_H^\omega$ (indicated by the subscript on ρ) using the expression in Eq. S.3 for $e^\omega$ yields the following set of four equations.

$$\rho_{-\pi/8} = \frac{\chi_{ppp} - \chi_{psp} + \chi_{pss}}{\chi_{spp} - \chi_{ssp}} \quad (S.4a)$$

$$\rho_{\pi/8} = \frac{\chi_{ppp} + \chi_{psp} + \chi_{pss}}{\chi_{spp} + \chi_{ssp}} \quad (S.4b)$$

$$\rho_0 = \frac{\chi_{ppp} + i\chi_{psp} - \chi_{pss}}{\chi_{spp} + i\chi_{ssp}} \quad (S.4c)$$

$$\rho_{\pi/4} = \frac{-\chi_{ppp} + i\chi_{psp} + \chi_{pss}}{-\chi_{spp} + i\chi_{ssp}} \quad (S.4d)$$

Taking appropriate sums and differences of the expressions for $\rho_{-\pi/8}$ and $\rho_{\pi/8}$ and the expressions for $\rho_0$ and $\rho_{\pi/4}$ yields the following set of relations.

$$x_{ssp}\Sigma_{\pi/8} - x_{ssp}\Delta_{\pi/8} = 2x_{psp} \quad (S.5a)$$

$$x_{ssp}\Sigma_0 - ix_{spp}\Delta_0 = 2x_{psp} \quad (S.5b)$$

$$x_{ssp}\Delta_{\pi/8} - x_{spp}\Sigma_{\pi/8} = 2(x_{ppp} + x_{pss}) \quad (S.5c)$$

$$ix_{ssp}\Delta_0 + x_{spp}\Sigma_0 = 2(x_{ppp} - x_{pss}) \quad (S.5d)$$

A shorthand notation has been introduced, in which $\Sigma_{\pi/8}=(\rho_{\pi/8}+\rho_{-\pi/8})$, $\Sigma_0=(\rho_0+\rho_{\pi/4})$, $\Delta_{\pi/8}=(\rho_{\pi/8}-\rho_{-\pi/8})$, and $\Delta_0=(\rho_0-\rho_{\pi/4})$. Appropriate combinations of these relations yield the following equalities.

$$\frac{\chi_{spp}}{\chi_{ssp}} = \frac{\Sigma_0 - \Sigma_{\pi/8}}{i\Delta_0 - \Delta_{\pi/8}} \quad (S.6a)$$

$$\frac{\chi_{psp}}{\chi_{ssp}} = \frac{1}{2}\left[\Sigma_{\pi/8} - \frac{\chi_{spp}}{\chi_{ssp}}\Delta_{\pi/8}\right] \quad (S.6b)$$

$$\frac{\chi_{pss}}{\chi_{ssp}} = -\frac{1}{4}\left[(\Delta_{\pi/8} + i\Delta_0) - \frac{\chi_{spp}}{\chi_{ssp}}(\Sigma_{\pi/8} - \Sigma_0)\right] \quad (S.6c)$$

$$\frac{\chi_{ppp}}{\chi_{ssp}} = -\frac{1}{4}\left[(\Delta_{\pi/8} - i\Delta_0) - \frac{\chi_{spp}}{\chi_{ssp}}(\Sigma_{\pi/8} + \Sigma_0)\right] \quad (S.6d)$$

In the limiting case of an achiral film, $\rho_{-\pi/8}=-\rho_{-\pi/8}$ and $\rho_{\pi/4}=-\rho_0$, leading to the disappearance of the chiral tensor elements $x_{spp}$ and $x_{psp}$ and a reduction of the expressions for the achiral elements $x_{ppp}$, $x_{pss}$, and $x_{ssp}$ to those derived previously for NONE analysis of achiral films. Normalized values of the five effective $x^{(2)}$ tensor elements allowed by symmetry in uniaxial films can be obtained using the relations in Equations S.6 and are summarized in Table 6. Since the ρ values are complex parameters, all phase information is retained in the effective $x^{(2)}$ tensor elements. The four nonzero independent surface tensor elements $x_{ZZZ}$, $x_{ZXX}=x_{ZYY}$, $x_{XXZ}=x_{XZX}=x_{YYZ}=x_{YZY}$, and $x_{XYZ}=x_{XZY}=-x_{YXZ}=-x_{YZX}$ can be obtained from the effective $x^{(2)}$ tensor elements using the following set of relationships.

$$x_{ppp} = -s_3 x_{XXZ} + s_5 x_{ZXX} + s_7 x_{ZZZ} \tag{S.7a}$$

$$x_{psp} = -s_4 x_{XYZ} \tag{S.7b}$$

$$x_{pss} = s_6 x_{ZYY} \tag{S.7c}$$

$$x_{spp} = s_2 x_{YXZ} \tag{S.7d}$$

$$x_{ssp} = s_1 x_{YYZ} \tag{S.7e}$$

$$x_{sss} = 0 \tag{S.7f}$$

In Eq. S.7, the $s_n$ coefficients consist of geometric constants and Fresnel factors relating the incident and exigent fields to the fields within the nonlinear film, described in detail in the following Appendix.

By using effective $x^{(2)}$ tensor elements in treating the nonlinear optical polarization, this approach is valid irrespective of the model used to treat the optics at the interface. The true surface $x^{(2)}$ tensor elements can be obtained from the effective tensor elements using the relations in Eq. S.2, provided the $s_n$ coefficients (generally complex-valued parameters themselves) are known or can be calculated using a given model for the interfacial optics. Although, the use of the effective $x^{(2)}$ tensor elements removes several simplifying degeneracies that are present when using the true surface tensor elements (e.g., $x_{XYZ} = -x_{YXZ}$, but $x_{psp} \ne -x_{spp}$), the model-independent effective tensor elements are sufficient for complete reconstruction of the intensity-dependent response as a function of incident polarization state at a single angle of incidence and do not require any a priori assumptions regarding the thin film optical constants. Once the relative values of the five effective $x^{(2)}$ tensor elements present in uniaxial systems were determined from the NONE measurements, the complete polarization state of the exigent frequency-doubled beam including all phase information was calculated using Eq. S.1. The predicted intensity surfaces shown in FIGS. 4 and 5 were subsequently calculated using Eq. 25, which was derived from multiplication of the appropriate Jones matrices for a quarter wave plate/half wave plate/polarizer combination positioned between the sample and the detector.

Because measurement of the ratio $x_{psp}/x_{spp}$ yields a complex-valued constant that depends only on the thin film optical properties of the substrate/film/superstrate system and is independent of both the molecular hyperpolarizability and molecular orientation. Because the imaginary component of the interfacial refractive index $k_3$ is allowed to be nonzero, the values of $n_3$ and $k_3$ that yield a minimum in the value of $|x_{XYZ}/x_{YXZ}+1| = |s_2(n_3,k_3)x_{psp}/s_4(n_3,k_3)x_{spp}-1|$ correspond to the optimal effective set of optical constants describing the interfacial layer with no additional adjustable parameters.

Expressions for the Fresnel Factors

Two different mathematical approaches were considered for generating the Fresnel factors necessary for relating the macroscopic measurements back to the $x^{(2)}$ surface tensor elements. The first (Model A) was derived using a mathematical formalism similar to that developed for interpreting traditional ellipsometry measurements of thin films. The second model (Model B) has been widely used for over a decade and is described in detail in previous work by Shen and coworkers, by Heinz, and by Mizrahi and Sipe.

Model A

The Fresnel factors $L^\omega$ and $L^{2\omega}$ were derived from established expressions for interpreting ellipsometric polarization changes from interactions of electromagnetic radiation with thin surface films. Considering the three-layer system described in FIG. 2, the nonlinear optically active thin interfacial layer is indicated at 64. The driving fundamental fields within the layer are generated by summing together all the refracted and reflected contributions within medium 64. For the X-polarized component of the field, the local electric field within the nonlinear layer is given by the following infinite series.

$$e_x^\omega = \hat{e}_x^\omega [t_{p13}^\omega - t_{p13}^\omega r_{p32}^\omega e^{-i\beta^\omega} + t_{p13}^\omega r_{p32}^\omega r_{p31}^\omega e^{-i2\beta} - t_{p13}^\omega r_{p32}^\omega r_{p31}^\omega r_{p32}^\omega e^{-i2\beta} + \ldots] \tag{S.8}$$

The negative sign on the upward propagating components (i.e., towards medium 1) accounts for the change in the coordinate system describing beam propagation upon reflection. The phase thickness $\beta$ is given by:

$$\beta = 2\pi(d/\lambda)n_3 \cos\theta_3 \tag{S.9}$$

Collection of terms in Eq. S.8 together with the relation $1+x+x^2+x^3+\ldots = 1/(1-x)$ for $|x|<1$ leads to the following expression for the X-polarized field within the interfacial layer.

$$e_X^\omega = \hat{e}_X^\omega \frac{t_{p13}^\omega}{1 - r_{p32}^\omega r_{p31}^\omega e^{-i2\beta^\omega}} \left(1 - r_{p32}^\omega e^{-i\beta^\omega}\right) \tag{S.10}$$

Similar approaches can be used to evaluate the Y- and Z-polarized field components within the thin film as they relate to the incident fields to produce the set of Fresnel factors given in Eq. 31.

The nonlinear optical field components detected in the far-field can be calculated using the same basic approach.

$$e_X^{2\omega} = P_X^{2\omega} \left\{ \begin{array}{l} t_{p31}^{2\omega}\left[1 + r_{p31}^{2\omega}r_{p32}^{2\omega}e^{-i2\beta^{2\omega}} + \left(r_{p31}^{2\omega}r_{p32}^{2\omega}e^{-i2\beta^{2\omega}}\right)^2 + \ldots\right] \\ -r_{p32}^{2\omega}t_{p31}^{2\omega}e^{-i\beta^{2\omega}}\left[1 + r_{p31}^{2\omega}r_{p32}^{2\omega}e^{-i2\beta^{2\omega}} + \right. \\ \left. \left(r_{p31}^{2\omega}r_{p32}^{2\omega}e^{-i2\beta^{2\omega}}\right)^2 + \ldots\right] \end{array} \right\} \tag{S.11}$$

In Eq. S.11, $P_X^{2\omega}$ is the X-polarized component of the nonlinear polarization generated within the interfacial layer. The expressions for the nonlinear Fresnel factors for all three polarization components are given in Eq. 32. These same equations hold in total internal reflection, in which the reflection and transmission angles and coefficients are allowed to have complex values.

Combining the linear and nonlinear Fresnel factors with the appropriate geometric terms describing the projection of the electric field components onto the Cartesian coordinates after refraction into and out of the interfacial layer leads to the following definitions for the $s_n$ coefficients in SHG of chiral films using Model A (indicated by a superscript).

$$s_1^A = 2L_{YY}^{2\omega,A} L_{YY}^{\omega,A} L_{ZZ}^{\omega,A} \sin(\theta_3^\omega) \tag{S.12a}$$

$$s_2^A = L_{YY}^{2\omega,A} L_{XX}^{\omega,A} L_{ZZ}^{\omega,A} \sin(2\theta_3^\omega) \tag{S.12b}$$

$$s_3^A = L_{XX}^{2\omega,A} L_{XX}^{\omega,A} L_{ZZ}^{\omega,A} \sin(2\theta_3^\omega) \cos(\theta_1^{2\omega}) \tag{S.12c}$$

$$s_4^A = 2L_{XX}^{2\omega,A} L_{YY}^{\omega,A} L_{ZZ}^{\omega,A} \sin(\theta_3^\omega) \cos(\theta_1^{2\omega}) \tag{S.12d}$$

$$s_5^A = L_{ZZ}^{2\omega,A} (L_{XX}^{\omega,A})^2 \cos(\theta_3^\omega) \sin(\theta_1^{2\omega}) \tag{S.12e}$$

$$s_6^A = L_{ZZ}^{2\omega,A}(L_{YY}^{\omega,A})^2 \sin(\theta_1^{2\omega}) \quad \text{(S.12f)}$$

$$s_7^A = L_{ZZ}^{2\omega,A}(L_{ZZ}^{\omega,A})^2 \sin^2(\theta_3^{\omega}) \sin(\theta_1^{2\omega}) \quad \text{(S.12g)}$$

Model B

Arguably, the most common treatments of the interfacial optics in SHG and SFG are based on two models developed independently by Mizrahi and Sipe and by Shen and coworkers. The mathematical approach described below is expressed within the framework developed by Shen and coworkers, although it can be shown to be equivalent to the Mizrahi and Sipe model in the limit of an ultrathin film.

$$L_{XX}^{\omega} = 1 - r_{p12}^{\omega} \quad \text{(S.13a)}$$

$$L_{YY}^{\omega} = 1 + r_{s12}^{\omega} \quad \text{(S.13b)}$$

$$L_{ZZ}^{\omega} = (1 + r_{p12}^{\omega})(n_1^{\omega}/n_3^{\omega})^2 \quad \text{(S.13c)}$$

In reflection, the corresponding nonlinear Fresnel factors are given by expressions virtually identical to those in Eq. S.13, but evaluated using the optical constants for the frequency doubled light.

$$L_{XX}^{2\omega} = 1 - r_{p12}^{2\omega} \quad \text{(S.14a)}$$

$$L_{YY}^{2\omega} = 1 + r_{s12}^{2\omega} \quad \text{(S.14b)}$$

$$L_{ZZ}^{2\omega} = (1 + r_{p12}^{2\omega})(n_1^{2\omega}/n_3^{2\omega})^2 \quad \text{(S.14c)}$$

In model B, the combined $s_n$ coefficients including the geometric projection terms are given by expressions similar to those in S.12 with one important exception. All angles in Model B are referenced exclusively with respect to the incident medium $\theta_1$.

$$s_1^B = 2L_{YY}^{2\omega,B} L_{YY}^{\omega,B} L_{ZZ}^{\omega,B} \sin(\theta_1^{\omega}) \quad \text{(S.15a)}$$

$$s_2^B = L_{YY}^{2\omega,B} L_{XX}^{\omega,B} L_{ZZ}^{\omega,B} \sin(2\theta_1^{\omega}) \quad \text{(S.15b)}$$

$$s_3^B = L_{XX}^{2\omega,B} L_{XX}^{\omega,B} L_{ZZ}^{\omega,B} \sin(2\theta_1^{\omega}) \cos(\theta_1^{2\omega}) \quad \text{(S.15c)}$$

$$s_4^B = 2L_{XX}^{2\omega,B} L_{YY}^{\omega,B} L_{ZZ}^{\omega,B} \sin(\theta_1^{\omega}) \cos(\theta_1^{2\omega}) \quad \text{(S.15d)}$$

$$s_5^B = L_{ZZ}^{2\omega,B}(L_{XX}^{\omega,B})^2 \cos^2(\theta_1^{\omega}) \sin(\theta_1^{2\omega}) \quad \text{(S.15e)}$$

$$s_6^B = L_{ZZ}^{2\omega,B}(L_{YY}^{\omega,B})^2 \sin(\theta_1^{2\omega}) \quad \text{(S.15f)}$$

$$s_7^B = L_{ZZ}^{2\omega,B}(L_{ZZ}^{\omega,B})^2 \sin^2(\theta_1^{\omega}) \sin(\theta_1^{2\omega}) \quad \text{(S.15g)}$$

Although not immediately obvious by inspection, the products of the linear Fresnel factors $L^{\omega}$ and the corresponding linear trigonometric terms in Models A and B are identical in the limit of a negligibly thin film (i.e. for $\beta \ll \lambda_0$, both models A and B produce identical results for the linear field amplitudes within the interfacial layer).

$$L_{XX}^{\omega,A} \cos\theta_3^{\omega} \cong L_{XX}^{\omega,B} \cos\theta_1^{\omega} \quad \text{(S.16a)}$$

$$L_{YY}^{\omega,A} \cong L_{YY}^{\omega,B} \quad \text{(S.16b)}$$

$$L_{ZZ}^{\omega,A} \sin\theta_3^{\omega} \cong L_{ZZ}^{\omega,B} \sin\theta_1^{\omega} \quad \text{(S.16c)}$$

However, this same correspondence does not occur for the nonlinear Fresnel factors in Models A and B. The analogous relationships between the Fresnel factors for the two different models at the exigent frequency are given by the following expressions in the limit of $\beta \ll \lambda_0$.

$$L_{XX}^{2\omega,A} \cos\theta_3^{2\omega} \cong L_{XX}^{2\omega,B} \cos\theta_1^{2\omega} \left[\frac{n_3^{2\omega} \cos\theta_3^{2\omega}}{n_1^{2\omega} \cos\theta_1^{2\omega}}\right] \quad \text{(S.17a)}$$

$$L_{YY}^{2\omega,A} \cong L_{YY}^{2\omega,B} \left[\frac{n_3^{2\omega} \cos\theta_3^{2\omega}}{n_1^{2\omega} \cos\theta_1^{2\omega}}\right] \quad \text{(S.17b)}$$

$$L_{ZZ}^{2\omega,A} \sin\theta_3^{2\omega} \cong L_{ZZ}^{2\omega,B} \sin\theta_1^{2\omega} \left[\frac{n_3^{2\omega} \cos\theta_3^{2\omega}}{n_1^{2\omega} \cos\theta_1^{2\omega}}\right] \quad \text{(S.17c)}$$

In the thin film limit, the nonlinear optical Fresnel factors derived in the present application (Model A) differ from those used previously (Model B) in two principal respects. First, the additional constant multiplier in brackets in all three expressions corrects for the change in field amplitude resulting from changes in the speed of light (given by the ratio of the refractive indices) and the beam area (given by the cosine terms) upon refraction out of the interfacial layer. Although this additional factor may potentially affect interpretation of absolute phase measurements of the exigent beam, it disappears in ratiometric comparisons when evaluating relative values of the $\chi^{(2)}$ tensor elements such as described in the present study. The second difference between the Fresnel factors used in Models A and B in the thin film limit is in the selection of the medium in which $\theta^{2\omega}$ is expressed in calculating the $s_n$ coefficients. Although $\theta_3^{2\omega}$ appears in the relations for Model A connecting the two sets of Fresnel factors (Eq. S.17), $\theta_1^{2\omega}$ is used when calculating the $s_n^A$ coefficients (Equations S.12). Consequently, converting between the $s_n$ coefficients used in the two models requires multiplication by the correction factor given in brackets in Eq. S.17 and an additional factor of $\sin\theta_1^{2\omega}/\sin\theta_3^{2\omega}$ for $L_{ZZ}^{2\omega}$ and $\cos\theta_1^{2\omega}/\cos\theta_3^{2\omega}$ for $L_{XX}^{2\omega}$.

$$s_1^A \cong s_1^B(n_3^{2\omega} \cos\theta_3^{2\omega}/n_1^{2\omega} \cos\theta_1^{2\omega}) \quad \text{(S.18a)}$$

$$s_2^A \cong s_2^B(n_3^{2\omega} \cos\theta_3^{2\omega}/n_1^{2\omega} \cos\theta_1^{2\omega}) \quad \text{(S.18b)}$$

$$s_3^A \cong s_3^B(n_3^{2\omega} \cos\theta_3^{2\omega}/n_1^{2\omega} \cos\theta_1^{2\omega})(\cos\theta_1^{2\omega}/\cos\theta_3^{2\omega}) = s_3^B(n_3^{2\omega}/n_1^{2\omega}) \quad \text{(S.18c)}$$

$$s_4^A \cong s_4^B(n_3^{2\omega}/n_1^{2\omega}) \quad \text{(S.18d)}$$

$$s_5^A \cong s_5^B(n_3^{2\omega} \cos\theta_3^{2\omega}/n_1^{2\omega} \cos\theta_1^{2\omega})(\sin\theta_1^{2\omega}/\sin\theta_3^{2\omega})$$
$$= s_5^B[(n_3^{2\omega})^2 \cos\theta_3^{2\omega}/(n_1^{2\omega})^2 \cos\theta_1^{2\omega}] \quad \text{(S.18e)}$$

$$s_6^A \cong s_6^B[(n_3^{2\omega})^2 \cos\theta_3^{2\omega}/(n_1^{2\omega})^2 \cos\theta_1^{2\omega}] \quad \text{(S.18f)}$$

$$s_7^A \cong s_7^B[(n_3^{2\omega})^2 \cos\theta_3^{2\omega}/(n_1^{2\omega})^2 \cos\theta_1^{2\omega}] \quad \text{(S.18g)}$$

The different trends shown in FIG. 10 can be understood by explicit substitution for the ratio $s_4/s_2$ in the two models. In Model B, only the Z-components of the incident and exigent electric fields are influenced by the optical properties of the interfacial layer. Consequently, the cancellation of the $L_{ZZ}^{\omega}$ term in the ratio of $\chi_{2,psp}/s_4\chi_{spp}$ yields a parameter that is completely independent of the interfacial thin film optical constants and can be calculated from the measured effective tensor elements with no adjustable parameters.

$$\frac{\chi_{XYZ}}{\chi_{YXZ}} = -\frac{s_2^B \chi_{psp}}{s_4^B \chi_{spp}} = -\frac{L_{YY}^{B,2\omega} L_{XX}^{B,\omega}}{L_{XX}^{B,2\omega} L_{YY}^{B,\omega}}. \quad \text{(S.19)}$$

-continued $$\frac{\chi_{psp}}{\chi_{spp}} = -\frac{(1+r_{s/2}^{2\omega})(1-r_{p/2}^{\omega})}{(1-r_{p/2}^{2\omega})(1+r_{s/2}^{\omega})} \cdot \frac{\chi_{psp}}{\chi_{spp}}$$

The known refractive indices of water and fused silica and the experimentally measured values of $x_{psp}$ and $x_{spp}$ yield a measured ratio of $x_{XYZ}/x_{YXZ}$ equal to 0.024–1.61i when using Model B for all assumed values of the interfacial optical constants, as shown in FIG. 10. Consequently, for Model B there is no combination of the interfacial optical constants that recovers the required symmetry relationship $x_{XYZ}/x_{YXZ} = -1+0i$. By comparison, the ratio of $s_2 x_{psp}/s_4 x_{spp}$ calculated using Model A retains a dependence on the thin film optical constants at the doubled frequency through the ratio of cosine functions.

$$\frac{\chi_{XYZ}}{\chi_{YXZ}} = -\frac{s_2^A \chi_{psp}}{s_4^A \chi_{spp}} = -\frac{(1+r_{s/2}^{2\omega})(1-r_{p/2}^{\omega})\cos\theta_3^{2\omega}}{(1-r_{p/2}^{2\omega})(1+r_{s/2}^{\omega})\cos\theta_1^{2\omega}} \frac{\chi_{psp}}{\chi_{spp}} \quad (S.20)$$

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method for measuring a property associated with a sample comprising the steps of:
projecting an incident polarized light beam having at least one polarization state through a total internal reflection cell containing said sample to generate an exigent light beam having a complex polarization;
projecting said exigent light beam through an exigent light beam path comprising a quarter wave plate having a quarter wave plate rotation angle and half wave plate having a half wave plate rotation angle, and a first detector operable to produce a detected signal intensity;
iteratively adjusting said quarter wave plate rotation angle and said half wave plate rotation angle to produce a minimum detected signal intensity at said first detector for at least one of said selectable polarization states;
determining ellipsometric nulling angles from said quarter wave plate rotation angle and said half wave plate rotation angle at said minimum detected signal intensity; and
using said ellipsometric nulling angles to provide an indication of said complex polarization of said exigent light beam;
wherein said complex polarization of said exigent light beam provides an indication of said property associated with said sample.

2. The method of claim 1, wherein said minimum detected signal intensity comprises substantially zero intensity.

3. The method of claim 1 further comprising the step of: using said ellipsometric nulling angles to determine a complex-valued tensor ratio of said sample.

4. The method of claim 3, wherein said complex-valued tensor ratio provides an indication of a biological property of said sample.

5. The method of claim 3, wherein said sample comprises an unlabeled protein, and wherein said complex-valued tensor ratio measures a specific binding interaction of said unlabeled protein with a labeled receptor protein.

6. The method of claim 5, wherein said specific binding interaction comprises a binding-induced change in an orientation of said labeled receptor protein.

7. The method of claim 6, wherein said labeled receptor protein is a second harmonic generation-labeled receptor protein.

8. The method of claim 6, wherein said labeled receptor protein is a sum-frequency generation-labeled receptor protein.

9. The method of claim 1, wherein said at least one polarization state comprises a first polarization state that is at least approximately linear polarized and a second polarization state that is at least approximately circularly polarized.

10. The method of claim 1, wherein said at least one polarization state comprises:
a first polarization state that is at least approximately linearly polarized light oriented at −45°;
a second polarization state that is at least approximately right circularly polarized light;
a third polarization state that is at least approximately linearly polarized light oriented at +45°; and
a fourth polarization state that is at least approximately left circularly polarized light.

11. The method of claim 1, wherein said complex polarization of said exigent light provides an indication of a surface concentration of an adsorbate.

12. The method of claim 1, wherein said complex polarization of said exigent light provides an indication of a charge reorganization during an adsorption process.

13. The method of claim 1 further comprising the steps of:
projecting said exigent light beam through a beam splitter to provide a p-polarized beam and a s-polarized beam, wherein said s-polarized beam projects on said first detector and wherein said p-polarized beam projects upon a second detector;
iteratively adjusting said quarter wave plate rotation angle and said half wave plate rotation angle to produce a minimum intensity at said first detector and a maximum intensity at said second detector.

14. The method of claim 13, wherein said indication of said complex polarization provides at least an approximate full complex-valued $x^{(2)}$ tensor element ratio.

15. The method of claim 1, wherein said sample comprises an analyte of interest, said method further comprising the steps of:
using said indication of said complex polarization to calculate a depolarization ratio of a two-photon absorption (TPA) tensor for said analyte of interest.

16. The method of claim 15, wherein said depolarization ratio provides an indication of the absorption kinetics of a film interface.

17. The method of claim 16, wherein at least a portion of said film interface comprises a biological material.

18. The method of claim 15, wherein said property provides a background-free indication of said sample's protein/surface interaction.

19. The method of claim 18, wherein said background-free indication is approximately in real time.

20. The method of claim 15, wherein said property is an indication of said sample's adsorption kinetics at a film interface.

21. A method for determining a property associated with a sample of interest comprising the steps of:

passing a polarized light beam through a nonlinear optical null ellipsometry device comprising a detector and a sample chamber to produce a polarization state measurement response at said detector;

depositing a first sample species into said sample chamber;

adjusting said nonlinear optical null ellipsometry device to null said polarization state measurement response at said detector;

depositing a second sample species into said sample chamber; and measuring a change in said polarization state measurement response at said detector;

wherein said change in said polarization states provides an indication of a property of said second sample species.

22. The method of claim 21, wherein said change in said polarization state measurement provides an indication of a number density of said second sample species.

23. A method for measuring a property of a sample comprising the steps of:
providing a nonlinear optical null ellipsometry measurement device comprising an incident light source having at least "n" selectable incident polarization states, a sample chamber and an exigent beam path comprising at least one optical device providing a selectable rotation angle, and a detector;
placing a sample in the sample chamber to form a film in said sample chamber;
projecting an incident beam from said incident light source through said sample chamber to produce an exigent light beam comprising at least one harmonic response to said incident light source wherein said exigent light beam produces a detector response at said detector;
iteratively determining at least one said selectable rotation angle that minimizes said detector response for each of at least "m" said selectable incident polarization states, wherein "n" is greater than or equal to "m"; and
using the "m" selectable rotation angles that minimize said detector response to determine an indication of the ratio of $e_p^{2\omega}/e_s^{2\omega}$.

24. The method of claim 23, wherein said detector response comprises approximately a secondary harmonic response.

25. The method of claim 24, wherein said exigent light beam includes a wavelength near resonant with said sample's chromophore.

26. The method of claim 24, wherein said response at said detector is monitored over a period of time comprising at least some period before introduction of said sample into said test chamber.

27. The method of claim 24, wherein said sample comprises an analyte of interest and at least one other substance.

28. The method of claim 24, further comprising the step of:
normalizing said response at said detector to provide normalized intensity ratios; and
using said normalized intensity ratios to determine a property of interest of said sample.

29. The method of claim 28, wherein said property of interest is related to molecular orientation of said sample.

30. The method of claim 23, wherein said exigent light beam has a wavelength that is approximately resonant with a chromophore property of said sample; the method further comprising using said wavelength to determine a property of said sample related to said chromophore property of said sample.

31. A method for characterizing the surface of a sample comprising the steps:
providing an incident light beam having "m" selectable polarization states;
projecting said incident light beam into a total internal reflection cell containing a sample, wherein said total internal reflection cell and said sample form an interfacial system, and wherein said incident light beam interacts with said interfacial system to produce an exigent light beam having at least one component;
passing said exigent light beam through an exigent light beam path comprising at least one optical device having at least one adjustable rotation angle and a first detector, wherein at least a first component of said exigent light beam passes through said exigent light beam path to fall upon said first detector and wherein said first detector produces a first detected signal intensity response;
determining a first one of said adjustable rotation angles for at least one of the "m" selectable polarization states of said incident light beam that produces a minimum of said first detected signal intensity at said first detector; and
determining at least one characteristic of said sample using said first one of said adjustable rotation angles.

32. The method of claim 31, wherein said exigent light beam path further includes a beam splitter and a second detector, the method comprising the further step of:
passing said exigent light beam through said beam splitter to produce said first component of said exigent light beam and a second component of said exigent light beam, wherein said second component of said exigent light beam falls upon said second detector.

33. The method of claim 31, wherein said at least one optical device comprises a quarter wave plate having a quarter wave plate rotation angle and half wave plate having a half wave plate rotation angle; wherein said quarter wave plate rotation angle and said half wave plate rotation angle are adjustable to minimize said first detected signal intensity.

34. The method of claim 33, wherein said at least one optical device includes a polarizer having a polarizer rotation angle.

35. The method of claim 33, wherein said polarizer rotation angle is rotated approximately about 90°.

* * * * *

UNITED STATES PATENT AND TRADEMARK OFFICE
CERTIFICATE OF CORRECTION

PATENT NO. : 7,336,359 B1
APPLICATION NO. : 11/120350
DATED : February 26, 2008
INVENTOR(S) : Garth J. Simpson It is certified that error appears in the above-identified patent and that said Letters Patent is hereby corrected as shown below:

In column 14, beginning at line 38, please change

"

TABLE 2

Values of the $\chi^{(2)}$ tensor elements for R-6G in 2-propanol, normalized for $\chi_{xxx} = 1$

| | | PDI | | | |
|---|---|---|---|---|---|
| | NONE | (+) | (−) | (+) | (−) |
| $\chi_{xxx}$ | 1 | | 1 | | 1 |
| $\chi_{zxx}$ | −0.5 (±0.2) − 0.52i (±0.09i) | 0.90 (±0.02) | | −0.90 (±0.02) | |
| $\chi_{xzx}$ | 1.7 (±0.1) + 0.7i (±0.1i) | 1.54 (±0.08) | −1.78 (±0.08) | 1.50 (±0.08) | −1.83 (±0.08) |
| $\chi_{zzz}/\chi_{zxx}$ | −2.3 (±0.3) + 1.2i (±0.4i) | 1.7 (±0.1) | −2.0 (±0.1) | −1.7 (±0.1) | 2.0 (±0.1) |

The tensor components determined from the intensity-based measurements were evaluated assuming purely real $\chi^{(2)}$ elements and yielded four possible solutions consistent with the set of experimental results.

TABLE 3

Values of the $\chi^{(2)}$ tensor elements for DR-19 in 2-propanol, normalized for $\chi_{xxx} = 1$

| | | PDI | | | |
|---|---|---|---|---|---|
| | NONE | (+) | (−) | (+) | (−) |
| $\chi_{xxx}$ | 1 | | 1 | | 1 |
| $\chi_{zxx}$ | 0.9 (±0.1) − 0.14i (±0.09i) | 0.97 (±0.04) | | −0.97 (±0.04) | |
| $\chi_{zzz}$ | 2.5 (±0.3) + 1.0i (±0.2i) | 2.5 (±0.1) | −2.6 (±0.1) | 2.5 (±0.1) | −2.1 (±0.1) |

"

UNITED STATES PATENT AND TRADEMARK OFFICE
CERTIFICATE OF CORRECTION

PATENT NO. : 7,336,359 B1
APPLICATION NO. : 11/120350
DATED : February 26, 2008
INVENTOR(S) : Garth J. Simpson It is certified that error appears in the above-identified patent and that said Letters Patent is hereby corrected as shown below:

To:

Table 2
Values of the $\chi^{(2)}$ tensor elements for R-6G in 2-propanol, normalized for $\chi_{xxz}=1$ --
| | NONE | PDI | | | |
|---|---|---|---|---|---|
| | | (+) | (-) | (+) | (-) |
| $\chi_{xxz}$ | 1 | 1 | | 1 | |
| $\chi_{zxx}$ | -0.5 (±0.2) - 0.52$i$ (±0.09$i$) | 0.90 (±0.02) | | -0.90 (±0.02) | |
| $\chi_{zzz}$ | 1.7 (±0.1) + 0.7$i$ (±0.1$i$) | 1.54 (± 0.08) | -1.78 (±0.08) | 1.50 (±0.08) | -1.83 (±0.08) |
| $\chi_{zzz}/\chi_{zxx}$ | -2.3 (±0.3) + 1.2$i$ (±0.4$i$) | 1.7 (±0.1) | -2.0 (±0.1) | -1.7 (±0.1) | 2.0 (±0.1) |
--

The tensor components determined from the intensity-based measurements were evaluated assuming purely real $\chi^{(2)}$ elements and yielded four possible solutions consistent with the set of experimental results.

Table 3
Values of the $\chi^{(2)}$ tensor elements for DR-19 in 2-propanol, normalized for $X_{xxz}=1$

| | NONE | PDI | | | |
|---|---|---|---|---|---|
| | | (+) | (-) | (+) | (-) |
| $\chi_{xxz}$ | 1 | 1 | | 1 | |
| $\chi_{zxx}$ | 0.9 (±0.1) - 0.14$i$ (±0.09$i$) | 0.97 (±0.04) | | -0.97 (±0.04) | |
| $\chi_{zzz}$ | 2.5 (±0.3) + 1.0$i$ (±0.2$i$) | 2.5 (±0.1) | -2.6 (±0.1) | 2.5 (±0.1) | -2.1 (±0.1) |

In column 15, lines 29-42, please change

TABLE 4

" 
| Comparison of the experimental intensity ratios and those predicted from the NONE data | | |
|---|---|---|
| | Observed | Predicted from NONE |
| Disperse red 19 | | |
| $I_{ps}/I_{s45}$ | 0.88 (±0.08) | 0.8 (±0.2) |
| $I_{pp}/I_{s45}$ | 7.2 (±0.5) | 8 (±1) |
| Rhodamine 6G | | |
| $I_{ps}/I_{s45}$ | 0.76 (±0.03) | 0.5 (±0.2) |
| $I_{pp}/I_{s45}$ | 2.8 (±0.3) | 4.1 (±0.6) |
"

UNITED STATES PATENT AND TRADEMARK OFFICE
CERTIFICATE OF CORRECTION

PATENT NO. : 7,336,359 B1
APPLICATION NO. : 11/120350
DATED : February 26, 2008
INVENTOR(S) : Garth J. Simpson Page 3 of 12

It is certified that error appears in the above-identified patent and that said Letters Patent is hereby corrected as shown below:

To

Table 4
Comparison of the experimental intensity ratios and those predicted from the NONE data

|  | Observed | Predicted from NONE |
|---|---|---|
| Disperse red 19 | | |
| $I_{ps}/I_{s45}$ | 0.88 (±0.08) | 0.8 (±0.2) |
| $I_{pp}/I_{s45}$ | 7.2 (±0.5) | 8 (±1) |
| Rhodamine 6G | | |
| $I_{ps}/I_{s45}$ | 0.76 (±0.03) | 0.5 (±0.2) |
| $I_{pp}/I_{s45}$ | 2.8 (±0.3) | 4.1 (±0.6) |

In column 31, lines 34-45, please change

"
TABLE 10
Comparison of Measured and Predicted Interfacial Optical Constants for FITC-BSA.

| Optical Constants | Measured by NONE | Predicted from Model A[a] | Predicted from Model B[b] |
|---|---|---|---|
| $n_3^{2\omega}$ | 1.387 (±0.005) | 1.3982 | 1.365 to 1.655 |
| $k_3^{2\omega}$ | 0.0000i (±0.0009i) | 0 | 0.0004i to 0.002i |

[a] From Eq. 40.
[b] From prior art combined with Kramers-Kronig transformation of the visible absorbance spectrum.
"

To

TABLE 10
Comparison of Measured and Predicted Interfacial Optical Constants for FITC-BSA.

| Optical Constants | Measured by NONE | Predicted from Model A[a] | Predicted from Model B[b] |
|---|---|---|---|
| $n_3^{2\omega}$ | 1.387 (± 0.005) | 1.3982 | 1.365 to 1.655 |
| $k_3^{2\omega}$ | 0.0000i (± 0.0009i) | 0 | 0.0004i to 0.002i | a. From Eq. 40.
b. From prior art combined with Kramers-Kronig transformation of the visible absorbance

UNITED STATES PATENT AND TRADEMARK OFFICE
CERTIFICATE OF CORRECTION

PATENT NO. : 7,336,359 B1
APPLICATION NO. : 11/120350
DATED : February 26, 2008
INVENTOR(S) : Garth J. Simpson It is certified that error appears in the above-identified patent and that said Letters Patent is hereby corrected as shown below:

Beginning at column 31, line 57 ending at column 32, line 20, please change

"

TABLE 11
Surface Tensor Elements Evaluated Using the Measured Effective Interfacial Optical Constants for FITC-BSA

| $\chi_{ssp}$ $\chi_{pss}$ | $\chi_{psp}$ | $\chi_{spp}$ | $\chi_{ppp}$ |
|---|---|---|---|
| 1 | −0.01 (±0.02) +0.31i (±0.01i) | −0.30 (±0.01) −0.10i (±0.01i) | −0.05 (±0.01) −0.173i (±0.002i) | 0.935 (±0.009) +0.66i (±0.01i) |

| $\chi_{xxz}$ $\chi_{zxx}$ | $\chi_{xyz}$ | $\chi_{yxz}$ | $\chi_{zzz}$ |
|---|---|---|---|
| 1 | −0.01 (±0.04) +0.66i (±0.02i) | 0.56 (±0.01) +0.12i (±0.03i) | −0.566 (±0.009) −0.12i (±0.04i) | 2.16 (±0.03) +0.73i (±0.04i) |

|  | Predicted[a] | Measured |
|---|---|---|
| $D = \dfrac{\chi_{zzz} + 2\chi_{zxx} - 2\chi_{xxz}}{\chi_{zzz} + 4\chi_{zxx} - 2\chi_{xxz}}$ | 0.6 + 0i | 0.61 (±0.05) −0.02i (±0.03i) |
| $\dfrac{\chi_{zxx} + 2\chi_{xxz}}{\chi_{zzz}}$ | 1 + 0i | 0.84 (±0.01) +0.08i (±0.06i) |

[a] Valid in the limit of weak orientational order.

"

UNITED STATES PATENT AND TRADEMARK OFFICE
CERTIFICATE OF CORRECTION

PATENT NO. : 7,336,359 B1
APPLICATION NO. : 11/120350
DATED : February 26, 2008
INVENTOR(S) : Garth J. Simpson It is certified that error appears in the above-identified patent and that said Letters Patent is hereby corrected as shown below:

To

TABLE 11

Surface Tensor Elements Evaluated Using the Measured Effective Interfacial Optical Constants for FITC-BSA

| $\chi_{ssp}$ $\chi_{pss}$ | $\chi_{psp}$ | $\chi_{spp}$ | $\chi_{ppp}$ |
|---|---|---|---|
| 1 | −0.01 (±0.02) +0.31i (±0.01i) | −0.30 (±0.01) −0.10i (±0.01i) | −0.05 (±0.01) −0.173i (±0.002i) | 0.935 (±0.009) +0.66i (±0.01i) |

| $\chi_{xxz}$ $\chi_{zxx}$ | $\chi_{xyz}$ | $\chi_{yxz}$ | $\chi_{zzz}$ |
|---|---|---|---|
| 1 | −0.01 (±0.04) +0.66i (±0.02i) | 0.56 (±0.01) +0.12i (±0.03i) | −0.566 (±0.009) −0.12i (±0.04i) | 2.16 (±0.03) +0.73i (±0.04i) |

| | Predicted* | Measured |
|---|---|---|
| $D = \dfrac{\chi_{zzz} + 2\chi_{zxx} - 2\chi_{xxz}}{\chi_{zzz} + 4\chi_{zxx} - 2\chi_{xxz}}$ | 0.6 + 0i | 0.61 (±0.05) −0.02i (±0.03i) |
| $\dfrac{\chi_{zxx} + 2\chi_{xxz}}{\chi_{zzz}}$ | 1 + 0i | 0.84 (±0.01) +0.08i (±0.06i) |

*Valid in the limit of weak orientational order.

UNITED STATES PATENT AND TRADEMARK OFFICE
CERTIFICATE OF CORRECTION

PATENT NO. : 7,336,359 B1
APPLICATION NO. : 11/120350
DATED : February 26, 2008
INVENTOR(S) : Garth J. Simpson It is certified that error appears in the above-identified patent and that said Letters Patent is hereby corrected as shown below:

In column 37, lines 10-13, please change

" $I_{det}^{2\omega} \propto |e_p^{2\omega}|^2 \cos^2(\alpha_{pol}^{2\omega}) + |e_s^{2\omega}|^2 \sin^2(\alpha_{pol}^{2\omega}) + 2[Re(e_p^{2\omega})Re(e_s^{2\omega}) + Im(e_p^{2\omega})Im(e_s^{2\omega})] \sin(\alpha_{pol}^{2\omega}) \cos(\alpha_{pol}^{2\omega})$ " (55)

To

-- $I_{det}^{2\omega} \propto |e_p^{2\omega}|^2 \cos^2(\alpha_{pol}^{2\omega}) + |e_s^{2\omega}|^2 \sin^2(\alpha_{pol}^{2\omega}) + 2[Re(e_p^{2\omega})Re(e_s^{2\omega}) + Im(e_p^{2\omega})Im(e_s^{2\omega})] \sin(\alpha_{pol}^{2\omega}) \cos(\alpha_{pol}^{2\omega})$ (55) --

In column 37, lines 35-44, please change

" $|\rho|^2 = \left(\frac{C+A}{C-A}\right)$ (57a)

$Re(\rho) = \frac{B}{C-A}$ (57b)

$\rho = Re(\rho) + iIm(\rho) = \frac{B \pm i\sqrt{C^2 - A^2 - B^2}}{C-A}$ (57c) "

To

-- $|\rho|^2 = \left(\frac{C+A}{C-A}\right)$ (57a)

$Re(\rho) = \frac{B}{C-A}$ (57b)

$\rho = Re(\rho) + iIm(\rho) = \frac{B \pm i\sqrt{C^2 - A^2 - B^2}}{C-A}$ (57c) --

In column 37, lines 50-59, please change $|\rho|^2 = \left(\frac{C-A}{C+A}\right)$ (58a)

$Re(\rho) = \frac{-B}{C+A}$ (58b)

" $\rho = Re(\rho) + iIm(\rho) = \frac{B \pm i\sqrt{C^2 - A^2 - B^2}}{C+A}$ (58c) "

Page 6 of 12

UNITED STATES PATENT AND TRADEMARK OFFICE
CERTIFICATE OF CORRECTION

PATENT NO. : 7,336,359 B1
APPLICATION NO. : 11/120350
DATED : February 26, 2008
INVENTOR(S) : Garth J. Simpson It is certified that error appears in the above-identified patent and that said Letters Patent is hereby corrected as shown below:

To $$|\rho|^2 = \left(\frac{C-A}{C+A}\right) \quad (58a)$$

-- $$\text{Re}(\rho) = \frac{-B}{C+A} \quad (58b)$$ --

$$\rho = \text{Re}(\rho) + i\text{Im}(\rho) = \frac{B \pm i\sqrt{C^2 - A^2 - B^2}}{C+A} \quad (58c)$$

In column 38, lines 34-43, please change

"
$$I_{det}^{2\omega} \propto K \sin(2\alpha_Q^{2\omega}) + L \sin(4\alpha_Q^{2\omega}) + M \cos(4\alpha_Q^{2\omega}) + N \quad (61a)$$

$$K = 2Im[(e_p^{2\omega})(e_s^{2\omega})^*] \quad (61b)$$

$$L = Re[(e_p^{2\omega})(e_s^{2\omega})^*] \quad (61c)$$

$$M = \tfrac{1}{2}[|e_p^{2\omega}|^2 - |e_s^{2\omega}|^2] \quad (61d)$$

$$N = \tfrac{1}{2}[3|e_p^{2\omega}|^2 + |e_s^{2\omega}|^2] \quad (61e)$$
"

To

-- $$I_{det}^{2\omega} \propto K \sin\left(2\alpha_Q^{2\omega}\right) + L \sin\left(4\alpha_Q^{2\omega}\right) + M \cos\left(4\alpha_Q^{2\omega}\right) + N \quad (61a)$$ --

$$K = 2\,\text{Im}\left[\left(e_p^{2\omega}\right)\left(e_s^{2\omega}\right)^*\right] \quad (61b)$$

$$L = \text{Re}\left[\left(e_p^{2\omega}\right)\left(e_s^{2\omega}\right)^*\right] \quad (61c)$$

$$M = \tfrac{1}{2}\left[\left|e_p^{2\omega}\right|^2 - \left|e_s^{2\omega}\right|^2\right] \quad (61d)$$

$$N = \tfrac{1}{2}\left[3\left|e_p^{2\omega}\right|^2 + \left|e_s^{2\omega}\right|^2\right] \quad (61e)$$

UNITED STATES PATENT AND TRADEMARK OFFICE
CERTIFICATE OF CORRECTION

PATENT NO. : 7,336,359 B1
APPLICATION NO. : 11/120350
DATED : February 26, 2008
INVENTOR(S) : Garth J. Simpson It is certified that error appears in the above-identified patent and that said Letters Patent is hereby corrected as shown below:

In column 43, lines 1-5, please change

" $$\tan(2\phi_p) = \frac{B}{A} = \frac{2Re(\chi_{ppp}\chi_{spp}^*)}{|\chi_{ppp}|^2 + |\chi_{spp}|^2} \qquad (79)$$ "

To

-- $$\tan(2\phi_p) = \frac{B}{A} = \frac{2\,\text{Re}\left(\chi_{ppp}\chi_{spp}^*\right)}{\left|\chi_{ppp}\right|^2 + \left|\chi_{spp}\right|^2} \qquad (79)$$ --

In column 43, lines 23-32, please change

" $$\chi_{ZZZ} = N_s[\langle\cos^3\theta\rangle\beta_{z'z'z'} + \langle\sin^2\theta\cos\theta\cos^2\psi\rangle(\beta_{z'x'x'} + 2\beta_{x'x'z'})] \qquad (80)$$

$$\chi_{ZXX} = \tfrac{1}{2}N_s[\langle\sin^2\theta\cos\theta\rangle\beta_{z'z'z'} + \langle\cos\theta\rangle\beta_{z'x'x'} - \langle\sin^2\theta\cos\theta\cos^2\psi\rangle(\beta_{z'x'x'} + 2\beta_{x'x'z'})] \qquad (81)$$

$$\chi_{XXZ} = \tfrac{1}{2}N_s[\langle\sin^2\theta\cos\theta\rangle\beta_{z'z'z'} + \langle\cos\theta\rangle\beta_{x'x'z'} - \langle\sin^2\theta\cos\theta\cos^2\psi\rangle(\beta_{z'x'x'} + 2\beta_{x'x'z'})] \qquad (82)$$

$$\chi_{XYZ} = \tfrac{1}{2}N_s[\langle\sin^2\theta\sin\psi\cos\psi\rangle(\beta_{x'x'z'} - \beta_{z'x'x'})] \qquad (83)$$ "

To

-- $$\chi_{ZZZ} = N_s\left[\langle\cos^3\theta\rangle\beta_{z'z'z'} + \langle\sin^2\theta\cos\theta\cos^2\psi\rangle\left(\beta_{z'x'x'} + 2\beta_{x'x'z'}\right)\right] \qquad (80)$$

$$\chi_{ZXX} = \tfrac{1}{2}N_s\left[\langle\sin^2\theta\cos\theta\rangle\beta_{z'z'z'} + \langle\cos\theta\rangle\beta_{z'x'x'} - \langle\sin^2\theta\cos\theta\cos^2\psi\rangle\left(\beta_{z'x'x'} + 2\beta_{x'x'z'}\right)\right] \qquad (81)$$

$$\chi_{XXZ} = \tfrac{1}{2}N_s\left[\langle\sin^2\theta\cos\theta\rangle\beta_{z'z'z'} + \langle\cos\theta\rangle\beta_{x'x'z'} - \langle\sin^2\theta\cos\theta\cos^2\psi\rangle\left(\beta_{z'x'x'} + 2\beta_{x'x'z'}\right)\right] \qquad (82)$$

$$\chi_{XYZ} = \tfrac{1}{2}N_s\left[\langle\sin^2\theta\sin\psi\cos\psi\rangle\left(\beta_{x'x'z'} - \beta_{z'x'x'}\right)\right] \qquad (83)$$ --

UNITED STATES PATENT AND TRADEMARK OFFICE
CERTIFICATE OF CORRECTION

PATENT NO. : 7,336,359 B1
APPLICATION NO. : 11/120350
DATED : February 26, 2008
INVENTOR(S) : Garth J. Simpson It is certified that error appears in the above-identified patent and that said Letters Patent is hereby corrected as shown below:

In column 44, lines 13-18, please change

" $$\beta_{i'j'k'}(-\omega_{swn};\omega_{vis},\underline{\omega_{ir}}) = \frac{-1}{h}\sum_n \frac{(\alpha_{0n}^{i'j'})_{AR}\mu_{n0}^{k'}}{(\omega_n - \omega_{ir} - 2i\Gamma_n)} \quad (87)$$ ,, To -- $$\beta_{i'j'k'}(-\omega_{sum};\omega_{vis},\underline{\omega_{ir}}) = \frac{-1}{h}\sum_n \frac{(\alpha_{0n}^{i'j'})_{AR}\mu_{n0}^{k'}}{(\omega_n - \omega_{ir} - 2i\Gamma_n)} \quad (87)$$ --

In column 47, lines 21-36, please change

"
TABLE 13

Comparison of FITC-BSA ρ values derived from different experimental configurations.

|  | $\rho_{-n/s}$ | $\rho_{n/s}$ | $\rho_0$ | $\rho_{n/4}$ |
|---|---|---|---|---|
| NONE | 1.80 (±.01) + 0.31i (±.01i) | −1.80 (±.05) − 0.34i (±.01i) | 0.33 (±.05) − 0.97i (±.01i) | −0.59 (±.04) + 0.84i (±.01i) |
| Rot QWP s- | 1.78 (±.02) + 0.46i (±.04i) | −1.53 (±.02) − 0.56i (±.03i) | 0.45 (±.04) − 0.93i (±.06i) | −0.47 (±.05) + 0.84i (±.04i) |
| Rot QWP p- | 1.7 (±.1) + 0.51i (±.06i) | −1.74 (±.02) − 0.62i (±.04i) | 0.48 (±.03) − 0.95i (±.06i) | −0.47 (±.07) + 0.96i (±.02i) |
| Rot HWP s- | 1.89 (±.08) ± 1.36i (±.06i) | −1.36 (±.05) ± 0.5i (±.1i) | 0.47 (±.04) ± 1.00i (±.07i) | −0.50 (±.01) ± 0.76i (±.05i) |
| Rot HWP p- | 1.8 (±.2) ± 0.7i (±.3i) | −1.05 (±.03) ± 0.86i (±.05i) | 0.52 (±.03) ± 0.94i (±.03i) | −0.32 (±.01) ± 0.82i (±.01i) |

To

--
TABLE 13

Comparison of FITC-BSA ρ values derived from different experimental configurations.

|  | $\rho_{-s1}$ | $\rho_{n/s}$ | $\rho_0$ | $\rho_{n/4}$ |
|---|---|---|---|---|
| NONE | 1.80 (±.01) + 0.31i (±.01i) | −1.80 (±.05) − 0.34i (±.01i) | 0.33 (±.05) − 0.97i (±.01i) | −0.59 (±.04) + 0.84i (±.01i) |
| Rot QWP *s*- | 1.78 (±.02) + 0.46i (±.04i) | −1.53 (±.02) − 0.56i (±.03i) | 0.45 (±.04) − 0.93i (±.06i) | −0.47 (±.05) + 0.84i (±.04i) |
| Rot QWP *p*- | 1.7 (±.1) + 0.51i (±.06i) | −1.74 (±.02) − 0.62i (±.04i) | 0.48 (±.03) − 0.95i (±.06i) | −0.47 (±.07) + 0.96i (±.02i) |
| Rot HWP *s*- | 1.89 (±.08) ± 1.36i (±.06i) | −1.36 (±.05) ± 0.5i (±.1i) | 0.47 (±.04) ± 1.00i (±.07i) | −0.50 (±.01) ± 0.76i (±.05i) |
| Rot HWP *p*- | 1.8 (±.2) ± 0.7i (±.3i) | −1.05 (±.03) ± 0.86i (±.05i) | 0.52 (±.03) ± 0.94i (±.03i) | −0.32 (±.01) ± 0.82i (±.01i) |

--

UNITED STATES PATENT AND TRADEMARK OFFICE
CERTIFICATE OF CORRECTION

PATENT NO.      : 7,336,359 B1
APPLICATION NO. : 11/120350
DATED           : February 26, 2008
INVENTOR(S)     : Garth J. Simpson It is certified that error appears in the above-identified patent and that said Letters Patent is hereby corrected as shown below:

In column 47, lines 37-51, please change

"
TABLE 14
Comparison of RB-dex $\rho$ values derived from different experimental configurations.

|  | $\rho_{-\pi/4}$ | $\rho_{\pi/4}$ | $\rho_0$ | $\rho_{\pi/4}$ |
|---|---|---|---|---|
| NONE | −0.32 (±.01) + 0.35i (±.01i) | 0.35 (±.02) − 0.32i (±.01i) | 0.35 (±.03) − 1.05i (±.01i) | −0.32 (±.03) + 1.05i (±.01i) |
| Rot QWP s- | −0.28 (±.03) + 0.40i (±.01i) | 0.23 (±.02) − 0.35i (±.01i) | 0.22 (±.01) − 0.96i (±.01i) | −0.20 (±.02) + 1.05i (±.03i) |
| Rot QWP p- | −0.26 (±.04) + 0.35i (±.02i) | 0.25 (±.01) − 0.38i (±.01i) | 0.24 (±.01) − 0.93i (±.02i) | −0.19 (±.03) + 1.04i (±.03i) |
| Rot HWP s- | −0.18 (±.02) ± 0.33i (±.01i) | 0.29 (±.01) ± 0.35i (±.02i) | 0.25 (±.01) ± 1.03i (±.01i) | −0.24 (±.01) ± 1.05i (±.01i) |
| Rot HWP p- | −0.17 (±.01) ± 0.37i (±.02i) | 0.30 (±.01) ± 0.38i (±.02i) | 0.24 (±.01) ± 1.03i (±.01i) | −0.24 (±.02) ± 1.04i (±.01i) |
"

To

--
TABLE 14
Comparison of RB-dex $\rho$ values derived from different experimental configurations.

|  | $\rho_{-\pi/4}$ | $\rho_{\pi/4}$ | $\rho_0$ | $\rho_{\pi/4}$ |
|---|---|---|---|---|
| NONE | −0.32 (±.01) + 0.35i (±.01i) | 0.35 (±.02) − 0.32i (±.01i) | 0.35 (±.03) − 1.05i (±.01i) | −0.32 (±.03) + 1.05i (±.01i) |
| Rot QWP s- | −0.28 (±.03) + 0.40i (±.01i) | 0.23 (±.02) − 0.35i (±.01i) | 0.22 (±.01) − 0.96i (±.01i) | −0.20 (±.02) + 1.05i (±.03i) |
| Rot QWP p- | −0.26 (±.04) + 0.35i (±.02i) | 0.25 (±.01) − 0.38i (±.01i) | 0.24 (±.01) − 0.93i (±.02i) | −0.19 (±.03) + 1.04i (±.03i) |
| Rot HWP s- | −0.18 (±.02) ± 0.33i (±.01i) | 0.29 (±.01) ± 0.35i (±.02i) | 0.25 (±.01) ± 1.03i (±.01i) | −0.24 (±.01) ± 1.05i (±.01i) |
| Rot HWP p- | −0.17 (±.01) ± 0.37i (±.02i) | 0.30 (±.01) ± 0.38i (±.02i) | 0.24 (±.01) ± 1.03i (±.01i) | −0.24 (±.02) ± 1.04i (±.01i) |
--

In column 49, beginning at line 38, please change

"
TABLE 15
Summary of $\chi^{(2)}$ tensor elements and derived information

|  | R-6G | DR-19 | DPB |
|---|---|---|---|
| $\chi_{xxx}$ | 1 | 1 | 1 |
| $\chi_{xxx}$ | −0.04 (±0.03) + 0.37i (±0.03i) | 1.00 (±0.04) − 0.04i (±0.04i) | 1.34 (±0.01) + 1.1i (±0.1i) |
| $\chi_{xzz}$ | 1.42 (±0.01) − 0.24i (±0.04i) | 2.74 (±0.05) + 0.75i (±0.01i) | 2.43 (±0.07) + 1.75i (±0.09i) |
| $\chi_{zxx}/\chi_{xxx}$ | −1.81 (±0.02) − 0.7i (±0.1i) | 2.72 (±0.02) + 0.9i (0.1i) | 1.7 (±0.1) − 0.12i (±0.08i) |
| D | 0.61 (±0.01) − 0.05i (±0.01i) | 0.59 (±0.01) + 0.07i (±0.01i) | 0.52 (±0.02) + 0.07i (±0.04i) |
| θ° | 38.5° (±0.7°) | 39.5° (±0.9°) | 43° (±2°) |
| $R_{exp}$ | — | 0.00 (±0.02) + 0.02i (±0.01i) | −0.29 (±.02) − 0.21i (±0.03i) |
| $R_{cal}$ | — | −0.02 | −0.02 |

*All of the $\chi^{(2)}$ tensor elements are normalized to $\chi_{xxx}$.
"

UNITED STATES PATENT AND TRADEMARK OFFICE
CERTIFICATE OF CORRECTION

PATENT NO. : 7,336,359 B1
APPLICATION NO. : 11/120350
DATED : February 26, 2008
INVENTOR(S) : Garth J. Simpson It is certified that error appears in the above-identified patent and that said Letters Patent is hereby corrected as shown below:

To

TABLE 1.5
Summary of $\chi^{(2)}$ tensor elements and derived information

| | R-6G | DR-19 | DPB |
|---|---|---|---|
| $\chi_{xxz}$ | 1 | 1 | 1 |
| $\chi_{zxx}$ | -0.64 (± 0.03) + 0.37i (± 0.03i) | 1.00 (± 0.04) - 0.04i (± 0.04i) | 1.34 (± 0.01) + 1.1i (± 0.1i) |
| $\chi_{zzz}$ | 1.42 (± 0.01) - 0.24i (± 0.04i) | 2.74 (± 0.05) + 0.75i (± 0.01i) | 2.43 (± 0.07) + 1.75i (± 0.09i) |
| $\chi_{zzz}$ | | | |
| $\eta_{zxx}$ | -1.81 (± 0.02) - 0.7i (± 0.1i) | 2.72 (± 0.02) + 0.9i (± 0.1i) | 1.7 (± 0.1) - 0.12i (± 0.08i) |
| D | 0.61 (± 0.01) - 0.05i (± 0.01i) | 0.59 (± 0.01) + 0.07i (± 0.01i) | 0.52 (± 0.02) + 0.07i (± 0.04i) |
| θ | 38.5° (± 0.7°) | 39.5° (± 0.9°) | 43° (± 2°) |
| $R_{up}$ | — | 0.00 (± 0.02) + 0.02i (± 0.01i) | -0.29 (± .02) - 0.21i (± 0.03i) |
| $R_{cal}$ | — | -0.02 | -0.02 |

* All of the $\chi^{(2)}$ tensor elements are normalized to $\chi_{xxz}$.

In column 54, lines 10-12, please change

" $e_x^\omega = \hat{e}_x^\omega [t_{p13}^\omega - t_{p13}^\omega r_{p32}^\omega e^{-i\beta^\omega} + t_{p13}^\omega r_{p32}^\omega r_{p31}^\omega e^{-i2\beta^\omega} - t_{p13}^\omega r_{p32}^\omega r_{p31}^\omega r_{p32}^\omega e^{-i2\beta^\omega} + \ldots ]$ (S.8) "

To

-- $e_x^\omega = \hat{e}_x^\omega \left[ t_{p13}^\omega - t_{p13}^\omega r_{p32}^\omega e^{-i\beta^\omega} + t_{p13}^\omega r_{p32}^\omega r_{p31}^\omega e^{-i2\beta^\omega} - t_{p13}^\omega r_{p32}^\omega r_{p31}^\omega r_{p32}^\omega e^{-i2\beta^\omega} + \ldots \right]$ (S.8) --

In column 56, lines 45-49, please change

" $s_s^A \cong s_s^B (n_3^{2\omega} \cos\theta_3^{2\omega} / n_1^{2\omega} \cos\theta_1^{2\omega})(\sin\theta_1^{2\omega} / \sin\theta_3^{2\omega})$ (S.18e) "

$= s_s^B \left[ (n_3^{2\omega})^2 \cos\theta_3^{2\omega} / (n_1^{2\omega})^2 \cos\theta_1^{2\omega} \right]$ To -- $s_s^A \cong s_s^B \left( n_3^{2\omega} \cos\theta_3^{2\omega} / n_1^{2\omega} \cos\theta_1^{2\omega} \right)\left( \sin\theta_1^{2\omega} / \sin\theta_3^{2\omega} \right)$ --

$= s_s^B \left[ \left( n_3^{2\omega} \right)^2 \cos\theta_3^{2\omega} / \left( n_1^{2\omega} \right)^2 \cos\theta_1^{2\omega} \right]$ (S.18e)

UNITED STATES PATENT AND TRADEMARK OFFICE
CERTIFICATE OF CORRECTION

PATENT NO. : 7,336,359 B1
APPLICATION NO. : 11/120350
DATED : February 26, 2008
INVENTOR(S) : Garth J. Simpson It is certified that error appears in the above-identified patent and that said Letters Patent is hereby corrected as shown below:

In column 57, lines 19-23, please change $$``\quad \frac{\chi_{XYZ}}{\chi_{YXZ}} = -\frac{s_2^A \chi_{psp}}{s_4^A \chi_{spp}} = -\frac{(1+r_{s/2}^{2\omega})(1-r_{p/2}^{\omega})}{(1-r_{p/2}^{2\omega})(1+r_{s/2}^{\omega})} \frac{\cos\theta_3^{2\omega}}{\cos\theta_1^{2\omega}} \frac{\chi_{psp}}{\chi_{spp}} \qquad (S.20)\ ,,$$

To $$--\quad \frac{\chi_{XYZ}}{\chi_{YXZ}} = -\frac{s_2^A \chi_{psp}}{s_4^A \chi_{spp}} = -\frac{\left(1+r_{s12}^{2\omega}\right)\left(1-r_{p12}^{\omega}\right)}{\left(1-r_{p12}^{2\omega}\right)\left(1+r_{s12}^{\omega}\right)} \frac{\cos\theta_3^{2\omega}}{\cos\theta_1^{2\omega}} \frac{\chi_{psp}}{\chi_{spp}} \qquad (S.20)\ --$$

Signed and Sealed this

Nineteenth Day of May, 2009

*John Doll*

JOHN DOLL
*Acting Director of the United States Patent and Trademark Office*